United States Patent
Kang et al.

(10) Patent No.: US 10,745,701 B2
(45) Date of Patent: *Aug. 18, 2020

(54) METHODS OF IDENTIFYING AND TREATING POOR-PROGNOSIS CANCERS

(71) Applicant: The Trustees of Princeton University, Princeton, NJ (US)

(72) Inventors: Yibin Kang, Princeton, NJ (US); Guohong Hu, Piscataway, NJ (US)

(73) Assignee: The Trustees Of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,098

(22) Filed: Dec. 21, 2018

(65) Prior Publication Data

US 2019/0292548 A1    Sep. 26, 2019

Related U.S. Application Data

(63) Continuation of application No. 15/901,174, filed on Feb. 21, 2018, now Pat. No. 10,202,605, which is a continuation of application No. 15/004,706, filed on Jan. 22, 2016, now Pat. No. 9,932,587, which is a continuation of application No. 14/619,977, filed on Feb. 11, 2015, now abandoned, which is a continuation of application No. 12/215,998, filed on Jun. 30, 2008, now abandoned.

(60) Provisional application No. 60/937,789, filed on Jun. 28, 2007.

(51) Int. Cl.

| C12N 15/113 | (2010.01) |
| A61K 31/713 | (2006.01) |
| C12Q 1/6886 | (2018.01) |
| A61K 45/06 | (2006.01) |
| A61K 31/7105 | (2006.01) |
| A61K 31/337 | (2006.01) |
| A61K 31/704 | (2006.01) |
| A61K 31/00 | (2006.01) |

(52) U.S. Cl.
CPC .......... *C12N 15/1135* (2013.01); *A61K 31/00* (2013.01); *A61K 31/337* (2013.01); *A61K 31/704* (2013.01); *A61K 31/713* (2013.01); *A61K 31/7105* (2013.01); *A61K 45/06* (2013.01); *C12Q 1/6886* (2013.01); *C12N 2310/11* (2013.01); *C12N 2310/14* (2013.01); *C12N 2320/30* (2013.01); *C12N 2320/31* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 3,687,808 A | 8/1972 | Merigan, Jr. et al. ....... 435/91.3 |
| 4,323,546 A | 4/1982 | Crockford et al. .......... 424/1.49 |
| 4,683,195 A | 7/1987 | Mullis et al. ................ 435/6.11 |
| 4,683,202 A | 7/1987 | Mullis .......................... 435/91.2 |
| 4,965,188 A | 10/1990 | Mullis et al. ................. 435/6.12 |
| 4,981,785 A | 1/1991 | Nayak .......................... 435/7.94 |
| 5,030,559 A | 7/1991 | Nicolson et al. ............. 435/7.23 |
| 5,034,506 A | 7/1991 | Summerton et al. ......... 528/391 |
| 5,223,409 A | 6/1993 | Ladner et al. ..................... 506/1 |
| 5,358,691 A | 10/1994 | Clark et al. ...................... 422/64 |
| 5,489,677 A | 2/1996 | Sanghvi et al. .............. 536/22.1 |
| 5,538,848 A | 7/1996 | Livak et al. ................. 435/6.16 |
| 5,539,082 A | 7/1996 | Nielsen et al. ................ 530/300 |
| 5,565,332 A | 10/1996 | Hoogenboom et al. ..... 435/69.1 |
| 5,585,089 A | 12/1996 | Queen et al. ............... 424/133.1 |
| 5,599,677 A | 2/1997 | Dowell et al. ................. 435/7.4 |
| 5,602,240 A | 2/1997 | De Mesmaeker et al. .. 536/22.1 |
| 5,639,606 A | 6/1997 | Willey .......................... 435/6.12 |
| 5,643,765 A | 7/1997 | Willey .......................... 435/91.2 |
| 5,672,480 A | 9/1997 | Dowell et al. ................. 435/7.4 |
| 5,705,188 A | 1/1998 | Junichi et al. ................ 424/450 |
| 5,714,331 A | 2/1998 | Buchardt ..................... 435/6.14 |
| 5,719,262 A | 2/1998 | Buchardt ...................... 530/300 |
| 5,736,137 A | 4/1998 | Anderson et al. ......... 424/133.1 |
| 5,824,544 A | 10/1998 | Armentano et al. ....... 435/320.1 |
| 5,830,730 A | 11/1998 | German et al. ............... 435/455 |
| 5,872,154 A | 2/1999 | Wilson et al. ............. 424/154.1 |
| 5,876,978 A | 3/1999 | Willey et al. ................. 435/91.2 |
| 5,885,530 A | 3/1999 | Babson et al. .................. 422/65 |
| 5,885,808 A | 3/1999 | Spooner ....................... 435/456 |
| 5,981,225 A | 11/1999 | Kochanek et al. .......... 435/69.1 |
| 5,994,106 A | 11/1999 | Kovesdi et al. ............. 435/91.4 |
| 5,994,128 A | 11/1999 | Fallaux et al. ................ 435/325 |
| 5,994,132 A | 11/1999 | Chamberlain et al. ....... 435/369 |
| 6,001,557 A | 12/1999 | Wilson et al. ..................... 435/5 |
| 6,019,978 A | 2/2000 | Ertl et al. ................... 424/199.1 |
| 6,033,908 A | 3/2000 | Bout et al. .................... 435/325 |
| 6,054,297 A | 4/2000 | Carter et al. ................. 435/69.6 |
| 6,159,685 A | 12/2000 | Pinkel et al. ................ 435/6.14 |
| 6,159,750 A | 12/2000 | Edmonds ..................... 436/537 |

(Continued)

FOREIGN PATENT DOCUMENTS

| WO | WO 1997/30731 | 8/1997 |
| WO | WO 1999/02685 | 1/1999 |

(Continued)

OTHER PUBLICATIONS

US 5,962,233 (withdrawn).

(Continued)

*Primary Examiner* — Sean McGarry
(74) *Attorney, Agent, or Firm* — Medlen & Carroll, LLP

(57) ABSTRACT

The present invention relates generally to methods for identifying cancer patients with a poor prognosis, and to therapeutic modalities for improving prognosis by combating metastasis and abrogating chemoresistance in cancer cells. Embodiments of the present invention provide an objective means of prognostication regarding the long-term outcome of an incident of cancer, breast cancer in particular. Therapeutic modalities include immunotherapy and antisense therapy. Prognosis is determined by measuring the number of copies of the metadherin gene in the patient's cells.

20 Claims, 15 Drawing Sheets

Specification includes a Sequence Listing.

(56) References Cited

U.S. PATENT DOCUMENTS

| | | | |
|---|---|---|---|
| 6,180,349 | B1 | 1/2001 | Ginzinger et al. ............ 435/6.11 |
| 6,180,370 | B1 | 1/2001 | Queen et al. ................ 435/69.6 |
| 6,198,107 | B1 | 3/2001 | Seville ...................... 250/458.1 |
| 6,312,694 | B1 | 11/2001 | Thorpe et al. ............. 424/178.1 |
| 6,506,559 | B1 | 1/2003 | Fire et al. ..................... 435/6.16 |
| 7,273,855 | B2 | 9/2007 | Jupe ............................. 514/44 R |
| 2003/0022854 | A1 | 1/2003 | Dow et al. .................. 514/44 A |
| 2004/0138171 | A1 | 7/2004 | Suzuki et al. .................. 514/53 |
| 2004/0171552 | A1 | 9/2004 | Peled et al. ..................... 514/1.4 |
| 2005/0208057 | A1 | 9/2005 | Ruoslahti et al. ......... 424/155.1 |
| 2007/0087345 | A1 | 4/2007 | Olson-Munoz et al. .... 435/6.11 |
| 2008/0090233 | A1 | 4/2008 | Garcia et al. ................ 435/6.14 |

FOREIGN PATENT DOCUMENTS

| | | |
|---|---|---|
| WO | WO1999/60010 | 11/1999 |
| WO | WO 2000/09675 | 2/2000 |
| WO | WO 2000/12738 | 3/2000 |
| WO | WO 2001/98537 | 12/2001 |
| WO | WO 2003/070966 | 8/2003 |
| WO | WO 2003/072599 | 9/2003 |
| WO | WO 2003/075853 | 9/2003 |
| WO | WO 2003/084993 | 10/2003 |
| WO | WO 2004/071460 | 8/2004 |
| WO | WO 2004/071499 | 8/2004 |
| WO | WO 2004/098512 | 11/2004 |
| WO | WO 2004/098516 | 11/2004 |
| WO | WO 2005/020899 | 3/2005 |
| WO | WO 2005/021498 | 3/2005 |
| WO | WO 2005/021499 | 3/2005 |
| WO | WO 2005/021500 | 3/2005 |
| WO | WO 2005/038054 | 4/2005 |
| WO | WO 2005/050198 | 6/2005 |
| WO | WO 2005/054270 | 6/2005 |
| WO | WO2005/115481 | 12/2005 |
| WO | WO 2006/015312 | 2/2006 |
| WO | WO 2006/093494 | 9/2006 |

OTHER PUBLICATIONS

Amano, et al. "Dosage-Dependent over-Expression of Genes in the Trisomic Region of TslCje Mouse Model for Down Syndrome." *Hum Mol Genet*, 13(13):1333-1340 (2004).

Anderson and Young, "Quantitative Filter Hybridization." In *Nucleic Acid Hybridisation: A Practical Approach* (Hames, et al, Eds.), pp. 73-111, IRL Press, Oxford Washington, DC (1985).

Ballestrero, et al. "Tumor Necrosis Factor-Related Apoptosis-Inducing Ligand Cooperates with Anticancer Drugs to Overcome Chemoresistance in Antiapoptotic Bcl-2 Family Members Expressing Jurkat Cells." *Clin Cancer Res*, 10(4): 1463-1470 (2004).

Bergamaschi, et al. "Distinct Patterns of DNA Copy Number Alteration Are Associated with Different Clinicopathological Features and Gene-Expression Subtypes of Breast Cancer." *Genes Chromosomes Cancer*, 45(11): 1033-1040 (2006).

Bernards and Weinberg, "A Progression Puzzle." *Nature*, 418(6900):823 (2002).

Bertram, et al. "Increase of P-Glycoprotein-Mediated Drug Resistance by Hsp 90 beta." *Anticancer Drugs*, 7(8):838-845 (1996).

Birchmeier, et al. "Met, Metastasis, Motility and More." *Nat Rev Mol Cell Biol*, 4(12):915-925 (2003).

Bohula, et al. "The Efficacy of Small Interfering RNAs Targeted to the Type 1 Insulin-Like Growth Factor Receptor (IGF1R) Is Influenced by Secondary Structure in the (IGF1R) Transcript." *J Biol Chem*, 278(18):15991-15997 (2003).

Britt, et al. "Identification of a Novel Protein, Lyric, Localized to Tight Junctions of Polarized Epithelial Cells." *Exp Cell Res*, 300(1):134-148 (2004).

Brown and Ruoslahti, "Metadherin, a Cell Surface Protein in Breast Tumors That Mediates Lung Metastasis." *Cancer Cell*, 5(4):365-374 (2004).

Brummelkamp, et al. "A System for Stable Expression of Short Interfering RNAs in Mammalian Cells." *Science*, 296(5567):550-553 (2002).

Caplen et al, "Specific Inhibition of Gene Expression by Small Double-Stranded RNAs in Invertebrate and Vertebrate Systems." *Proc Natl Acad Sci USA*, 98(17):9742-9747 (2001).

Carell, et al. "A Novel Procedure for the Synthesis of Libraries Containing Small Organic Molecules." *Angewandte Chemie International Edition in English*, 33(20):2059-2061 (1994).

Carell, et al. "A Solution-Phase Screening Procedure for the Isolation of Active Compounds from a Library of Molecules." *Angewandte Chemie International Edition in English*, 33(20):2061-2064 (1994).

Carrasco, et al. "High-Resolution Genomic Profiles Define Distinct Clinico-Pathogenetic Subgroups of Multiple Myeloma Patients." *Cancer Cell*, 9(4):313-325 (2006).

Carthew, "Gene Silencing by Double-Stranded RNA." *Curr Opin Cell Biol*, 13(2):244-248 (2001).

Chambers, et al. "Dissemination and Growth of Cancer Cells in Metastatic Sites." *Nat Rev Cancer*, 2(8):563-572 (2002).

Chen, et al. "Gene Expression Patterns in Human Liver Cancers." *Mol Biol Cell*, 13(6):1929-1939 (2002).

Chin, et al. "Genomic and Transcriptional Aberrations Linked to Breast Cancer Pathophysiologies." *Cancer Cell*, 10(6):529-541 (2006).

Cho, et al. "An Unnatural Biopolymer." *Science*, 261(5126):1303-1305 (1993).

Clark, et al, "Genomic Analysis of Metastasis Reveals an Essential Role for Rhoc." *Nature*, 406(6795):532-535 (2000).

Crawley and Furge, "Identification of Frequent Cytogenetic Aberrations in Hepatocellular Carcinoma Using Gene-Expression Microarray Data." *Genome Biol*, 3(12):1-8 (2002).

Cull et al., "Screening for receptor ligands using large libraries of peptides linked to the C terminus of the lac repressor." Proc. Natl. Acad. Sci. USA 89:1865-1869 (1992).

Cwirla, et al. "Peptides on Phage: A Vast Library of Peptides for Identifying Ligands." *Proc Natl Acad Sci USA*, 87(16):6378-6382 (1990).

Devlin, et al. "Random Peptide Libraries: A Source of Specific Protein Binding Molecules." *Science*, 249(4967):404-406 (1990).

DeWitt, et al. "Diversomers: An Approach to Nonpeptide, Nonoligomeric Chemical Diversity." *Proc Natl Acad Sci USA*, 90(15):6909-6913 (1993).

Elbashir, et al. "Duplexes of 21-Nucleotide RNAs Mediate RNA Interference in Cultured Mammalian Cells." *Nature*, 411(6836):494-498 (2001).

Elbashir, et al. "RNA Interference Is Mediated by 21- and 22-Nucleotide RNAs." *Genes Dev*, 15(2): 188-200 (2001).

Elbashir, et al. "Functional Anatomy of SiRNAs for Mediating Efficient RNAi in Drosophila Melanogaster Embryo Lysate." *EMBO J*, 20(23):6877-6888 (2001).

Engelman, et al. "Met Amplification Leads to Gefitinib Resistance in Lung Cancer by Activating ERBB3 Signaling." *Science*, 316(5827):1039-1043 (2007).

Erb, et al. "Recursive Deconvolution of Combinatorial Chemical Libraries." *Proc Natl Acad Sci USA*, 91(24):11422-11426 (1994).

Fan, et al. "Concordance among Gene-Expression-Based Predictors for Breast Cancer." *N Engl J Med*, 355(6):560-569 (2006).

Felici, et al. "Selection of Antibody Ligands from a Large Library of Oligopeptides Expressed on a Multivalent Exposition Vector." *J Mol Biol*, 222(2):301-310(1991).

Fidler, "The Pathogenesis of Cancer Metastasis: The 'Seed and Soil' Hypothesis Revisited." *Nat Rev Cancer*, 3(6):453-458 (2003).

Fodor, et al. "Multiplexed Biochemical Assays with Biological Chips." *Nature*, 364(6437):555-556 (1993).

Freije, et al. "Gene Expression Profiling of Gliomas Strongly Predicts Survival." *Cancer Res*, 64(18):6503-6510 (2004).

Gallop, et al. "Applications of Combinatorial Technologies to Drug Discovery. 1. Background and Peptide Combinatorial Libraries." *J Med Chem*, 37(9): 1233-1251 (1994).

Garraway, et al. "Integrative Genomic Analyses Identify Mitf as a Lineage Survival Oncogene Amplified in Malignant Melanoma." *Nature*, 436(7047): 117-122 (2005).

(56) References Cited

OTHER PUBLICATIONS

Ghose, et al. "Preparation of Antibody-Linked Cytotoxic Agents." *Methods Enzymol*, 93:280-333 (1983).
Gillett, et al. "Amplification and Overexpression of Cyclin D1 in Breast Cancer Detected by Irnmunohistochemical Staining." *Cancer Res*, 54(7): 1812-1817 (1994).
Glockner, et al. "Amplification of Growth Regulatory Genes in Intraductal Breast Cancer Is Associated with Higher Nuclear Grade but Not with the Progression to Invasiveness." *Lab Invest*, 81(4):565-571 (2001).
Griffin, et al. "Initial Clinical Study of Indium-111-Labeled Clone 110 Anticarcmoembryonic Antigen Antibody in Patients with Colorectal Cancer." *J Clin Oncol*, 9(4):631-640 (1991).
Gupta and Massague, "Cancer Metastasis: Building a Framework." *Cell*, 127(4):679-695 (2006).
Hanahan and Weinberg, "The Hallmarks of Cancer." *Cell*, 100(1):57-70 (2000).
Hertzberg et al, "Prediction of Chromosomal Aneuploidy from Gene Expression Data." *Genes Chromosomes Cancer*, 46(1):75-86 (2007).
Hnatowich, et al, "The Preparation and Labeling of Dtpa-Coupled Albumin." *Int JApplRadiat Isot*, 33(5):327-332 (1982).
Holen, et al. "Positional Effects of Short Interfering RNAs Targeting the Human Coagulation Trigger Tissue Factor." *Nucleic Acids Res*, 30(8):1757-1766 (2002).
Houghten, et al. "The Use of Synthetic Peptide Combinatorial Libraries for the Identification of Bioactive Peptides." *Biotechniques*, 13(3):412-421 (1992).
Janssen, et al., "In Lymph Node-Negative Invasive Breast Carcinomas, Specific Chromosomal Aberrations Are Strongly Associated with High Mitotic Activity and Predict Outcome More Accurately Than Grade, Tumour Diameter, and Oestrogen Receptor." *J Pathol*, 201(4):555-561 (2003).
Kallioniemi, et al., "Comparative Genomic Hybridization for Molecular Cytogenetic Analysis of Solid Tumors." *Science*, 258(5083):818-821 (1992).
Kang, et al., "A Multigenic Program Mediating Breast Cancer Metastasis to Bone." *Cancer Cell*, 3(6):537-549 (2003).
Kang, et al., "Cloning and Characterization of HIV-1-Inducible Astrocyte Elevated Gene-1, Acg-1." *Gene*, 353(1):8-15 (2005a).
Kang, "Functional Genomic Analysis of Cancer Metastasis: Biologic Insights and Clinical Implications." *Expert Rev MolDiagn*, 5(3):385-395 (2005b).
Khaw, et al., "Myocardial Infarct Imaging of Antibodies to Canine Cardiac Myosin with Indium-111-Diethylenetriamine Pentaacetic Acid." *Science*, 209(4453):295-297 (1980).
Kim, et al., "Comparative Oncogenomics Identifies Nedd9 as a Melanoma Metastasis Gene." *Cell*, 125(7):1269-1281 (2006).
Kohler and Milstein, "Continuous Cultures of Fused Cells Secreting Antibody of Predefined Specificity." *Nature*, 256(5517):495-497 (1975).
Kretschmer-Kazemin and FarSczakiel, "The Activity of siRNA in Mammalian Cells Is Related to Structural Target Accessibility: A Comparison with Antisense Oligonucleotides." *Nucleic Acids Res*, 31(15):4417-4424 (2003).
Lam, et al., "A New Type of Synthetic Peptide Library for Identifying Ligand-Binding Activity." *Nature*, 354(6348):82-84 (1991).
Lam, "Application of Combinatorial Library Methods in Cancer Research and Drug Discovery." *Anticancer Drug Des*, 12(3): 145-167 (1997).
Lauffer, "Targeted Relaxation Enhancement Agents for MRI." *Magnetic Resonance in Medicine*, 22(2):339-342 (1991).
Lapointe, et al., "Gene Expression Profiling Identifies Clinically Relevant Subtypes of Prostate Cancer." *Proc Natl Acad Sci USA*, 101(3):811-816 (2004).
Lehmann, et al., "Detection of Gene Amplification in Archival Breast Cancer Specimens by Laser-Assisted Microdissection and Quantitative Real-Time Polymerase Chain Reaction." *Am J Pathol*, 156(6):1855-1864 (2000).

Lin, et al., "Expression Cloning of Human EGF Receptor Complementary DNA: Gene Amplification and Three Related Messenger RNA Products in A431 Cells." *Science*, 224(4651):843-848 (1984).
Lin, et al., "Long-Term Tumor-Free Survival from Treatment with the GFP-Trail Fusion Gene Expressed from the HTERT Promoter in Breast Cancer Cells." *Oncogene*, 21(52):8020-8028 (2002).
Liu, et al., "A Genome-Wide Screen Reveals Functional Gene Clusters in the Cancer Genome and Identifies Epha2 as a Mitogen in Glioblastoma." *Cancer Research*, 66(22): 10815-10823 (2006a).
Liu, et al., "Full-Length Adamts-1 and the Adamts-1 Fragments Display Pro- and Antimetastatic Activity, Respectively." *Oncogene*, 25(17):2452-2467 (2006b).
Lorenzato, et al., "Novel Somatic Mutations of the Met Oncogene in Human Carcinoma Metastases Activating Cell Motility and Invasion." *Cancer Res*, 62(23):7025-7030 (2002).
Manka, et al., "Bcl-2/Adenovirus Elb 19 KDa Interacting Protein-3 Knockdown Enables Growth of Breast Cancer Metastases in the Lung, Liver, and Bone." *Cancer Res*, 65(24):11689-11693 (2005).
Martin, "Ein Neuer Zugang Zu 2'-0-Alkylribonucleosiden Und Eigenschaften Deren Oligonucleotide (a New Access to 2'-O-Alkylated Ribonucleosides and Properties of 2-0-Alkylated Oligoribonucleotides)." *Helvetica Chimica Acta*, 78(2):486-504 (1995).
Massague, "Sorting out Breast-Cancer Gene Signatures." *N Engl J Med*, 356(3):294-297 (2007).
Matsuzaki, et al, "Genotyping over 100,000 Snps on a Pah of Oligonucleotide Arrays." *Nat Meth*, 1(2): 109-111 (2004).
Mellor and Harris, "The Role of the Hypoxia-Inducible BH3-Only Proteins BNIP3 and BNIP31 in Cancer." *Cancer Metastasis Rev*, 26(3-4):553-566 (2007).
Merlino, et al., "Amplification and Enhanced Expression of the Epidermal Growth Factor Receptor Gene in A431 Human Carcinoma Cells." *Science*, 224(4647):417-419(1984).
Minn, et al., "Distinct Organ-Specific Metastatic Potential of Individual Breast Cancer Cells and Primary Tumors." *J Clin Invest*, 115(1):44-55 (2005a).
Minn, et al., "Genes That Mediate Breast Cancer Metastasis to Lung." *Nature*, 436(7050):518-524 (2005b).
Muleris, et al., "Detection of DNA Amplification in 17 Primary Breast Carcinomas with Homogeneously Staining Regions by a Modified Comparative Genomic Hybridization Technique." *Genes Chromosomes Cancer*, 10(3): 160-170 (1994).
Myers, et al., "Accurate Detection of Aneuploidies in Array CGH and Gene Expression Microarray Data." *Bioinformatics*, 20(18):3533-3543 (2004).
Naylor, et al., "High Resolution Genomic Analysis of Sporadic Breast Cancer Using Array-Based Comparative Genomic Hybridization." *Breast Cancer Res*, 7(6):R1186-1198 (2005).
Needleman and Wunsch, "A General Method Applicable to the Search for Similarities in the Amino Acid Sequence of Two Proteins." *J Mol Biol*, 48(3):443-453 (1970).
Ngo, et al., "A Loss-of-Function RNA Interference Screen for Molecular Targets in Cancer." *Nature*, 441(7089): 106-110 (2006).
Nielsen, et al., "Sequence-Selective Recognition of DNA by Strand Displacement with a Thymine-SubstitutedPolyamide." *Science*, 254(5037): 1497-1500 (1991).
Olshen, et al., "Circular Binary Segmentation for the Analysis of Array-Based DNA Copy Number Data." *Biostatistics*, 5(4):557-572 (2004).
Overhoff, et al., "Local RNA Target Structure Influences siRNA Efficacy: A Systematic Global Analysis." *J Mol Biol*, 348(4):871-881 (2005).
Park, et al., "Syndecan-2 Mediates Adhesion and Proliferation of Colon Carcinoma Cells." *J Biol Chem*, 277(33):29730-29736 (2002).
Pearson and Lipman, "Improved Tools for Biological Sequence Comparison." *Proc Natl Acad Sci, USA*, 85(8):2444-2448 (1988).
Perou, et al., "Molecular Portraits of Human Breast Tumours." *Nature*, 406(6797):747-752 (2000).
Pinto, et al., "Frequent 7q Gains in Flow Cytometric Multiploid/Hypertetraploid Breast Carcinomas: A Study of Chromosome Imbalances by Comparative Genomic Hybridisation." *J Clin Pathol*, 59(4):367-372 (2006).

(56) References Cited

OTHER PUBLICATIONS

Pollack, et al., "Microarray Analysis Reveals a Major Direct Role of DNA Copy Number Alteration in the Transcriptional Program of Human Breast Tumors." *Proc Natl Acad Sci, USA*, 99(20):12963-12968 (2002).
Ramaswamy, et al., "A Molecular Signature of Metastasis in Primary Solid Tumors." *Nat Genet*, 33(1):49-54 (2003).
Sambrook, et al., "Molecular Cloning: A Laboratory Manual." 2nd ed., pp. pp. 9.31-39.58, Cold Spring Harbor Laboratory, Cold Spring Harbor, N.Y. (1989).
Sambrook, et al., "Molecular Cloning: A Laboratory Manual." 2nd ed., pp. 7.39-37.52, Cold Spring Harbor Laboratory, Cold Spring Harbor, N.Y. (1989).
Scheinberg, et al., "Tumor Imaging with Radioactive Metal Chelates Conjugated to Monoclonal Antibodies." *Science*, 215(4539): 1511-1513 (1982).
Schubert, et al., "Local RNA Target Structure Influences siRNA Efficacy: Systematic Analysis of Intentionally Designed Binding Regions." *J Mol Biol*, 348(4):883-893 (2005).
Schwab, et al., "Amplified DNA with Limited Homology to Myc Cellular Oncogene Is Shared by Human Neuroblastoma Cell Lines and a Neuroblastoma Tumour." *Nature*, 305(5931):245-248 (1983).
Scott and Smith, "Searching for Peptide Ligands with an Epitope Library." *Science*, 249(4967):386-390 (1990).
Slamon, et al., "Human Breast Cancer: Correlation of Relapse and Survival with Amplification of the Her-2/Neu Oncogene." *Science*, 235(4785):177-182 (1987).
Smith and Waterman, "Comparison of Biosequences." *Adv. Appl. Math.*, 2:482-489 (1981).
Sohail, et al., "Antisense Oligonucleotides Selected by Hybridisation to Scanning Arrays Are Effective Reagents in Vivo." *Nucleic Acids Res*, 29(10):2041-2051 (2001).
Solar, et al., "Hsp90 bihibitor Geldanamycin Increases the Sensitivity of Resistant Ovarian Adenocarcinoma Cell Line A2780cis to Cisplatin." *Neoplasma*, 54(2):127-130 (2007).
Sreerama and Sladek, "Primary Breast Tumor Levels of Suspected Molecular Determinants of Cellular Sensitivity to Cyclophosphamide, Ifosfamide, and Certain Other Anticancer Agents as Predictors of Paired Metastatic Tumor Levels of These Determinants. Rational Individualization of Cancer Chemotherapeutic Regimens." *Cancer Chemother Pharmacol*, 47(3):255-262 (2001).
Steeg, "Tumor Metastasis: Mechanistic Insights and Clinical Challenges." *Nat Med*, 12(8):895-904 (2006).
Stransky, et al., "Regional Copy Number-Independent Deregulation of Transcription in Cancer." *Nat Genet*, 38(12):1386-1396 (2006).
Sumerdon, et al., "An Optimized Antibody-Chelator Conjugate for Imaging of Carcinoembryonic Antigen with Indium-111." *Int J Rad Appl Inslrum B*, 17(2):247-254(1990).
Tanaka, et al., "Antiapoptotic Effect of Haem Oxygenase-1 Induced by Nitric Oxide in Experimental Solid Tumour." *Br J Cancer*, 88(6):902-909 (2003).
Thorpe, et al., "Selective Killing of Malignant Cells in a Leukaemic Rat Bone Marrow Using an Antibody-Ricin Conjugate." *Nature*, 297(5867):594-596 (1982).
Thorpe, et al, "Improved Antitumor Effects of Immunotoxins Prepared with Deglycosylated Ricin a-Chain and Hindered Disulfide Linkages." *Cancer Res*, 48(22):6396-6403 (1988).
Tinker, et al., "The Challenges of Gene Expression Microarrays for the Study of Human Cancer." *Cancer Cell*, 9(5):333-339 (2006).
Van de Vijver, et al., "A Gene-Expression Signature as a Predictor of Survival in Breast Cancer." *N Engl J Med*, 347(25): 1999-2009 (2002).
Van't Veer, et al., "Gene Expression Profiling Predicts Clinical Outcome of Breast Cancer." *Nature*, 415(6871):530-536 (2002).
Wang, et al., "Gene-Expression Profiles to Predict Distant Metastasis of Lymph-Node-Negative Primary Breast Cancer." *Lancet*, 365(9460):671-679 (2005).
Wang, et al., "Regional Activation of Chromosomal Arm 7q with and without Gene Amplification in Taxane-Selected Human Ovarian Cancer Cell Lines." *Genes Chromosomes Cancer*, 45(4):365-374 (2006).
Weber-Manga, et al., "Breast Cancer in Young Women (< or =35 Years): Genomic Aberrations Detected by Comparative Genomic Hybridization." *IntJ Cancer*, 107(4):583-592 (2003).
Wei and Au, "Role of Tumor Microenvironment in Chcmorcsistance." In *Integration/Interaction of Oncologic Growth* (Meadows, Ed.), pp. 285-321, Springer, Dordrecht, pp. 285-300:A (2005).
Wei and Au, "Role of Tumor Microenvironment in Chemoresistance." In *Integration/Interaction of Oncologic Growth* (Meadows, Ed.), pp. 285-321, Springer, Dordrecht, pp. 285-300:B (2005).
Weigelt, et al., "Breast Cancer Metastasis: Markers and Models." *Nat Rev Cancer*, 5(8):591-602 (2005).
West, et al., "Predicting the Clinical Status of Human Breast Cancer by Using Gene Expression Profiles." *Proc Natl Acad Sci USA*, 98(20):11462-11467 (2001).
Winter and Milstein, "Man-Made Antibodies." *Nature*, 349(6307):293-299 (1991).
Wong, et al., "A Rapid Chemical Method of Labeling Human Plasma Proteins with 99MTC—Pertechnetate at pH 7.4." *Int J Appl Radiat Isot*, 29(4-5):251-253 (1978).
Wong, et al., "Imaging Endocarditis with Tc-99m-Labeled Antibody—an Experimental Study: Concise Communication." *Journal of Nuclear Medicine*, 23(3):229-234(1982).
Xu, et al., "GPR56, an Atypical G Protein-Coupled Receptor, Binds Tissue Transglutaminase, Tg2, and Inhibits Melanoma Tumor Growth and Metastasis." *Proc Natl Acad Sci USA*, 103(24):9023-9028 (2006).
Yang, et al., "Caffeine Suppresses Metastasis in a Transgenic Mouse Model: A Prototype Molecule for Prophylaxis of Metastasis." *Clin Exp Metastasis*, 21(8):719-735 (2004a).
Yang, et al., "Twist, a Master Regulator of Morphogenesis, Plays an Essential Role in Tumor Metastasis." *Cell*, 117(7):927-939 (2004b).
Yu, et al., "Expression Profiling Identifies the Cytoskeletal Organizer Ezrin and the Developmental Homeoprotein Six-1 as Key Metastatic Regulators." *Nat Med*, 10(2): 175-181 (2004).
Zender, et al., "Identification and Validation of Oncogenes in Liver Cancer Using an Integrative Oncogenomic Approach." *Cell*, 125(7):1253-1267 (2006).
Zhou, et al., "Detection of DNA Copy Number Abnormality by Microarray Expression Analysis." *Hum Genet*, 114(5):464-467 (2004).
Zuckermann, et al., "Discovery of Nanomolar Ligands for 7-Transmembrane G-Protein-Coupled Receptors from a Diverse N-(Substituted)Glycine Peptoid Library." *J Med Chem*, 37(17):2678-2685 (1994).
Chen and Zhaori, "Potential clinical applications of siRNA technique: benefits and limitations," European J. of Clinical Investigation 41:221-232 (2010).
Whitehead, et al., "Knocking down barriers: advances in siRNA delivery," *Nature Reviews Drug Discov*, 8(2):129-138 (2009).
ClinicalTrial.gov, downloaded from the Web Aug. 25, 2017.
NCT01839604, downloaded from the Web Aug. 25, 2017.
Bumcrot, et al., "RNAi Therapeutics: A Potential New Class of Pharmaceutical Drugs." *Nat Chem Biol*, 2(12):711-719 (2006).
Dhruv, et al., "Geno-13network-Based Approach Aids in the Discovery of Context-Specific Druggable Targets for Treatment of Glioblastoma." *Neuro-Oncology*, 17(suppl_5):v94-v94 abstract No. GENO-13 (2015).
Gondi, et al., "RNAi-Mediated Inhibition of Cathepsin B and UPAR Leads to Decreased Cell Invasion, Angiogenesis and Tumor Growth in Gliomas." *Oncogene*, 23(52):8486-8496 (2004).
Guan, et al., "A Small Interfering RNA Targeting Vascular Endothelial Growth Factor Inhibits Ewing's Sarcoma Growth in a Xenograft Mouse Model." *Clin Cancer Res*, 11(7):2662-2669 (2005).
Halder, et al., "Focal Adhesion Kinase Targeting Using in Vivo Short Interfering RNA Delivery in Neutral Liposomes for Ovarian Carcinoma Therapy." *Clin Cancer Res*, 12(16):4916-4924 (2006).
Hu-Lieskovan, et al., "Sequence-Specific Knockdown of Ews-Fli1 by Targeted, Nonviral Delivery of Small Interfering RNA Inhibits Tumor Growth in a Murine Model of Metastatic Ewing's Sarcoma." *Cancer Res*, 65(19):8984-8992 (2005).

(56) References Cited

OTHER PUBLICATIONS

Ito, et al., "Rad51siRNA Delivered by HVJ Envelope Vector Enhances the Anti-Cancer Effect of Cisplatin." *J Gene Med*, 7(8):1044-1052 (2005).
Judge, et al., "Design of Noninflammatory Synthetic siRNA Mediating Potent Gene Silencing in Vivo." *Mol Ther*, 13(3):494-505 (2006).
Lakka, et al., "Inhibition of Cathepsin B and Mmp-9 Gene Expression in Glioblastoma Cell Line Via RNA Interference Reduces Tumor Cell Invasion, Tumor Growth and Angiogenesis." *Oncogene*, 23(27):4681-4689 (2004).
Minakuchi, et al., "Atelocollagen-Mediated Synthetic Small Interfering RNA Delivery for Effective Gene Silencing in Vitro and in Vivo." *Nucleic Acids Res*, 32(13):e109 (2004).
Ozcan, et al., "Preclinical and Clinical Development of siRNA-Based Therapeutics." *Adv Drug Deliv Rev*, 87:108-119 (2015).
Pal, et al., "Systemic Delivery of RafsiRNA Using Cationic Cardiolipin Liposomes Silences Raf-1 Expression and Inhibits Tumor Growth in Xenograft Model of Human Prostate Cancer." *Int J Oncol*, 26(4):1087-1091 (2005).
Schiffelers, et al., "Cancer siRNA Therapy by Tumor Selective Delivery with Ligand-Targeted Sterically Stabilized Nanoparticle." *Nucleic Acids Res*, 32(19):e149 (2004).
Silva, et al., "Meganucleases and Other Tools for Targeted Genome Engineering: Perspectives and Challenges for Gene Therapy." *Curr Gene Ther*, 11(1):11-27 (2011).
Spankuch, et al., "Cancer Inhibition in Nude Mice after Systemic Application of U6 Promoter-Driven Short Hairpin RNAs against Plk1." *J Natl Cancer Inst*, 96(11):862-872 (2004).
Sumimoto, et al., "Gene Therapy for Human Small-Cell Lung Carcinoma by Inactivation of Skp-2 with Virally Mediated RNA Interference." *Gene Ther*, 12(1):95-100 (2005).
Takei, et al., "A Small Interfering RNA Targeting Vascular Endothelial Growth Factor as Cancer Therapeutics." *Cancer Res*, 64(10):3365-3370 (2004).
Takeshita, et al., "Efficient Delivery of Small Interfering RNA to Bone-Metastatic Tumors by Using Atelocollagen in Vivo." *Proceedings of the National Academy of Sciences of the United States of America*, 102(34):12177-12182 (2005).
Takeshita and Ochiya "Therapeutic Potential of RNA Interference against Cancer." *Cancer Sci*, 97(8):689-696 (2006).
Urban-Klein, et al., "RNAi-Mediated Gene-Targeting through Systemic Application of Polyethylenimine (Pei)-Complexed siRNA in Vivo." *Gene Ther*, 12(5):461-466 (2005).
Lorenzer, et al., "Going Beyond the Liver: Progress and Challenges of Targeted Delivery of SiRNA Therapeutics." *J Control Release*, 203:1-15 (2015).
Matilainen, et al., "Sphere Formation Reverses the Metastatic and Cancer Stem Cell Phenotype of the Murine Mammary Tumour 4T1, Independently of the Putative Cancer Stem Cell Marker Sca-1." *Cancer Lett*, 323(1):20-28 (2012).
Robinson, "RNAi Therapeutics: How Likely, How Soon?". *PLoS Biol*, 2(1):E28 (2004).
Santiago, et al., "Targeted Gene Knockout in Mammalian Cells by Using Engineered Zinc-Finger Nucleases." *Proc Natl Acad Sci U S A*, 105(15):5809-5814 (2008).
Takahagi, et al., "Production of Alpha 1,3-Galactosyltransferase Gene Knockout Pigs Expressing Both Human Decay-Accelerating Factor and N-Acetylglucosaminyltransferase III." *Mol Reprod Dev*, 71(3):331-338 (2005).
Zhang, et al., "Progress in MicroRNA Delivery." *J Control Release*, 172(3):962-974 (2013).
Bitko, et al. "Inhibition of respiratory viruses by nasally administered siRNA," *Nature Med.*, 11:50-55, 2005.
Heidel, et al. "Administration in non-human primates of escalating intravenous doses of targeted nanoparticles containing ribonucleotide reductase subunit M2 siRNA," *Proc. Natl. Acad. Sci. USA*, 104:5715-5721, 2007.
Li, et al. "Using siRNA in prophylactic and therapeutic regimens against SARS coronavirus in Rhesus macaque," *Nature Med.*, 11: 944-951, 2005.
Morrissey, et al. "Potent and persistent in vivo anti-HBV activity of chemically modified siRNAs," *Nature Biotech.*,23: 1002-1007, 2005.
Niu, et al. "Inhibition of HPV 16 E6 oncogene expression by RNA interference in vitro and in vivo," *Int. J. Gynecol. Cancer*, 16:743-751, 2006.
Rozema, et al. "Dynamic PolyConjugates for targeted in vivo delivery of siRNA to hepatocytes," *Proc. Natl. Acad. Sci. USA*, 104: 12982-12987, 2007.
Song, et al. "RNA interference targeting Fas protects mice from fulminant hepatitis," *Nature Med.*, 9:347-351, 2003.
Soutschek, et al. "Therapeutic silencing of an endogenous gene by systemic administration of modified siRNAs," *Nature*, 432: 173-17, 2004.
Wolfrum, et al., "Mechanisms and Optimization of in Vivo Delivery of Lipophilic siRNAs." *Nat Biotechnol*, 25(10):1149-1157 (2007).
Zimmermann, et al., "RNAi-mediated gene silencing in non-human primates," *Nature*, 441: 111-114, 2006.
Day, et al., "Preclinical Mouse Cancer Models: A Maze of Opportunities and Challenges." *Cell*, 163(1):39-53 (2015).
Park, et al., "Degradable Polyethylenimine-Alt-Poly(Ethylene Glycol) Copolymers as Novel Gene Carriers." *J Control Release*, 105(3):367-380 (2005).
Yano, et al., "Antitumor Activity of Small Interfering RNA/Cationic Liposome Complex in Mouse Models of Cancer." *Clin Cancer Res*, 10(22):7721-7726 (2004).
Coleman and Rubens "The Clinical Course of Bone Metastases from Breast Cancer." *Br J Cancer*, 55(1):61-66 (1987).
Fracasso, et al., "Phase I Study of Docetaxel in Combination with the P-Glycoprotein Inhibitor, Zosuquidar, in Resistant Malignancies." *Clin Cancer Res*, 10(21):7220-7228 (2004).
Huang, et al., "Identification of Candidate Molecular Markers Predicting Sensitivity in Solid Tumors to Dasatinib: Rationale for Patient Selection." *Cancer Res*, 67(5):2226-2238 (2007).
Lee, et al., "Astrocyte Elevated Gene-1 Activates Cell Survival Pathways through Pi3k-Akt Signaling." *Oncogene*, 27(8):1114-1121 (2008).
Mayo and Baldwin "The Transcription Factor NF-Kappab: Control of Oncogenesis and Cancer Therapy Resistance." *Biochim Biophys Acta*, 1470(2):M55-62 (2000).
Pinkel, et al., "High Resolution Analysis of DNA Copy Number Variation Using Comparative Genomic Hybridization to Microarrays." *Nat Genet*, 20(2):207-211 (1998).
Shaffer, et al., "Circulating Tumor Cell Analysis in Patients with Progressive Castration-Resistant Prostate Cancer." *Clin Cancer Res*, 13(7):2023-2029 (2007).
Wang, et al., "Amplification of Chromosome 8q22 and Metastasis of Breast Cancers." Abstract. Proceedings of the American Association for Cancer Research Annual Meeting, Apr. 2005. 47:1009 abstract (2006).
Brown, et al., "Estimating Health Care Costs Related to Cancer Treatment from Seer-Medicare Data." *Med Care*, 40(8 Suppl):IV-104-117 (2002).
Frank, et al. "Comparison of Methods for Extracting DNA from Formalin-Fixed Paraffin Sections for Nonisotopic PCR." *Diagn Mol Pathol*, 5(3):220-224 (1996).
Jemal, et al., "Cancer Statistics, 2005." *CA Cancer J Clin*, 55(1):10-30 (2005).
Kang, et al., "Breast Cancer Bone Metastasis Mediated by the SMAD Tumor Suppressor Pathway." *Proc Natl Acad Sci USA*, 102(39):13909-13914 (2005c).
Ponomarev, et al., "A Novel Triple-Modality Reporter Gene for Whole-Body Fluorescent, Bioluminescent, and Nuclear Noninvasive Imaging." *Eur JNuclMed Mol Imaging*, 31(5):740-751 (2004).
Kwong and Chin "The Metastasis Problem Gets Stickier." *Cancer Cell*, 15(1):1-2 (2009).
Adler, et al., "Genetic regulators of large-scale transcriptional signatures in cancer." *Nat Genet* 38:421-30 (2006).
Chang, et al., "Gene expression profiling for the prediction of therapeutic response to docetaxel in patients with breast cancer." *Lancet* 362:362-9 (2003).

(56) References Cited

OTHER PUBLICATIONS

Hamaguchi, et al., "DBC2, a candidate for a tumor suppressor gene involved in breast cancer." *Proc Natl Acad Sci U S A* 99:13647-52 (2002).

Hannemann, et al., "Changes in gene expression associated with response to neoadjuvant chemotherapy in breast cancer." *J Clin Oncol* 23:3331-42 (2005).

Kang, & Massague, "Epithelial-mesenchymal transitions: twist in development and metastasis." *Cell* 118:277-9 (2004).

Li, et al., "Oncogenic properties of PPM1D located within a breast cancer amplification epicenter at I7q23." *Nat Genet* 31:133-4 (2002).

Lucito, et al., "Detecting gene copy number fluctuations in rumor cells by microarray analysis of genornic representations." *Genome Res* 10:1726-36 (2000).

Mu, et al., "Genomic amplification and oncogenic properties of the KCNK9 potassium channel gene." *Cancer Cell* 3:297-302 (2003).

Pei, et al., PRC17, a novel oncogene encoding a Rab GTPase-activatihg protein, is amplified in prostate cancer. *Cancer Res* 62:5420-4 (2002).

Ye, et al., "Predicting hepatitis B virus-positive metastatic hepatocellular carcinomas using gene expression profiling and supervised machine learning." *Nat Med* 9:416-23 (2003).

METHODS OF IDENTIFYING AND TREATING POOR-PROGNOSIS CANCERS

CROSS-REFERENCE TO RELATED APPLICATIONS

The present application is a Continuation Application of U.S. application Ser. No. 15/901,174, filed Feb. 21, 2018, pending, which is Continuation Application of U.S. application Ser. No. 15/004,706, filed Jan. 22, 2016, now U.S. Pat. No. 9,932,587, issued 4-3-2018, which is a Continuation Application of U.S. application Ser. No. 14/619,977, filed Jan. 15, 2015, now abandoned, which is a Continuation Application of U.S. application Ser. No. 12/215,998, filed on Jun. 30, 2008, now abandoned, which claims the benefit of U.S. Provisional Application No. 60/937,789, filed on Jun. 28, 2007, which are incorporated herein by reference.

GOVERNMENT SUPPORT

This invention was made with government support under Grant No. W81XWH-06-1-0481 awarded by the United States Army. The government has certain rights in the invention.

FIELD OF THE INVENTION

The present invention relates generally to methods for identifying breast cancer patients with a poor prognosis, and to therapeutic modalities for improving prognosis by combating metastasis and abrogating chemoresistance in cancer cells.

BACKGROUND

The progression of cancer from an abnormal outgrowth to a life-threatening metastatic tumor is accompanied by a myriad of genetic and epigenetic alterations accumulated along the way. The challenge of distinguishing crucial drivers of metastasis from thousands of by-stander alterations remains a major obstacle in the battle against cancer. The turn of the century has witnessed the advent of two parallel, but individually incomplete, genomic approaches to unravel the genetics of cancer metastasis.

The first, based on comparative analyses of expression profiles of cancer cell line variants with different metastasis potentials, often obtained by in vivo selection in animal models, has led to the identification of several metastasis genes. However, much work remains to be done to validate the clinical relevance of metastasis genes identified in animal model studies.

The second approach, gene expression profiling of human tumor specimens, has enabled the identification of several poor-prognosis signatures that are predictive of recurrence and metastasis risk in human cancers. Although different poor-prognosis signatures for the same type of cancer identified in independent studies have proven to be operationally interchangeable for class prediction purposes in the clinic, the lack of gene overlap between different poor-prognosis signatures has posed a major challenge for understanding the biological underpinnings of cancer progression and metastasis, thereby hindering the development of targeted therapeutics. In other words, there is evidently no such thing as a universal "poor prognosis gene." There is therefore a need to identify a gene signature that predicts poor prognosis across clinical classes.

SUMMARY OF THE INVENTION

Embodiments of the present invention provide an objective means of prognostication regarding the long-term outcome of an incident of cancer. In a preferred embodiment, the invention relates to breast cancer. In other embodiments, the invention relates to immunotherapy and anti-sense therapy to combat metastasis in cancer, and to inhibit the development of cells that are resistant to chemotherapeutic agents.

In one embodiment, the invention provides a method of treating breast cancer or other cancer comprising: a) providing; i) a subject suspected of having breast cancer or other cancer, ii) an agent that inhibits an activity of metadherin, and b) administering said agent to said subject.

The method may be used when the breast cancer or other cancer is a poor prognosis cancer, including a metastatic cancer, a chemoresistant cancer, a cancer having in it a cell that has more than 2 copies of a metadherin gene, or a cancer having in it a cell that has a metadherin gene copy number greater than that of a control cell, which control cell may be a non-cancerous cell from the subject or from a reference subject, or from a breast cancer cell or other cancer cell from the reference subject.

In some embodiments, the agent may be selected from the group consisting of an antibody to metadherin, a metadherin antisense molecule, and a small molecule.

In a preferred embodiment, the invention provides a method for making prognosis for a subject with breast cancer or other cancer. The method comprises a) providing a cancer cell from said subject, b) determining, for said cell, a metadherin gene copy number, and c) assigning a poor prognosis to said subject if said copy number is greater than 2.

In one embodiment, the invention provides a method of reducing the development of chemoresistant cancer cells in a subject treated with a chemotherapeutic agent, the method comprising: a) administering to said subject a pharmaceutically acceptable amount of said chemotherapeutic agent, and b) administering to said subject an agent selected from the group consisting of an antibody to metadherin, a metadherin antisense molecule, and a small molecule.

In another embodiment, the invention provides a method of determining variations in the copy-number of a gene across defined populations comprising the following steps:
a) calculating an expression score based on expression differences between comparison groups for each of a plurality of genes having a genomic position on a chromosome,
b) ordering said expression scores based on said genomic position of each said gene,
c) finding and quantifying an expression pattern for each said gene by calculating a neighborhood score for each genomic locus using a geometry-weighted sum of expression scores for all the genes on the chromosome,
d) assigning a weight to each expression score based on the proximity of each gene to the locus in consideration,
e) estimating the statistical significance of the neighborhood score, and
f) identifying a region of potential copy number alteration.

In one embodiment, the method of determining variations in the copy-number of a gene across defined populations includes finding a stretch of 20 or more continuous aberrant neighborhood scores to detect a genomic copy number alteration.

In one embodiment, the method of determining variations in the copy-number of a gene across defined populations includes finding a neighborhood score greater than zero to detect a genomic gain.

In one embodiment, the method of determining variations in the copy-number of a gene across defined populations includes finding a neighborhood score less than zero to detect a genomic loss.

In some embodiments, the invention provides a method of treatment wherein the treatment agent is a combination of a known chemotherapeutic agent and an antibody that binds to metadherin, or an antisense molecule (which may be, without limitation, an shRNA or an siRNA) or a small molecule. In one embodiment the treatment agent is co-administered with the chemotherapeutic agent. In another embodiment, the treatment agent is conjugated to the chemotherapeutic agent. In one embodiment, the chemotherapeutic agent is paclitaxel.

In another embodiment, the invention provides a method of screening for anti-metastatic compounds comprising a) contacting a cancer cell expressing metadherin with a test compound; and b) determining the likelihood of said cancer cell to metastasize based on the level of biological activity of metadherin in the presence of said test compound relative to the level in the absence of said test compound. In one embodiment, the metadherin-expressing cancer cell is in an organism, which may be a human or a non-human mammal.

In one embodiment, the invention provides a method of determining, based on the copy number of the gene that encodes metadherin in a cell of a cancer, a subject's probability of surviving that cancer.

In one embodiment, the copy number is determined in situ. In another embodiment, the copy number is determined in vitro. In alternative embodiments, the copy number is determined by fluorescent in situ hybridization ("FISH"), comparative genomic hybridization (CGH), high density single nucleotide polymorphism (SNP) genotyping, or real-time PCR.

In still other embodiments, the invention uses the aforementioned antibodies in a method of treating a cancer susceptible to treatment with a chemotherapeutic agent in a subject. The method comprises (a) administering to the subject a pharmaceutically acceptable amount of the chemotherapeutic agent, and (b) administering also to the subject any of an agent that inhibits an activity of metadherin. In some embodiments, administering to the subject a pharmaceutically acceptable amount of the chemotherapeutic agent, and administering also the aforementioned agent provides a method of reducing the development of chemoresistant cancer cells in a subject treated with a chemotherapeutic agent.

In one embodiment, the invention provides a method of determining a prognosis in an individual with cancer, said cancers including but not limited to, liver cancer, prostate cancer, and brain cancer. In some embodiments, metadherin is aberrantly expressed in said cancers. In some embodiments, an antibody molecule specific for metadherin is adminstered to an individual at a sufficient dose such that metadherin is detected in said individual. Antibody mediated prognosis of cancer in human beings is well-known in the art, for example in U.S. Pat. No. 5,030,559 (herein incorporated by reference). In some embodiments, the invention provides a method of treating cancer by inhibing metadherin, said cancers including but not limited to liver cancer, prostate cancer, and brain cancer. In some embodiments, an antibody molecule specific for metadherin is administered to an individual with said cancer at a sufficient dose such the metadherin protein is inhibited or the amount of metadherin protein is reduced. It is not necessary that there be complete inhibition or reduction of metadherin protein, for the present application it is sufficient for there to be some inhibition or reduction. Antibody treatment of human beings with cancer is well-known in the art, for example in U.S. Pat. No. 5,736,137 (herein incorporated by reference).

In some embodiments, an antisense molecule capable of recognizing and binding metadherin RNA (including but not limited to mRNA and non-spliced RNA) is administered to an individual with said cancer at a sufficient dose such that metadherin RNA is inhibited or the amount of metadherin is reduced. In some embodiments, said anti-sense molecule is an siRNA, shRNA, and/or RNAi molecule. It is not necessary that there be complete inhibition or reduction, for the present application it is sufficient for there to be some inhibition or reduction. Anti-sense treatment of human beings with cancer is well-known in the art, for example U.S. Pat. No. 7,273,855 (herein incorporated by reference).

Definitions

To facilitate the understanding of this invention a number of terms (set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

The phrase "chosen from A, B, and C" as used herein, means selecting one or more of A, B, C.

As used herein, absent an express indication to the contrary, the term "or" when used in the expression "A or B," where A and B refer to a composition, disease, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that only the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

A number of terms herein relate to cancer. "Cancer" is intended herein to encompass all forms of abnormal or improperly regulated reproduction of cells in a subject. "Subject" and "patient" are used herein interchangeably, and a subject may be any mammal but is preferably a human. A "reference subject" herein refers to an individual who does not have cancer. The "reference subject" thereby provides a basis to which another cell (for example a cancer cell) can be compared.).

The growth of cancer cells ("growth" herein referring generally to cell division but also to the growth in size of masses of cells) is characteristically uncontrolled or inadequately controlled, as is the death ("apoptosis") of such cells. Local accumulations of such cells result in a tumor. More broadly, and still denoting "tumors" herein are accumulations ranging from a cluster of lymphocytes at a site of infection to vascularized overgrowths, both benign and malignant. A "malignant" tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel wells to enter ("intravasate") and exit ("extravasate") blood vessels. Tumors capable of releasing such cells are also referred to herein as "metastatic." The term is used herein also to denote any cell in such a tumor that is capable of such travel, or that is en route, or that has established a foothold in a target tissue. For example, a metastatic breast cancer cell that has taken root in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein.

Primary tumors are thought to derive from a benign or normal cell through a process referred to herein as "cancer progression." According to this view, the transformation of a normal cell to a cancer cell requires changes (usually many of them) in the cell's biochemistry. The changes are reflected clinically as the disease progresses through stages. Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain ("genomic gain") or lose ("genomic loss") genes, typically because an extra copy of an entire chromosome appears ("trisomy") or a region of a chromosome replicates itself ("genomic gain"

or, in some cases, "genomic amplification") or drops out when the cell divides. Thus, the "copy number" of a gene or a set of genes, largely invariant among normal cells, is likely to change in cancer cells (referred to herein as a "genomic event"), which affects the total expression of the gene or gene set and the biological behavior ("phenotype") of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes that govern the inheritance of genes in successive generations of cells or individuals.

It is thought that the emergence of metastatic cells entails its own distinct progression, referred to herein as "metastatic progression." The effect of disrupting a tumor on metastatic progression is unclear, but of interest because of "metastatic seeding," herein meaning a "surge" in metastasis that occurs, for example, when a tumor is surgically resected.

Certain regions of chromosomes, depending upon the specific type of cancer, have proven to be hot spots for genomic gain inasmuch as increases in copy number in the genomes of cells from multiple donors tend to occur in one or a few specific regions of a specific chromosome. Such hot spots are referred to herein as sites of "recurrent genomic gain." The term is to be distinguished from "recurrent cancer," which refers to types of cancer that are likely to recur after an initial course of therapy, resulting in a "relapse."

The term "prognosis," as used herein, relates to predictions regarding the long-term survival of cancer patients. In some contexts, the term may be used in connection with classifying various types of cancer (e.g., likelihood of recurrence; likelihood of metastasis). In some contexts, the term may be used in classifying particular patients suffering from a particular clinical type of cancer. For example, two patients having clinically identical forms of breast cancer may nevertheless not share the same prognosis with respect to the likelihood of recurrence or the likelihood of metastasis. "Prognosis" may also be determined by the tendency of a cancer (either by clinical type or within a particular patient) to resist or develop resistance to pharmaceuticals used to kill cancer cells or arrest their growth. Such drugs, referred herein as "chemotherapeutic" agents, include without limitation doxorubicin and paclitaxel. Cancer cells susceptible to one or another of these agents tend to adapt to the presence of chemotherapeutic agents by becoming "chemoresistant." Different cancers (by clinical type and within a given patient) vary in this respect. Thus, prognosis is also a function of chemoresistance. Mechanisms of chemoresistance are incompletely understood and need not be understood to practice embodiments of the instant invention. In general, however, the rate at which a cell takes in a drug ("drug uptake") and the extent to which a cell retains it ("drug retention"), contribute to a cell's tendency to resist being compromised by the drug.

A number of terms herein relate to methods that enable the practitioner to examine many distinct genes at once. By these methods, sets of genes ("gene sets") have been identified wherein each set has biologically relevant and distinctive properties as a set. Devices (which may be referred to herein as "platforms") in which each gene in a significant part of an entire genome is isolated and arranged in an array of spots, each spot having its own "address," enable one to detect, quantitatively, many thousands of the genes in a cell. More precisely, these "microarrays" typically detect expressed genes (an "expressed" gene is one that is actively transmitting its unique biochemical signal to the cell in which the gene resides). Microarray data, inasmuch as they display the expression of many genes at once, permit the practitioner to view "gene expression profiles" in a cell and to compare those profiles cell-to-cell to perform so-called "comparative analyses of expression profiles." Such microarray-based "expression data" are capable of identifying genes that are "overexpressed" (or underexpressed) in, for example, a disease condition. An overexpressed gene may be referred to herein as having a high "expression score."

The aforementioned methods for examining gene sets employ a number of well-known methods in molecular biology, to which references are made herein. A gene is a heritable chemical code resident in, for example, a cell, virus, or bacteriophage that an organism reads (decodes, decrypts, transcribes) as a template for ordering the structures of biomolecules that an organism synthesizes to impart regulated function to the organism. Chemically, a gene is a heteropolymer comprised of subunits ("nucleotides") arranged in a specific sequence. In cells, such heteropolymers are deoxynucleic acids ("DNA") or ribonucleic acids ("RNA"). DNA forms long strands. Characteristically, these strands occur in pairs. The first member of a pair is not identical in nucleotide sequence to the second strand, but complementary. The tendency of a first strand to bind in this way to a complementary second strand (the two strands are said to "anneal" or "hybridize"), together with the tendency of individual nucleotides to line up against a single strand in a complementarily ordered manner accounts for the replication of DNA.

Experimentally, nucleotide sequences selected for their complementarity can be made to anneal to a strand of DNA containing one or more genes. A single such sequence can be employed to identify the presence of a particular gene by attaching itself to the gene. This so-called "probe" sequence is adapted to carry with it a "marker" that the investigator can readily detect as evidence that the probe struck a target. As used herein, the term "marker" relates to any surrogate the artisan may use to "observe" an event or condition that is difficult or impossible to detect directly. In some contexts herein, the marker is said to "target" the condition or event. In other contexts, the condition or event is referred to as the target for the marker. Sequences used as probes may be quite small (e.g., "oligonucleotides" of <20 nucleotides) or quite large (e.g., a sequence of 100,000 nucleotides in DNA from a "bacterial artificial chromosome" or "BAC"). A BAC is a bacterial chromosome (or a portion thereof) with a "foreign" (typically, human) DNA fragment inserted in it. BACs are employed in a technique referred to herein as "fluorescence in situ hybridization" or "FISH." A BAC or a portion of a BAC is constructed that has (1) a sequence complementary to a region of interest on a chromosome and (2) a marker whose presence is discernible by fluorescence. The chromosomes of a cell or a tissue are isolated (on a glass slide, for example) and treated with the BAC construct. Excess construct is washed away and the chromosomes examined microscopically to find chromosomes or, more particularly, identifiable regions of chromosomes that fluoresce.

Alternatively, such sequences can be delivered in pairs selected to hybridize with two specific sequences that bracket a gene sequence. A complementary strand of DNA then forms between the "primer pair." In one well-known method, the "polymerase chain reaction" or "PCR," the formation of complementary strands can be made to occur repeatedly in an exponential amplification. A specific nucleotide sequence so amplified is referred to herein as the "amplicon" of that sequence. "Quantitative PCR" or "qPCR" herein refers to a version of the method that allows the artisan not only to detect the presence of a specific nucleic acid sequence but also to quantify how many copies of the sequence are present in a sample, at least relative to a control. As used herein, "qRTPCR" may refer to "quantitative real-time PCR," used interchangeably with "qPCR" as a technique for quantifying the amount of a specific DNA sequence in a sample. However, if the context so admits, the same abbreviation may refer to "quantitative reverse transcriptase PCR," a method for determining the amount of messenger RNA present in a sample. Since the presence of a particular messenger RNA in a cell indicates that a specific gene is currently active (being expressed) in the cell, this quantitative technique finds use, for example, in gauging the level of expression of a gene.

Collectively, the genes of an organism constitute its genome. The term "genomic DNA" may refer herein to the entirety of an organism's DNA or to the entirety of the nucleotides comprising a single gene in an organism. A gene typically contains sequences of nucleotides devoted to coding ("exons"), and non-coding sequences that contribute in one way or another to the decoding process ("introns").

The term "gene" refers to a nucleic acid (e.g., DNA) comprising covalently linked nucleotide monomers arranged in a particular sequence that comprises a coding sequence necessary for the production of a polypeptide or precursor or RNA (e.g., tRNA, siRNA, rRNA, etc.). The polypeptide can be encoded by a full-length coding sequence or by any portion of the coding sequence so long as the desired activities or functional properties (e.g., enzymatic activity, ligand binding, signal transduction, etc.) of the full-length or fragment are retained. The term also encompasses the coding region together with the sequences located adjacent to the coding region on both the 5' and 3' ends, such that the gene corresponds to the length of the full-length mRNA (also referred to as "pre-mRNA," "nuclear RNA," or "primary transcript RNA") transcribed from it. The sequences that are located 5' of the coding region and are present on the mRNA are referred to as 5' untranslated sequences. The sequences that are located 3' or downstream of the coding region and that are present on the mRNA are referred to as 3' untranslated sequences. The term "gene" encompasses both cDNA (the coding region(s) only) and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

Encoding in DNA (and messenger RNA) is accomplished by 3-membered nucleotide sequences called "codons." Each codon encrypts an amino acid, and the sequence of codons encrypts the sequence of amino acids that identifies a particular protein. The code for a given gene is embedded in a (usually) much longer nucleotide sequence and is distinguishable to the cell's decoding system from the longer sequence by a "start codon" and a "stop" codon. The decoding system reads the sequence framed by these two codons (the so-called "open reading frame"). The readable code is transcribed into messenger RNA which itself comprises sites that ensure coherent translation of the code from nucleic acid to protein. In particular, the open reading frame is delimited by a so-called "translation initiation" codon and "translation termination" codon.

The term "metadherin gene" refers herein to the full-length metadherin nucleotide sequence (e.g., contained in SEQ ID NO: XX). However, it is also intended that the term encompass fragments of the metadherin sequence, and/or other domains within the full-length metadherin nucleotide sequence. Furthermore, the terms "metadherin nucleotide sequence" or "Metadherin polynucleotide sequence" encompasses DNA, cDNA, and RNA (e.g., mRNA) sequences.

The term "plasmid" as used herein, refers to a small, independently replicating, piece of DNA. Similarly, the term "naked plasmid" refers to plasmid DNA devoid of extraneous material typically used to effect transfection. As used herein, a "naked plasmid" refers to a plasmid substantially free of calcium-phosphate, DEAE-dextran, liposomes, and/or polyamines. As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame (i.e., in an arrangement that the cell can transcribe as a single mRNA molecule) with an existing gene. The fusion partner may act as a reporter (e.g., βgal) or may provide a tool for isolation purposes (e.g., GST).

Where an amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is the variant most frequently observed in a population and is thus arbitrarily designed the "normal" or "wild-type" form of the gene In contrast, the terms "modified," "mutant," and "variant" (when the context so admits) refer to a gene or gene product that displays modifications in sequence and or functional properties (i.e., altered characteristics) when compared to the wild-type gene or gene product. In some embodiments, the modification comprises at least one nucleotide insertion, deletion, or substitution.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides.

As used herein, the term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2 PO_4 H_2 O$ and 1.85 g/l1 EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2 PO_4 H_2 O$ and 1.85 g/l1 EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2 PO_4 H_2 O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.*, 2: 482, 1981) by the homology alignment algorithm of Needleman and Wunsch (Needleman and Wunsch, *J. Mol. Biol.*, 48:443, 1970), by the search for similarity method of Pearson and Lipman (Pearson and Lipman, *Proc. Natl. Acad. Sci., U.S.A.*, 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., metadherin)

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is used herein in two different ways. A given gene typically appears in a genome once, on one chromosome. Since chromosomes in somatic cells of eukaryotes are in general paired, two copies or alleles of each gene are found. In some conditions, such as cancer, replication of chromosome pairs during cell division is disturbed so that multiple copies of a gene or chromosome accrue over successive generations. The pheonomenon is referred to generally (and herein) as "amplification."

In the context of molecular biological experimentation, the term is used differently. Experimentally, "amplification" is used in relation to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under the conditions in which they are used, will process only specific sequences of nucleic acids in a heterogeneous mixture of nucleic acids. In particular, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular metadherin sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. Nos. 4,683,195, 4,683,202, and 4,965,188, hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus one amino acid). In particularly preferred embodiments, the portion comprises the amino acid residues required for intermolecular binding of the compositions of the present invention with its various ligands and/or substrates.

As used herein the term "portion" when in reference to a protein (as in "a portion of a given protein") refers to fragments of that protein. The fragments may range in size from four consecutive amino acid residues to the entire amino acid sequence minus one amino acid As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA As used herein, the term "purified" refers to molecules (polynucleotides or polypeptides) that are separated from other components with which they are naturally associated. "To purify" refers to a reduction (preferably by at least 10%, more preferably by at least 50%, and most preferably by at least 90%) of one or more contaminants from a sample. For example, metadherin antibodies are purified by removal of contaminating non-immunoglobulin proteins; they are also purified by the removal of immunoglobulin that does not bind metadherin. The removal of non-immunoglobulin proteins and/or the removal of immunoglobulins that do not bind metadherin results in an increase in the percent of metadherin-reactive immunoglobulins in the sample. In another example, recombinant metadherin polypeptides are expressed in bacterial or other host cells and the polypeptides are purified by the removal of host cell proteins; the percent of recombinant metadherin polypeptides is thereby increased in the sample.

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences, that is the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies The terms "antigenic determinant" and "epitope" as used herein refer to that portion of an antigen that makes contact with a particular antibody and/or T cell receptor. When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, the term "transgenic" refers to a cell or organism whose genome has been heritably altered by genetically engineering into the genome a gene ("transgene") not normally part of it or removing from it a gene ordinarily present (a "knockout" gene). The "transgene" or "foreign gene" may be placed into an organism by introducing it into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell in the sense that the foreign DNA will be passed on to daughter cells. The term encompasses transfections of foreign DNA into the cytoplasm only. In general, however, the foreign DNA reaches the nucleus of the transfected cell and persists there for several days. During this time the foreign DNA is subject to the regulatory controls that govern the expression of endogenous genes in the chromosomes. The term "transient transfectant" refers to cells that have taken up foreign DNA but have failed to integrate this DNA. The term "transient transfection" encompasses transfection of foreign DNA into the cytoplasm only The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding metadherin or fragments thereof may be employed as hybridization probes. In this case, the metadherin-encoding polynucleotide sequences are typically employed in an aqueous solution containing salts (e.g., NaCl), detergents (e.g., SDS), and other components (e.g., Denhardt's solution, dry milk, salmon sperm DNA, etc.).

The terms "N-terminus" "$NH_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon).

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or $F(ab)_2$ fragments. The term "reactive" when used in reference to an antibody indicates that the antibody is capable of binding an antigen of interest. For example, a metadherin antibody is an antibody which binds to metadherin or to a fragment of metadherin.

The terms "auto-antibody" or "auto-antibodies" refer to any immunoglobulin that binds specifically to an antigen that is native to the host organism that produced the antibody (i.e., the antigen is not synthetic and/or has not been artificially supplied to the host organism). However, the term encompasses antibodies originally produced in response to the administration or presence of a foreign and/or synthetic substance in the host, but also cross-react with "self" antigens. Exemplary auto-antibodies include, without limitation, anti-cholesterol ester transfer protein (CETP) antibody, anti-major histocompatibility complex class II antibody, anti-cytokine antibody, and anti amyloid-β-peptide antibody. The presence of auto-antibodies is termed "autoimmunity."

The term "cytokine" refers to a molecule, such a protein or glycoprotein, involved in the regulation of cellular proliferation and function. Cytokines are exemplified by lymphokines (e.g., tumor necrosis factor-α, tumor necrosis factor-β, interferon-γ, etc.), growth-factors (e.g., erythropoietin, insulin, G-CSF, M-CSF, GM-CSF, EGF, PDGF, FGF, etc.), and interleukins (e.g., IL-2, IL-4, IL-5, IL-6, IL-9, IL-10, IL-13, etc.)

The term "B cell epitope" as used herein refers to an antigenic determinant (protein or carbohydrate) to which a single antibody molecule binds. B cell epitopes may comprise linear epitopes (amino acids adjacent to each other in the primary sequence) or conformational epitopes (moieties distant from each other in the primary sequence, but which are brought in proximity to one another during folding of the antigen) of at least four amino acid residues.

The term "T cell epitope" as used herein refers to an antigenic determinant presented by a MHC class I or class II molecule for binding to a single T cell receptor. T cell epitopes are linear epitopes comprising at least seven amino acid residues. In some embodiments of the present invention, the term T cell epitope comprises a T helper cell epitope which is an antigen fragment presented by an MHC class II molecule for binding to T cell receptor on the surface of a helper T cell (e.g., generally $CD4^+$).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.

The terms "antigen," "immunogen," "antigenic," "immunogenic," "antigenically active," and "immunologically active" refer to any substance that is capable of inducing a specific humoral and/or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

A peptide sequence and nucleotide sequence may be "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro The terms "oligosaccharide" and "OS" antigen refer to a carbohydrate comprising up to ten component sugars, either O or N linked to the next sugar. Likewise, the terms "polysaccharide" and "PS" antigen refer to polymers of more than ten monosaccharide residues linked glycosidically in branched or unbranched chains As used herein, the term "mammalian sequence" refers to synthetic, recombinant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid β-peptide sequences.

The terms "mammals" and "mammalian" refer animals of the class mammalia which nourish their young by fluid secreted from mammary glands of the mother, including human beings. The class "mammalian" includes placental animals, marsupial animals, and monotremal animals. An exemplary "mammal" may be a rodent, primate (including simian and human) ovine, bovine, ruminant, lagomorph, porcine, caprine, equine, canine, feline, ave, etc. Preferred non-human animals are selected from the order Rodentia.

Preferred embodiments of the present invention are primarily directed to vertebrate (backbone or notochord) members of the animal kingdom.

The terms "patient" and "subject" refer to a mammal that may be treated using the methods of the present invention.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that which receives a mock treatment (e.g., saline alone or metadherin without a heterologous antigen insert or conjugate).

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when injected together with an antigen, non-specifically enhances the immune response to that antigen. Exemplary adjuvants include but are not limited to incomplete Freunds adjuvant (IFA), aluminum-based adjuvants (e.g., AIOH, AIPO4, etc), and Montanide ISA 720.

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance (e.g., Metadherin vaccine) is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, antioxidants exemplified by ascorbic acid and glutathione, and hydrolyzed proteins.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "C-terminal portion," "COOH-terminal portion," "carboxy terminal portion," "C-terminal domain,"

"COOH-terminal domain," and "carboxy terminal domain," when used in reference to an amino acid sequence of interest (such as metadherin) refer to the amino acid sequence (and portions thereof that is located from approximately the middle of the amino acid sequence of interest to the C-terminal-most amino acid residue of the sequence of interest. The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.). refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

For example, the term "has the biological activity of a specifically named protein" (such as "metadherin") when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence (such as a sequence encoding metadherin) includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence (such as a sequence encoding Metadherin, a sequence encoding GSHcAg, and a sequence encoding HBcAg, etc.) is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

Exons, introns, genes and entire gene-sets are characteristically locatable with respect to one another. That is, they have generally invariant "genomic loci" or "genomic positions." Genes distributed across one or several chromosomes can be mapped to specific locations on specific chromosomes. The field of "cytogenetics" addresses several aspects of gene mapping. First, optical microscopy reveals features of chromosomes that are useful as addresses for genes. In humans, chromosomes are morphologically distinguishable from one another and each (except for the Y-chromosome) has two distinct arms separated by a "centromere." Each arm has distinctive "bands" occupied by specific genes. Metadherin, for example, a gene of particular interest herein, is located on the long arm ("q") of chromosome 8 in band 22. Disease-related changes in chromosome number, and changes in banding form the basis for diagnosing a number of diseases. "Microdissection" of chromosomes and DNA analysis of the microdissected fragments have connected specific DNA sequences to specific locations on chromosomes. In cancer, a region of a chromosome may duplicate or amplify itself or drop out entirely. FISH, mentioned above, and "comparative genomic hybridization" ("CGH") have extended the reach of cytogenetic analysis to the extent of measuring genome alterations within and between individuals. CGH, for example, in which chromosomes from a normal cell are hybridized with a corresponding preparation from a cancer cell provides a means of directly determining cancer-related differences in copy number of chromosomal regions.

A number of terms used herein relate to antibodies. Antibodies are globular proteins produced by cells of the immune system ("immunoglobulins"). A population of antibodies that all arose from one cell and its progeny is a "monoclonal antibody." Others are "polyclonal." Antibodies bind antigens. Antigens are compositions to which an immune system has adapted by acquiring the ability to synthesize an immunoglobulin that specifically binds to a given antigen in the sense that a "bound" antigen is no longer thermodynamically free in solution. Fragments of an antibody are capable of binding a (specific) antigen, and such fragments (e.g., Fv, Fab, Fab' and F(ab')$_2$) may be used in embodiments of the invention. Monoclonal antibodies are preferably produced in cells maintained and reproduced in vitro. Such cells are preferably hybridomas. Methods well known in the art are used to create hybridoma cells, a characteristic of which is to secrete a specific monoclonal antibody in quantity. Briefly, to create a hybridoma cell line (a "cell line" herein is any collection of cells proliferated in vitro), a mammal is immunized with the antigenic composition bound to a carrier. The carrier (e.g., protein, peptide, such as serum albumin or gamma globulin obtained from the mammal) is not recognized as a foreign molecule to the mammal. Preferably, however, the carrier is an antibody produced by the mammal. The carrier antibody can bind the hapten, but not with any specificity. Since the mammal produced the carrier antibody, the mammal will not necessarily recognize the carrier antibody as foreign and will likely produce antibodies having binding specificity only for the hapten. Splenocytes (typically) of the mammal are fused with immortalized cells to produce hybridomas and the hybridoma which produces a monoclonal antibody or antigen binding fragment thereof having the particular binding specificity for the hapten is selected. "Immortalized" cells herein are cells that reproduce indefinitely when cultured in vitro.

Monoclonal antibodies may be useful therapeutically in so-called "immunotherapy." Monoclonal antibodies typically are products of non-human cells and may therefore cause untoward immune responses when injected into human subjects. Methods of "humanizing" such antibodies are well-known in the art, however. In one method, the cells responsible for producing the antibody are genetically engineered to make and secrete a so-called "chimeric" protein.

A usually small portion of such a protein is a fragment of the monoclonal antibody and the rest is a human immunoglobulin. Chimeric proteins are a particular kind of "fusion protein." As used herein, any protein expressed by a gene (typically, a recombinant gene) comprising the genetic code for two or more generally independent proteins is a fusion protein.

Monoclonal antibodies also find use herein to detect particular cells, subcellular bodies, etc. by "immunostaining." The antibody delivers a stainable (or otherwise detectable) element to its antigenic determinant. Thus, monoclonal antibodies are useful diagnostically for a countless number of conditions, not the least of which is their use in determining genomic changes in cancer cells.

"Targeted therapeutics" is used herein to denote any therapeutic modality that affects only or primarily only the cells or tissues selected ("targeted") for treatment. A monoclonal antibody specific for an antigen expressed only by a target (if retained by the target) is highly useful in targeted therapeutics. In the case of unwanted cells such as cancer cells, if the antibody doesn't induce destruction of the target directly, it may do so indirectly by carrying to the target, for example, a agent coupled to the antibody. On the other hand, agents that suppress processes that tend to promote uncontrolled proliferation of cells ("antineoplastic agents") can be delivered to target sites in this manner.

The term "agent" is used herein in its broadest sense to refer to a composition of matter, a process or procedure, a device or apparatus employed to exert a particular effect. By way of non-limiting example, a surgical instrument may be employed by a practitioner as an "excising" agent to remove tissue from a subject; a chemical may be used as a pharmaceutical agent to remove, damage or neutralize the function of a tissue, etc. Such pharmaceutical agents are said to be "anticellular." Cells may be removed by an agent that promotes apoptosis. A variety of toxic agents, including other cells (e.g., cytotoxic T-cell lymphocytes) and their secretions, and a plethora of chemical species, can damage cells.

The term "by-stander", as used herein, refers to a process or event initiated or affected by another, causative event or process The term "class prediction", as used herein, refers to a method of making predictions about an individual outcome for an individual of a particular class based on historical outcomes in similarly classified individuals.

The term "Cox hazard ratios", as used herein, refers to a particular method of evaluating the probability of occurrence of an event associated with a hazardous condition as a function of the extent of exposure to the hazardous condition.

The term "knockdown", as used herein, refers to a method of selectively preventing the expression of a gene in an individual.

The term "oncogene", as used herein, refers to any gene that regulates a process affecting the suppression of abnormal proliferative events.

The term "integrative genomic analysis", as used herein, refers to any study of an individual's genome by analyzing data from at least two distinct methods of genomic analysis in combination.

The term "single nucleotide polymorphism" or "SNP", as used herein, refers to a DNA sequence variation occurring when a single nucleotide in the genome (or other shared sequence) differs between members of a species or between paired chromosomes in an individual. Single nucleotide polymorphisms may fall within coding sequences of genes, non-coding regions of genes, or in the intergenic regions between genes. Single nucleotide polymorphisms within a coding sequence will not necessarily change the amino acid sequence of the protein that is produced, due to degeneracy of the genetic code. A Single nucleotide polymorphism in which both forms lead to the same polypeptide sequence is termed synonymous (sometimes called a silent mutation)— if a different polypeptide sequence is produced they are non-synonymous. Single nucleotide polymorphisms that are not in protein-coding regions may still have consequences for gene splicing, transcription factor binding, or the sequence of non-coding RNA.

The term "algorithm", as used herein, refers to a step-by-step problem-solving procedure, especially an established, recursive computational procedure for solving a problem in a finite number of steps. The bioinformatics strategy referred to as "Analysis of CNAs by Expression data" (ACE) is one example of an algorithm that detects recurrent DNA copy number alterations (CNAs) that affect regional gene expression.

The term "tissue array" or "tissue microarray", as used herein, refers to high throughput platforms for the rapid analysis of protein, RNA, or DNA molecules. These arrays can be used to validate the clinical relevance of potential biological targets in the development of diagnostics, therapeutics and to study new disease markers and genes. Tissue arrays are suitable for genomics-based diagnostic and drug target discovery.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2): 244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "xenograft", as used herein, refers to the transfer or transplant of a cell(s) or tissue from one species to an unlike species (or genus or family).

The term "orthotopic" or "orthotopic xenograft", as used herein, refers to a cell or tissue transplant grafted into its normal place in the body.

The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro-dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

The term "data mining", as used herein, refers to the automated or convenient extraction of patterns representing knowledge implicitly stored or captured in large databases, data warehouses, internet websites, other massive information repositories, or data streams.

The terms "overexpress", "overexpressing" and grammatical equivalents, as used herein, refer to the production of a gene product at levels that exceed production in normal or control cells. The term "overexpression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Overexpression may likewise result in elevated levels of proteins encoded by said mRNAs.

The term "laser capture microdissection" or "LCM", as used herein, refers to a method for isolating specific cells of interest from tissue sections wherein a transparent transfer film is applied to the surface of a tissue section. A pulsed laser beam activates a precise spot on the transfer film, fusing the film with the underlying cells of choice. The transfer film with the bonded cells is then lifted off the thin tissue section, leaving all unwanted cells behind. This method is useful for collecting selected cells for DNA, RNA and/or protein analyses. LCM can be performed on a variety of tissue samples including blood smears, cytologic preparations, cultured cells and solid tissues.

The term "heatmap", as used herein, refers to a graphical representation of data where the values obtained from a variable two-dimensional map are represented as colors. As related to the field of molecular biology, heat maps typically represent the level of expression of multiple genes across a number of comparable samples as obtained from a microarray.

The term "phage display", as used herein, refers to the integration/ligation of numerous genetic sequences from a DNA library, consisting of all coding sequences of a cell, tissue or organism library into the genome of a bacteriophage (i.e. phage) for high-throughput screening protein-protein and/or protein-DNA interactions. Using a multiple cloning site, these fragments are inserted in all three possible reading frames to ensure that the cDNA is translated. DNA fragments are then expressed on the surface of the phage particle as part of it coat protein. The phage gene and insert DNA hybrid is then amplified by transforming bacterial cells (such as TG1 *E. coli* cells), to produce progeny phages that display the relevant protein fragment as part of their outer coat. By immobilizing relevant DNA or protein target(s) to the surface of a well, a phage that displays a protein that binds to one of those targets on its surface will remain while others are removed by washing. Those that remain can be eluted, used to produce more phage (by bacterial infection with helper phage) and so produce an enriched phage mixture. Phage eluted in the final step can be used to infect a suitable bacterial host, from which the phagemids can be collected and the relevant DNA sequence excised and sequenced to identify the relevant, interacting proteins or protein fragments.

The term "apoptosis", as used herein, refers to a form of programmed cell death in multicellular organisms that involves a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway have been implicated in diseases associated with uncontrolled cell proliferations, such as cancer.

The term "bioluminescence imaging" or "BLI", as used herein, refers to the noninvasive study of ongoing biological processes in living organisms (for example laboratory animals) using bioluminescence, the process of light emission in living organisms. Bioluminescence imaging utilizes native light emission from one of several organisms which bioluminescence. The three main sources are the North American firefly, the sea pansy (and related marine organisms), and bacteria like *Photorhabdus luminescens* and *Vibrio fischeri*. The DNA encoding the luminescent protein is incorporated into the laboratory animal either via a virus or by creating a transgenic animal. While the total amount of light emitted via bioluminescence is typically small and not detected by the human eye, an ultra-sensitive CCD camera can image bioluminescence from an external vantage point. Common applications of BLI include in vivo studies of infection (with bioluminescent pathogens), cancer progression (using a bioluminescent cancer cell line), and reconstitution kinetics (using bioluminescent stem cells).

The term "consensus region" or "consensus sequence", as used herein, refers to the conserved sequence motifs that show which nucleotide residues are conserved and which nucleotide residues are variable when comparing multiple DNA, RNA, or amino acid sequence alignments. When comparing the results of a multiple sequence alignment, where related sequences are compared to each other, and similar functional sequence motifs are found. The consensus sequence shows which residues are conserved (are always the same), and which residues are variable. A consensus sequence may be a short sequence of nucleotides, which is found several times in the genome and is thought to play the same role in its different locations. For example, many transcription factors recognize particular consensus sequences in the promoters of the genes they regulate. In the same way restriction enzymes usually have palindromic consensus sequences, usually corresponding to the site where they cut the DNA. Splice sites (sequences immediately surrounding the exon-intron boundaries) can also be considered as consensus sequences. In one aspect, a consensus sequence defines a putative DNA recognition site, obtained for example, by aligning all known examples of a certain recognition site and defined as the idealized sequence that represents the predominant base at each position. Related sites should not differ from the consensus sequence by more than a few substitutions.

The term "seminaphtharhodafluor", "SNARF" or "SNARF-1", as used herein, refers to a fluorescent dye that changes color with pH, and can be used to construct optical biosensors.

The term "linkage", or "genetic linkage," as used herein, refers to the phenomenon that particular genetic loci of genes are inherited jointly. The "linkage strength" refers to the probability of two genetic loci being inherited jointly. As the distance between genetic loci increases, the loci are more likely to be separated during inheritance, and thus linkage strength is weaker.

The term "neighborhood score", as used herein, refers to the relative value assigned to a genomic locus based on a geometry-weighted sum of expression scores of all the genes on a given chromosome, as a measurement of the copy number status of the locus. A positive neighborhood score is indicative of an increase in copy number, whereas a negative neighborhood score is indicative of a decrease in copy number.

The term "expression score", as used herein, refers to the expression differences (i.e., the level of transcription (RNA) or translation (protein)) between comparison groups on a given chromosome. The expression score for a given gene is calculated by correlating the level of expression of said gene with a phenotype in comparison. For example, an expression score may represent a comparison of the expression differences of a given gene in normal vs. abnormal conditions, such as parental vs. drug-resistant cell lines. As used herein, the term "regional expression score" refers to the expression score of gene(s) in proximity to the locus in consideration. Since linkage strength between genetic loci decreases (i.e. decays) as the distance between them increases, the "regional expression score" more accurately reflects the expression differences between comparison groups by assigning greater weight to the expression scores of genes in proximity to the locus in consideration.

The terms "geometry-weighted" or "geometry-weighted sum", as used herein, refers to the significance attached to a given value, for example an "expression score", based on physical position, including but not limited to genomic position. Since linkage strength between genetic loci decreases (i.e. decays) as the distance between them increases, the "weight" assigned to a given value is adjusted accordingly.

The term "copy number alteration" or "CNA", as used herein, refers to the increase (i.e. genomic gain) or decrease (i.e. genomic loss) in the number of copies of a gene at a specific locus of a chromosome as compared to the "normal" or "standard" number of copies of said gene that locus. As used herein, an increase in the number of copies of a given gene at a specific locus may also be referred to as an "amplification" or "genomic amplification" and should not be confused with the use of the term "amplification" as it relates, for example, to amplification of DNA or RNA in PCR and other experimental techniques.

The term "clonogenic assay", as used herein, refers to a technique for studying whether a given cancer therapy (for example drugs or radiation) can reduce the clonogenic survival and proliferation of tumor cells. While any type of cell may be used, human tumor cells are commonly used for oncological research. The term "clonogenic" refers to the fact that these cells are clones of one another.

The term "adjuvant therapy", as used herein, refers to additional treatment given after the primary treatment to increase the chances of a cure. In some instances, adjuvant therapy is administered after surgery where all detectable disease has been removed, but where there remains a statistical risk of relapse due to occult disease. If known disease is left behind following surgery, then further treatment is not technically "adjuvant". Adjuvant therapy may include chemotherapy, radiation therapy, hormone therapy, or biological therapy. For example, radiotherapy or chemotherapy is commonly given as adjuvant treatment after surgery for a breast cancer. Oncologists use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. Adjuvant chemotherapy and radiotherapy are often given following surgery for many types of cancer, including colon cancer, lung cancer, pancreatic cancer, breast cancer, prostate cancer, and some gynecological cancers.

The term "matched samples", as used herein, as for example "matched cancer samples" refers to a sample in which individual members of the sample are matched with every other sample by reference to a particular variable or quality other than the variable or quality immediately under investigation. Comparison of dissimilar groups based on specified characteristics is intended to reduce bias and the possible effects of other variables. Matching may be on an individual (matched pairs) or a group-wide basis.

The term "genomic segments", as used herein, refers to any defined part or region of a chromosome, and may contain zero, one or more genes.

The term "poor prognosis", as used herein, refers to a prospect of recovery from a disease, infection, or medical condition that is associated with a diminished likelihood of a positive outcome. In relation to a disease such as cancer, a "poor prognosis" may be associated with a reduced patient survival rate, reduced patient survival time, higher likelihood of metastatic progression of said cancer cells, and/or higher likelihood of chemoresistance of said cancer cells.

The term "chemoresistant", as used herein, refers to a cancer and/or tumor that is measurably less responsive to chemotherapeutic agents than other cancers and/or tumors.

The term "co-administer", as used herein, refers to the administration of two or more agents, drugs, and/or compounds together (i.e. at the same time).

The term "diagnose" or "diagnosis", as used herein, refers to the determination, recognition, or identification of the nature, cause, or manifestation of a condition based on signs, symptoms, and/or laboratory findings.

BRIEF DESCRIPTION OF THE DRAWINGS

For a more complete understanding of the features and advantages of the present invention, reference is now made to the detailed description of the invention along with the accompanying figures and tables.

Figure 1:
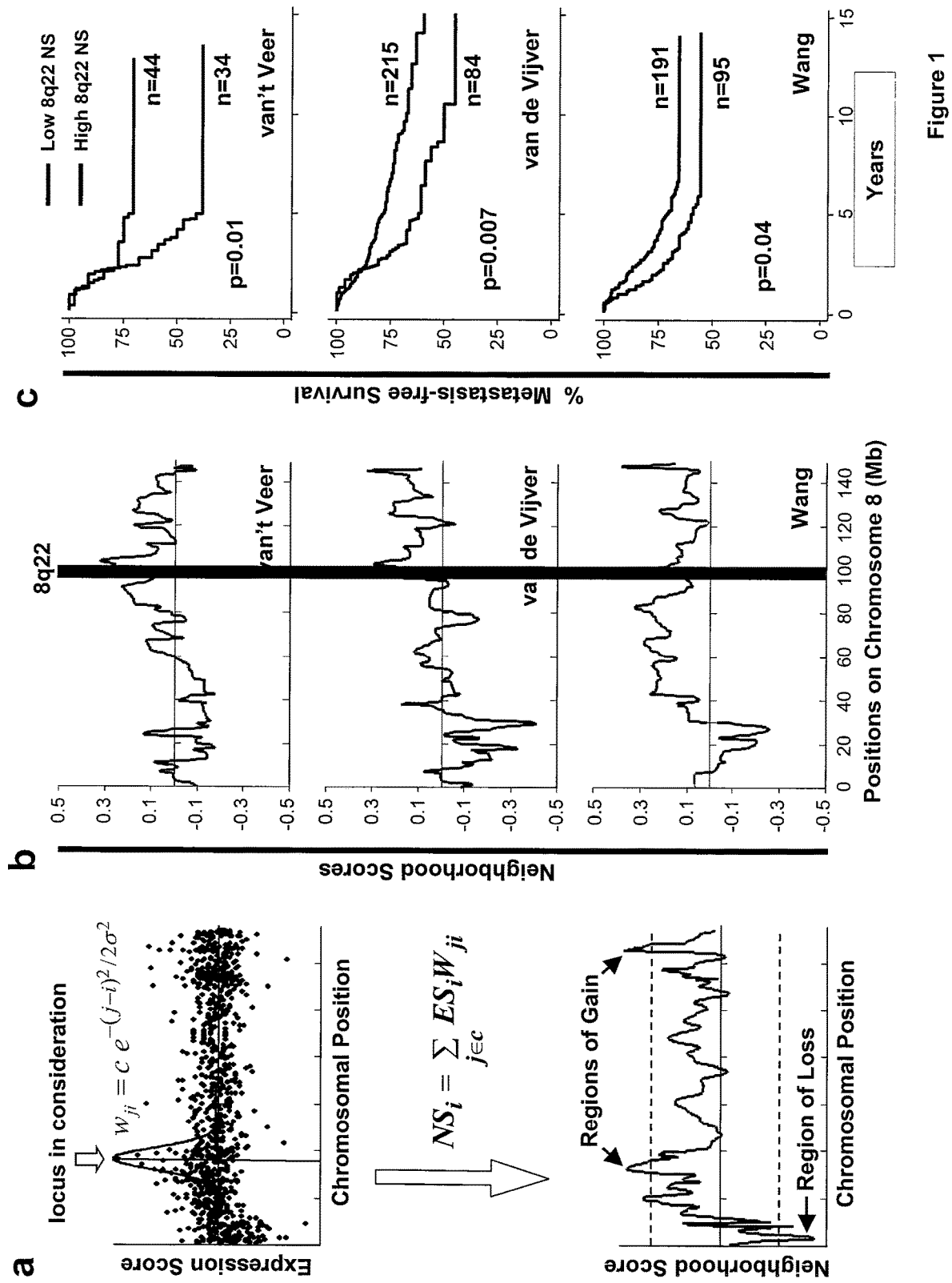
FIG. 1 depicts the use of ACE analysis to identify recurrent genomic gain at 8q22 in poor-prognosis breast cancer.

Table 1 depicts a recurrent region of gain associated with poor-prognosis breast cancer as detected by ACE. Only the regions detected in at least two of the three analyzed datasets are shown.

Table 2 depicts all poor-prognosis-associated CAN regions detected by ACE in breast cancer.

Table 3 depicts Cox hazard ratios for relapse based on neighborhood scores of each of the common regions of gain in the three published datasets.

Table 4 depicts regions detected by ACE in bladder tumors compared to normal samples.

Table 5 depicts genomic DNA copy number by qPCR, as well as the expression by qRT-PCR or immunostaining of the genes at 8q22 in human breast tumor samples.

Table 6 depicts patient records of tumors used in the breast cancer tissue array.

Table 7 depicts microarray data of the genes with altered expression after MTDH knockdown in LM2 cancer cells.

Table 8 shows Cox hazard ratios for metastasis in breast cancer based on MTDH expression levels in tissue array analysis.

Table 9 depicts the primers used in the qPCR for DNA copy number and gene expression analysis.

Table 10 lists chemotherapeutic agents.

DETAILED DESCRIPTION OF THE INVENTION

Recurrent DNA copy number alterations (CNAs) have been observed in a wide range of human cancers. Such genetic events often indicate the presence of key mediators of malignancy in the affected genomic loci. For example, elevated expression of oncogenes, such as c-Myc, CCND1, Her2 and EGFR1[22-26], often result from amplification of corresponding genomic segments. However, CNAs responsible for cancer metastasis are poorly characterized. Various techniques have been developed to detect genomic alterations, including fluorescence in situ hybridization (FISH), comparative genomic hybridization (CGH) and high-density single nucleotide polymorphism (SNP) genotyping[27-30]. Detection of CNAs by expression profiling analysis is theoretically possible since a strong correlation between genomic alterations and aberrant expression of genes in affected loci has been observed[31]. Accurate detection of CNAs using expression analysis, however, is technically difficult because gene expression data reflect multiple layers of gene regulation beyond genomic alterations. Such analysis is particularly challenging with clinical tumor samples due to the inherent heterogeneity of clinical specimens and the rampant genomic instability of late stage tumors.

Copy number is readily determined by any of several methods well-known in the art. Garcia et al. (U.S. Patent Application Publication 2008/0090233, incorporated herein in its entirety, with cited references, for all purposes) have utilized FISH in particular to evaluate copy number of the epidermal growth factor receptor in cells. The method described therein is readily adapted for metadherin by persons having ordinary skill in the art. Comparative genomic hybridization ("CGH"), described, for example, in U.S. Pat. No. 6,159,685 and related applications (also incorporated herein, with cited references, for all purposes), is another well-known method for determining the copy number of a gene. Together with the information disclosed herein, CGH is also readily adapted for use in determining the copy number of metadherin. A variety of methods based on PCR may also be adapted for the purpose. A non-limiting example is found in U.S. Pat. No. 6,180,349, incorporated herein in its entirety by reference, wherein real-time fluorescence PCR is employed to measure copy number. More recently, a method for quantifying gene copy number of individual genes, whole chromosomes or portions of chromosomes in a homogeneous reaction that does not require amplification of the target, resolution of fragment sizes, or microscopy has been described (U.S. Patent Application Publication 2007/0087345, incorporated herein in its entirety, with cited references, for all purposes).

In one embodiment, the present invention contemplates a computational algorithm termed "Analysis of CNAs by Expression data" (ACE) to identify a recurrent 8q22 genomic gain in poor-prognosis human cancers, and in particular poor prognosis breast cancer. The 8q22 locus harbors the metastasis gene Metadherin (MTDH; also called Lyric, AEG1[32-34]). Genomic gain of 8q22 and the concurrent overexpression of MTDH were observed in a significant proportion of human primary breast tumors and were associated with poor survival and a higher risk of metastatic progression. Functional characterization of MTDH in animal models and in vitro functional assays revealed its dual functions in promoting metastasis and chemoresistance of breast cancers. Inhibition (complete or partial) of MTDH expression in breast cancer cells reduced the cells' potential for metastasizing to lung and other organs, and sensitized the cells to stress and chemotherapeutic agents. Expression profiling of a highly metastatic human breast cancer cell line LM2 revealed an MTDH-regulated gene set that includes (but is not necessarily limited to) several genes involved in the regulation of chemosensitivity of cancer cells to a broad spectrum of antineoplastic agents. Among these genes, ALDH3A1 and Met were further confirmed to play a functional role in MTDH-mediated chemoresistance. Such results, properly integrated, uncover metastasis genes with important prognostic as well as therapeutic values, and establish MTDH as a major target for the prevention and treatment of chemoresistant metastasis.

In one embodiment, the present invention contemplates integrating such results by means of a computational approach to unveil functionally significant cytogenetic events directly linked to altered gene expression in poor-prognosis tumors. Reasoning that metastasis genes are likely to reside in these recurrent genomic alterations, the ACE algorithm is designed to translate gene expression profiling data into putative genomic alteration maps. The ACE approach has been validated in multiple datasets, regardless of the nature of samples or the platforms of gene expression microarrays. Even in the most complicated studies of cancer metastasis, where numerous genomic events make it difficult to detect phenotype-specific CNAs, ACE still produced reliable results that were validated with direct cytogenetic methods. In fact, ACE was able to take advantage of the heterogeneity of large, independent datasets to pinpoint the smallest and most conserved regions of overlap that were most likely to harbor critically important candidate metastasis genes. Although the genomic gain of different lengths near 8q22 is known to occur in breast cancer, the phenomenon had not been clearly associated with metastasis and poor prognosis. More importantly, the target gene of this amplification event had not been identified due to the large number of genes in this region. By analyzing multiple datasets, ACE successfully narrowed the cytogenetic event to a 13-gene region that allowed for focused functional testing of candidate genes in animal metastasis assays.

High-throughput genomic profiling methods such as CGH and SNP arrays have facilitated the recent discovery of several novel cancer genes[43, 53, 54]. As a new addition to the repertoire of integrative genomic analysis tools, ACE is particularly useful when cytogenetic data are not available. ACE can also be used as a complementary strategy to fine-map results obtained from cytogenetic analyses. A further advantage of ACE is that it can detect regional epigenetic alterations that cannot be discerned by the CGH or the SNP array approach (FIG. 2d). Additionally, ACE provides a direct link between cytogenetic events and gene activity changes, thereby facilitating the search for functionally important candidate genes. In contrast, genomic alterations detected by CGH or SNP array approaches may not necessarily result in altered gene expression. Given the large amount of archived gene expression data available in public domains and the difficulty in obtaining matched cancer samples, ACE is a useful data-mining tool to bring new insights into the functional mechanism of cancer progression.

ACE analysis of cancer, and in particular breast cancer, according to one embodiment of the invention, together with clinical and functional studies of MTDH, indicate that MTDH is a metastasis gene with prognostic potential and therapeutic value. Brown et al.[32] previously used phage display to identify MTDH as a homing receptor that mediates the adhesion of the 4T1 murine mammary tumor cell line to lung endothelial cells and also promotes lung metastasis. In that study, only the mouse 4T1 cell line and the biologically irrelevant HEK 293T cell line were used to analyze the lung-targeting function of MTDH. The involvement of MTDH in human cancer, however, has not been previously reported. In addition, no rigorous clinical correlation study has been performed to directly link MTDH to human cancer metastasis, and in particular human breast cancer metastasis.

An extensive collection of human breast tumor samples analyzed according to an embodiment of the invention demonstrated that an elevated MTDH protein level is an important prognostic factor independent of other clinicopathological factors. Results indicated that a substantial proportion of human breast tumors exhibit MTDH genomic amplification with a subsequent increase in MTDH expression, which is associated with poor survival and higher risk of progression.

The importance of MTDH in cancer metastasis is not necessarily limited to promoting lung-specific spread of breast tumor cells. Indeed, the functional importance of MTDH in systemic metastasis using a well-established model for human breast cancer metastasis was validated by one embodiment of the instant invention. Although MTDH was previously reported to enhance murine mammary tumor cell adhesion to lung endothelial cells, in this embodiment of the invention MTDH was also shown to enhance the affinity of human breast cancer cells for other endothelial cell types, consistent with its role in promoting systemic metastasis in animal models. Moreover, MTDH was aberrantly expressed in tumors from liver, prostate, and brain[55-57], suggesting a potential involvement in a broad spectrum of cancers.

Current standard treatments for cancer, and in particular breast cancer, use the combination of surgery to remove localized disease and chemotherapy to eliminate systemic spreading. However, relapsed cancers, including breast cancer, often acquire resistance to chemotherapy and are often inoperable. Thus, over 90% of breast cancer related deaths are not due to cancer at the primary site, but rather due to the spread of chemoresistant cancer cells from breast to secondary vital organs, such as lung, bone, liver and brain. Metastasis and chemoresistance remain two major obstacles to curative therapy. One embodiment of the present invention has identified MTDH as a factor in the chemoresistance of cancer cells. Thus, MTDH may be among an important class of genes that play a role both in metastasis and in chemoresistance (FIG. 14e). This duality may explain why some metastasis genes are selected for in the primary tumor: whether or not they confer a growth advantage (which they typically do not in animal tumorigenic assays), they presumably confer a survival advantage by endowing cancer cells with enhanced tolerance to therapeutic and physiological stresses that human tumors may endure. At the same time, other genes at 8q22, such as SDC2 and CCNE2, may confer the growth advantage and allow for the expansion of tumor cells with 8q22 genomic gain in the primary tumor. Physical linkage of growth-promoting and metastasis-driving genes in 8q22 may thus produce cascading events for the expansion of the primary tumor followed by the formation of distant metastasis.

Figure 12:
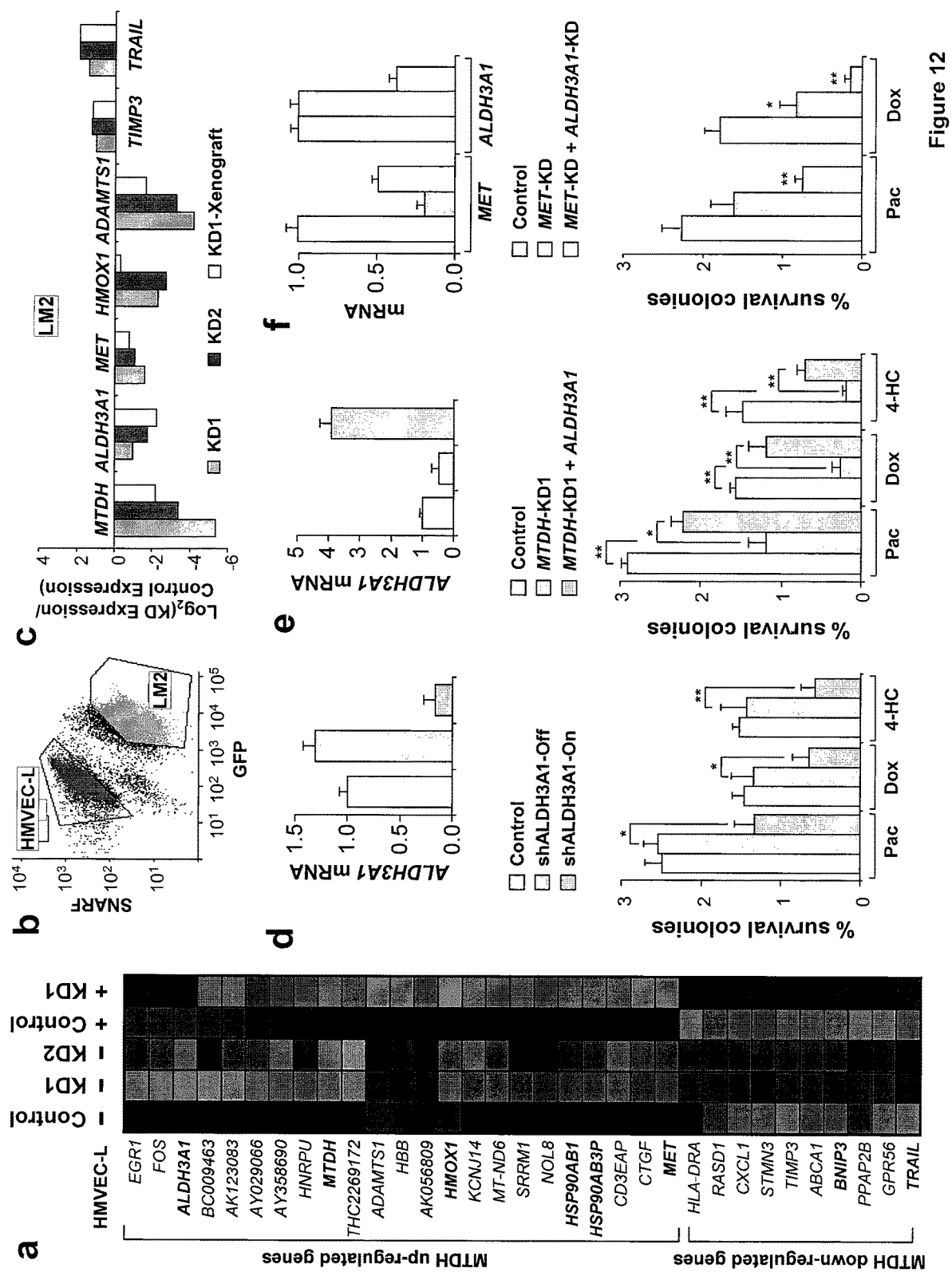
FIG. 12 demonstrates that ALDH3A1 and MET contribute to MTDH-mediated chemoresistance.

In some embodiments, microarray profiling of MTDH-knockdown cells reveals several genes, including MET, HMOX1, ALDH3A1, and two HSP90 family genes that may contribute to the chemoresistance function of MTDH. In some embodiments, the involvement of ALDH3A1 and MET in MTDH-mediated chemoresistance is further validated by a series of in vitro chemoresistance experiments in which the expression of ALDH3A1 and MET was altered in cancer cells (FIG. 12). As MTDH enhances chemoresistance of breast cancer cells to a broad spectrum of chemotherapeutic agents and physiological stresses, such a phenomenon may result from the concerted actions of multiple chemoresistance mediators identified in the microarray experiment. This is consistent with the observation that the reduction of chemoresistance is more significant in MTDH knockdown cells than in cells with individual knockdown of ALDH3A1 and MET, and that the effect of ALDH3A1 and MET double knockdown reaches a level similar to that of MTDH knockdown. Although MTDH may promote metastasis by enhancing cancer cell adhesion to endothelial cells, several genes identified by the microarray experiment may also contribute to the pro-metastasis function of MTDH. For example, genes that are down-regulated by MTDH inhibition include (but are not necessarily limited to) several previously reported metastasis-promoting genes such as MET, ADAMTS1 and CTGF[9, 59, 60]. Conversely, several genes that have been reported to suppress metastasis, including GPR56, TIMP3 and TRAIL[61-64], were overexpressed in the MTDH-knockdown line (FIG. 12a and Table 7).

In some embodiments, a combination of computational biology, in vivo and in vitro functional metastasis assays, and extensive clinical correlation analysis is used to identify an 8q22 poor-prognosis genomic gain that harbors the dual functional metastasis gene MTDH. In some embodiments, overexpression of MTDH occurs in up to 40% of breast cancer patients and promotes metastatic seeding as well as chemoresistance of breast tumors. In some embodiments, this study indicates several potential applications in the clinical management of human cancer, and in particular poor prognosis breast cancer. In some embodiments, genomic amplification and overexpression of MTDH represent a powerful prognosis marker independent from other well-established markers for cancer, and in particular poor prognosis breast cancer. In some embodiments, molecular targeting of the dual-function metastasis gene MTDH may not only prevent the seeding of cancer cells, and in particular poor prognosis breast cancer cells, to lung and other vital organs but also sensitize cancer cells to chemotherapy, thereby stopping the deadly spread of such cancers.

In some embodiments, the present invention relates to compositions and methods for cancer diagnosis, treatment and research, including but not limited to, cancer markers and uses of cancer markers. In particular, the present invention provides compositions and methods for targeting metadherin in cancer, and in particular poor prognosis breast cancer.

I. Cancer Therapies

In some embodiments, the present invention provides therapies for cancer (e.g., breast cancer, and in particular poor prognosis breast cancer). In some embodiments, therapies target metadherin. That is, in such embodiments, therapeutic methods are directed at reducing metadherin's activity by one means or another, and may be referred to herein as "anti-metadherin therapy." It is not intended that an anti-metadherin therapy be identified by any particular effect, such as reducing tumor burden, metastasis or angiogenesis. The objective of anti-metadherin therapy as the term is used herein is to promote the survival of the cancer patient. As described herein, studies conducted during the course of development of the present invention demonstrated a role for metadherin in cancer metastasis. Further studies demonstrated that interfering with metadherin is likely to result in a decrease in tumor proliferation, especially when the interfering agent is co-administered with another anti-proliferative agent. Accordingly, in some embodiments, the present invention provides methods of treating cancer (e.g., metastatic breast cancer and, in particular, poor prognosis breast cancer). In other embodiments, the present invention provides methods of preventing cancer metastasis (e.g., metastatic breast cancer).

A. Antibody Therapy

In some embodiments, the present invention provides antibodies that target tumors that express metadherin. Any suitable antibody (e.g., monoclonal, polyclonal, or synthetic) may be utilized in the therapeutic methods disclosed herein. In some embodiments, antibodies are antibodies to human metadherin. In other embodiments, antibodies are to a mouse (or other animal) metadherin homolog (i.e., the variant of the gene found naturally in that species).

In preferred embodiments, the antibodies used for cancer therapy are humanized antibodies. Methods for humanizing are well known in the art (See e.g., U.S. Pat. Nos. 6,180,370, 5,585,089, 6,054,297, and 5,565,332; each of which is herein incorporated by reference) but any antibody modified by any means that makes the antibody more amenable to use in humans than the unmodified version is understood herein to be a humanized antibody.

In some embodiments, the therapeutic antibodies comprise an antibody generated against metadherin, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for conjugation to antibodies, particularly cytotoxic or other anticellular agents having the ability to kill or suppress the growth or cell division of cells. The present invention contemplates the use of any pharmacologic agent that can be conjugated to an antibody, and delivered in active form. Exemplary anticellular agents include chemotherapeutic agents, radioisotopes that emit cell-damaging radiation, and cytotoxins. The therapeutic antibodies of the present invention may include a variety of cytotoxic conjugated agents, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety (i.e., a portion of a molecule that accounts for a function of the molecule) of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or *pseudomonas* exotoxin, to mention just a few examples. In some preferred embodiments, deglycosylated ricin A chain is utilized.

In any event, it is proposed that agents such as these may, if desired, be conjugated to an antibody, preferably in a manner that will allow the agent to be directed to the desired site in or on a tumor or tumor cell, effectively presented to the site and, if necessary or beneficial, to be taken up (internalized) by the target and/or released from the antibody to which it is conjugated. Known conjugation technology to achieve any or all of these objectives are well-known in the art (See, e.g., Ghose et al., Methods Enzymol., 93:280 [1983]).

For example, in some embodiments the present invention provides immunotoxins targeting metadherin. Immunotoxins are conjugates of a specific targeting agent, typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In preferred embodiments, antibody-based therapeutics are formulated as pharmaceutical compositions as described below. In preferred embodiments, administration of an antibody composition of the present invention results in a measurable decrease in cancer (e.g., decrease or elimination of tumor).

B. Antisense Therapies

In some embodiments, the present invention targets the expression of metadherin. For example, in some embodiments, the present invention employs compositions comprising oligomeric antisense compounds, particularly oligonucleotides (e.g., those identified in the drug screening methods described herein), for use in modulating the function of nucleic acid molecules encoding metadherin, ultimately modulating the amount of metadherin expressed. This is accomplished by providing antisense compounds that specifically hybridize with one or more nucleic acids encoding metadherin. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, splicing of the RNA to yield one or more mRNA species, translocation of the RNA from the nucleus to the site of protein translation in the endoplasmic reticulum, translation of protein from the RNA, and catalytic activity that may be engaged in or facilitated by the RNA. The overall effect of such interference with target nucleic acid function is modulation of the expression of metadherin. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a gene (or mRNA transcribed from the gene) whose expression is associated with a particular disorder or disease state, or a nucleic acid molecule from an infectious agent. In the present invention, the target is a nucleic acid molecule encoding metadherin. The targeting process also includes determining a site or sites within this gene for the antisense interaction to occur such that the desired effect, e.g., detection or modulation of expression of the protein, will result. Within the context of the present invention, a preferred site in the gene is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codons (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3' from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3) from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the "5' cap site" and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5" cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 bases (i.e., from about 8 to about 30 linked bases), although both longer and shorter sequences may find use with the present invention. Particularly preferred antisense compounds are antisense oligonucleotides, even more preferably those comprising from about 12 to about 25 bases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$-] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n OCH_3$, O($CH_2$)$_n NH_2$, O($CH_2$)$_n CH_3$, O($CH_2$)$_n ONH_2$, and O($CH_2$ $_n$ON[($CH_2$))$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the properties of an oligonucleotide with respect to what the oligonucleotide does functionally (i.e., its "pharmacodynamic" properties), and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or antisense "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex at an internal site. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

C. RNA Interference (RNAi)

In other embodiments, RNAi is utilized to inhibit metadherin function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, synthesised using a physical barrier (mask) by stepwise addition of each base in the sequence. Thus, the arrays represent a full oligonucleotide complement of a region of the target gene. Hybridisation of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol. Biol. 2005 May 13; 348(4):883-93, J Mol. Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

D. Genetic Therapies

The present invention contemplates the use of any genetic manipulation for use in modulating the expression of metadherin. Examples of genetic manipulation include, but are not limited to, gene knockout (e.g., removing the metadherin gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule-mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to a subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

E. Small Molecules

In still further embodiments, the present invention provides drugs (e.g., small molecule drugs) that target metadherin activity. In some embodiments, small molecule drugs are identified using the drug screening methods described below. In other embodiments, small molecule drugs are described in WO 04/071460, WO 04/071499, WO 03/084993, WO 03/075853, WO 05/021500, WO 05/021499, U.S. Applications 20040171552 and 20040138171, WO 03/072599, WO 05/021498, WO 05/020899, WO 04/098516 and WO 04/098512, each of which is herein incorporated by reference in its entirety.

F. Combination Therapy

In still further embodiments, one or more of the above described therapeutic agents are administered in combination. In some embodiments, a combination of a known chemotherapy agent (e.g., paclitaxel) and an antibody directed towards metadherin are utilized in the treatment of breast cancer. In certain embodiments, combination therapy (e.g., using a metadherin antibody and a known chemotherapy agent) is initially utilized, followed by maintenance therapy with a single agent (e.g., an antibody directed toward metadherin).

In some embodiments, the compounds of the present invention are provided in combination with known cancer chemotherapy agents. The present invention is not limited to a particular chemotherapy agent.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel, and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan, etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as bleomycins, etc., and plicamycin (mithramycin), 4) antimetabolites, including antifolates (e.g., methotrexate), purine antimetabolites (e.g., 6-mercaptopurine, 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines), 5-fluorouracil, 5-fluorodeoxyuridine (FdUrd), etc.), and cytosine arabinosides; 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors; 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

H. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but are not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, and the nature of the drugs or therapeutic agents administered, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual agents (such as oligonucleotides), and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide or other treatment agent is administered in maintenance doses, ranging from 0.01 µg to 100 g per kg of body weight, once or more daily or at longer intervals.

II. Markers for Cancer

The present invention further provides markers whose expression is specifically altered in cancerous tissues (including but not limited to breast cancer tissues) including poor prognosis tissues. Such markers find use in the diagnosis and characterization of breast cancer. For example, in some embodiments, increased levels of metadherin in breast samples serve as an indicator of the presence of cancer or the presence of cancer that has metastasized or is likely to metastasize (e.g., to lung).

In some embodiments, the present invention provides methods for detection of expression of metadherin. In preferred embodiments, expression is measured directly (e.g., at the RNA or protein level). In some embodiments, a method for detecting expression of metadherin and a different method for determining the number of copies of metadherin genes are both used and the "marker" is effectively the integrated result of applying the two methods. In some embodiments, expression is detected in tissue samples (e.g., biopsy tissue). In other embodiments, expression is detected in bodily fluids (e.g., including but not limited to, plasma, serum, whole blood, mucus, prostatic secretions, and urine). The present invention further provides panels and kits for the detection of markers. In preferred embodiments, the presence of a cancer marker (e.g., metadherin) is used to provide a prognosis to a subject. For example, the detection of increased levels of expression of metadherin in breast samples, especially when due to an increase in copy number, is associated with tumors that have metastasized. The information provided is also used to direct the course of treatment. For example, if a subject is found to have a marker indicative of a highly metastasizing tumor, additional therapies (e.g., hormonal or radiation therapies) can be started at an earlier point when they are more likely to be effective (e.g., before metastasis).

A. Detection of RNA

In some preferred embodiments, detection of metadherin is detected by measuring the expression of corresponding mRNA in a tissue sample (e.g., breast tissue). mRNA expression may be measured by any suitable method, including but not limited to, those disclosed below.

In some embodiments, RNA is detected by Northern blot analysis. Northern blot analysis involves the separation of RNA and hybridization of a complementary labeled probe.

In still further embodiments, RNA (or corresponding cDNA) is detected by hybridization of the RNA to be detected (the "target" RNA) to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Detection of Protein

In other embodiments, expressed metadherin is detected by measuring the expression of the corresponding protein or polypeptide. Protein expression may be detected by any suitable method. In some embodiments, proteins are detected by immunohistochemistry. In other embodiments, proteins are detected by their binding to an antibody raised against the protein. The generation of antibodies is described herein.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.)

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to metadherin is utilized.

In other embodiments, the immunoassay described in U.S. Pat. Nos. 5,599,677 and 5,672,480; each of which is herein incorporated by reference.

C. Data Analysis

In some embodiments, a computer-based analysis program is used to translate the raw data generated by the detection assay (e.g., the presence, absence, or amount of metadherin genes or expression products) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data are then prepared in a format suitable for interpretation by a treating clinician. For example, rather than providing raw expression data, the prepared format may represent a diagnosis or risk assessment (e.g., likelihood of metastasis) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

D. Kits

In yet other embodiments, the present invention provides kits for the detection and characterization of breast cancer. In some embodiments, the kits contain antibodies specific for metadherin, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

E. In Vivo Imaging

In some embodiments, in vivo imaging techniques are used to visualize the expression of metadherin in an animal (e.g., a human or non-human mammal). For example, in some embodiments, metadherin is labeled using a labeled antibody specific for metadherin. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to metadherin are described herein.

The in vivo imaging methods of the present invention are useful in the diagnosis of cancers that express metadherin (e.g., breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vive imaging methods of the present invention can further be used to detect metastatic cancers in other parts of the body.

In some embodiments, reagents (e.g., antibodies) specific for metadherin are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference). In other embodiments, antibodies are radioactively labeled.

The use of antibodies for in vivo diagnosis is well known in the art. Sumerdon et al., (Nuc. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of metadherin, to insure that the antigen binding site on the antibody will be protected. The antigen is separated after labeling.

In still further embodiments, in vivo biophotonic imaging is utilized for in vivo imaging. This real-time in vivo imaging utilizes luciferase. The luciferase gene is incorporated into cells, microorganisms, and animals (e.g., as a fusion protein with METADHERIN). When active, it leads to a reaction that emits light. A CCD camera and software is used to capture the image and analyze it.

III. Antibodies

The present invention provides antibodies having an affinity for (i.e., a propensity to bind) peptides of interest herein, in particular, metadherin. In preferred embodiments, the present invention provides monoclonal antibodies that specifically bind to a polypeptide comprised of at least five amino acid residues (i.e., having at least five amino acids, which may be identical or non-identical). These find use in the diagnostic and therapeutic methods described herein.

Antibodies against a protein of the present invention may be monoclonal or polyclonal, as long as they can recognize the protein (as evidenced by binding to it). Antibodies can be produced by using a protein of the present invention as the antigen according to a conventional antibody or antiserum preparation process.

Any suitable method may be used to generate the antibodies used in the methods and compositions of the present invention, including but not limited to, those disclosed herein. For example, to prepare either monoclonal or polyclonal antibodies, a protein as such or together with a suitable carrier or diluent is administered to an animal (e.g., a mammal) under conditions that permit the production of antibodies. That is, the protein is to serve as an antigen. For enhancing the antibody production capability, complete or incomplete Freund's adjuvant may be administered. Normally, the protein (i.e., antigen) is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an animal so treated (e.g., a mouse) is selected by "titrating" various dilutions of the animal's blood serum against a given amount of the antigen. A serum—of any dilution—that reacts with the antibody is an "antiserum." The most dilute antiserum that binds say, 50% of the antigen, is said to have the highest titer. Two to 5 days after the final immunization, the selected animal's spleen or lymph node is harvested and antibody-producing cells contained therein are isolated from one another, optionally allowed to undergo cell divisions thereafter, and then fused with myeloma cells to prepare the desired monoclonal antibody producer hybridoma. Measurement of the antibody titer in antiserum can be carried out, for example, by reacting a protein, labeled as described hereinafter, and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used to screen for hybridomas that are producing an antibody. For example, a supernatant of the hybridoma may be added to a solid phase (e.g., a microplate) that is capable of adsorbing antibody. Then an anti-immunoglobulin antibody (if mouse cells are used in cell fusion, anti-mouse immunoglobulin antibody is used) or Protein A (a "universal" binder of immunoglobulins) labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. A medium for animal cells to which HAT (hypoxanthine, aminopterin, thymidine) is added may be employed. Any selection and growth medium can be employed as long as the hybridoma can grow. For example, RPMI 1640 medium containing 1% to 20% (preferably 10% to 20%) fetal bovine serum, GIT medium containing 1% to 10% fetal bovine serum, or a serum free medium for cultivation of a hybridoma (SFM-101, Nissui Seiyaku) and the like can be used. Normally, the cultivation is carried out at 20° C. to 40° C. (preferably 37° C.) for about 5 days to 3 weeks (preferably 1 week to 2 weeks) under air or oxygen containing about 5% $CO_2$ gas. The antibody titer of the supernatant of a hybridoma culture can be measured according to the same manner as described herein with respect to the antibody titer of an antiserum.

Separation and purification of a monoclonal antibody (e.g., against metadherin) can be carried out according to any of the well-known methods for separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein an antibody is collected with an active adsorbent such as an antigen-binding solid phase, Protein A or Protein G and dissociating the complex to obtain the antibody.

Polyclonal antibodies may be prepared by any of a number of well-known methods or modifications of these methods. Briefly, an immunogen (i.e., any agent capable of inducing an immune system to mount an immune response when challenged by that agent) or a complex of an immunogen and a carrier (typically, a protein) is prepared and an animal is immunized by the complex according to the same manner as that described above for preparing a monoclonal antibody. As to the complex of the immunogen and the carrier protein to be used for immunization of an animal, any carrier protein and any mixing proportion of the carrier and a hapten (defined herein as an antigen to which the immune system responds optimally only if presented to the system with the carrier) can be employed as long as an antibody against the hapten, which is crosslinked on the carrier and used for immunization, is produced. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various agents can be used for coupling ("condensing") of a hapten and a carrier. For example, glutaraldehyde, carbodiimide, maleimide activated ester, activated ester reagents containing a thiol group or dithiopyridyl group, and the like find use with the present invention. The condensation product as such or together with a suitable carrier or diluent is administered to a site of an animal that permits of antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites (peritoneal fluid) and the like, of an animal immunized by the above method or from a subject who produces such antibodies as a result of having been challenged with an immunogen. The antibody titer in the antiserum can be measured in the manner described above with respect to the supernatant of the hybridoma culture. Separation and purification of the antibody can be carried out as described above with respect to the monoclonal antibody. In alternative embodiments, polyclonal antibodies in ascites fluid or in serum prepared from blood may be used without further isolation or purification. Such an antibody-containing serum is generally referred to as "antiserum."

The protein used herein as the immunogen is not limited to any particular type of immunogen. For example, metadherin (including a protein expression product of a metadherin gene having a partly altered nucleotide sequence) can be used as the immunogen. Further, fragments of the protein may be used. Fragments may be obtained by any methods including, but not limited to expressing a fragment of the gene, enzymatic processing of the protein, chemical synthesis, and the like.

IV. Drug Screening

In some embodiments, the present invention provides drug screening assays (e.g., to screen for anticancer drugs). In some embodiments, the screening methods of the present invention utilize metadherin. For example, in some embodiments, the present invention provides methods of screening for compounds that alter (e.g., increase or decrease) the expression of metadherin. In some embodiments, candidate compounds are antisense or siRNA agents (e.g., oligonucleotides) directed against metadherin. In other embodiments, candidate compounds are antibodies that specifically bind to metadherin. In yet other embodiments, candidate compounds are small molecules (i.e., biologically active but non-polymeric) that inhibit a biological activity of metadherin.

In one screening method, candidate compounds are evaluated for their ability to alter metadherin expression by contacting a compound with a cell expressing metadherin and then assaying for the effect of the candidate compounds on expression. In some embodiments, the effect of candidate compounds on expression of metadherin is assayed for by detecting the level of metadherin mRNA expressed by the cell. mRNA expression can be detected by any suitable method.

In other embodiments, the effect of candidate compounds on expression of a gene of interest (e.g., metadherin) is assayed by measuring the level of expressed polypeptide. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to metadherin, have an inhibitory effect on, for example, metadherin expression or metadherin activity, or have a stimulatory or inhibitory effect on, for example, the expression or activity of a metadherin substrate. Compounds thus identified can be used to modulate the activity of metadherin or other target gene product either directly or indirectly in a therapeutic protocol, to elaborate the biological function of the target gene product, or to identify compounds that disrupt normal target gene interactions. Compounds which inhibit the activity or expression of metadherin are useful in the treatment of proliferative disorders, e.g., cancer, particularly metastatic (e.g., to the lung) breast cancer.

In one embodiment, the invention provides assays for screening candidate or test compounds that are substrates of metadherin protein or polypeptide or a biologically active portion thereof. In another embodiment, the invention provides assays for screening candidate or test compounds that bind to or modulate the activity of metadherin protein or polypeptide or a biologically active portion thereof.

The test compounds of the present invention can be obtained using any of the numerous approaches in combinatorial library methods known in the art, including biological libraries (e.g., micro-organisms); peptoid libraries (libraries of molecules having the functionalities of peptides, but with a novel, non-peptide backbone, which are resistant to enzymatic degradation but which nevertheless remain bioactive; see, e.g., Zuckennann et al., J., Med. Chem. 37: 2678-85 [1994]); spatially addressable parallel solid phase or solution phase libraries; synthetic library methods requiring deconvolution (a mathematical means of managing "noise" in bodies of data); the 'one-bead one-compound' library method; and synthetic library methods using affinity chromatography selection. The biological library and peptoid library approaches are preferred for use with peptide libraries, while the other four approaches are applicable to peptide, non-peptide oligomer (as used herein, a polymer having only a few residues or "mers") or small molecule libraries of compounds (Lam (1997) Anticancer Drug Des. 12:145). The term "library" herein means a collection of one or another of the aforementnioned classes of agents or the like, assembled preferably according to a theme or algorithm constructed according to principles of combinatorial mathematics such as game theory—thus the term "combinatorial library."

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Compounds selected from libraries may be presented in solution (e.g., Houghten, Biotechniques 13:412-421 [1992]), or in or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

This invention further pertains to novel agents identified by the above-described screening assays. Accordingly, it is within the scope of this invention to further use an agent identified as described herein (e.g., a metadherin modulating agent, an antisense metadherin nucleic acid molecule, a siRNA molecule, a metadherin-specific antibody, or a metadherin-binding partner) in an appropriate animal model (such as those described herein) to determine the efficacy, toxicity or side effects of treatment with such an agent, or to elucidate its mechanism of action. Furthermore, novel agents identified by the above-described screening assays can be, e.g., used for treatments as described herein.

V. Transgenic Animals Expressing Metadherin Genes

The present invention contemplates the generation of transgenic animals that over-express or under-express (e.g., knockout animals) metadherin. The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

Experimental

The following are examples that further illustrate embodiments contemplated by the present invention. It is not intended that these examples provide any limitations on the present invention.

In the experimental disclosure that follows, the following abbreviations apply: eq. or eqs. (equivalents); M (Molar); .mu.M (micromolar); N (Normal); mol (moles); mmol (millimoles); .mu.mol (micromoles); nmol (nanomoles); pmoles (picomoles); g (grams); mg (milligrams); .mu.g (micrograms); ng (nanogram); vol (volume); w/v (weight to volume); v/v (volume to volume); L (liters); ml (milliliters); mu.1 (microliters); cm (centimeters); mm (millimeters);

.mu.m (micrometers); nm (nanometers); C (degrees Centigrade); rpm (revolutions per minute); DNA (deoxyribonucleic acid); kdal (kilodaltons).

I. Results

1. Recurrent Poor-Prognosis Genomic Alterations

A bioinformatic strategy termed ACE (Analysis of CNAs by Expression data) (FIG. 1a) was developed to sensitively detect CNAs that affect regional gene expression. ACE first calculates the expression scores of all genes according to expression differences between comparison groups, and then orders these scores based on genomic position. To measure the regional expression pattern, a neighborhood score (NS) is calculated for each genomic locus using a geometry-weighted sum of expression scores of all the genes on the chromosome. Since locus linkage strength decays with distance, the expression scores of genes in proximity to the locus in consideration are assigned greater weights than those farther away. NS significance is estimated by permutation, with regions with a stretch (≥20) of aberrant NS declared potential CNA regions.

Once the efficacy of the ACE method was validated using a number of existing gene expression profiling datasets that have corresponding genomic alteration information (See FIG. 2), the method was used to study genomic alterations associated with poor prognosis human cancers, and in particular poor prognosis breast cancer. Three separate studies previously identified two poor-prognosis gene sets (70 and 76 genes, respectively) that can be used to robustly predict the clinical outcome of human breast cancers. However, only a single gene (CCNE2) is present in both signatures. Analysis of these three datasets using the ACE method identified five common genomic gains in at least two datasets (Table 1) and 15 other genomic gains in one of the three datasets (Supplementary Table 2). The smallest regions of overlap (SRO) of common CNA events, namely, gains at 3q26-27, 8q22, 8q24.3, 17q23-25 and 20q13.3, are among a large number of genomic alterations previously observed in high frequencies in breast cancer, although their links to poor prognosis and tumor progression have not been established[35-40]. Genomic losses associated with more than one dataset were not detected. This is consistent with previous observations that genomic gains are more prevalent than genomic losses in cancer, particularly poor prognosis breast cancer[38-40]. Of the five prevalent genomic events, the 8q22 gain was consistently observed in all three datasets (FIG. 1b). The NS of the 8q22 region was calculated for each sample in the three datasets; the resulting score was used to classify tumor samples into two groups (high NS and low NS). FIG. 1c and Table 3, demonstrate that the probability of metastasis-free survival of patients with a high 8q22 NS was significantly lower than the control group in all three datasets. These analyses suggested that the genomic gain of 8q22 is a strong predictor of breast cancer poor prognosis.

a) FIG. 1

Figure 2:
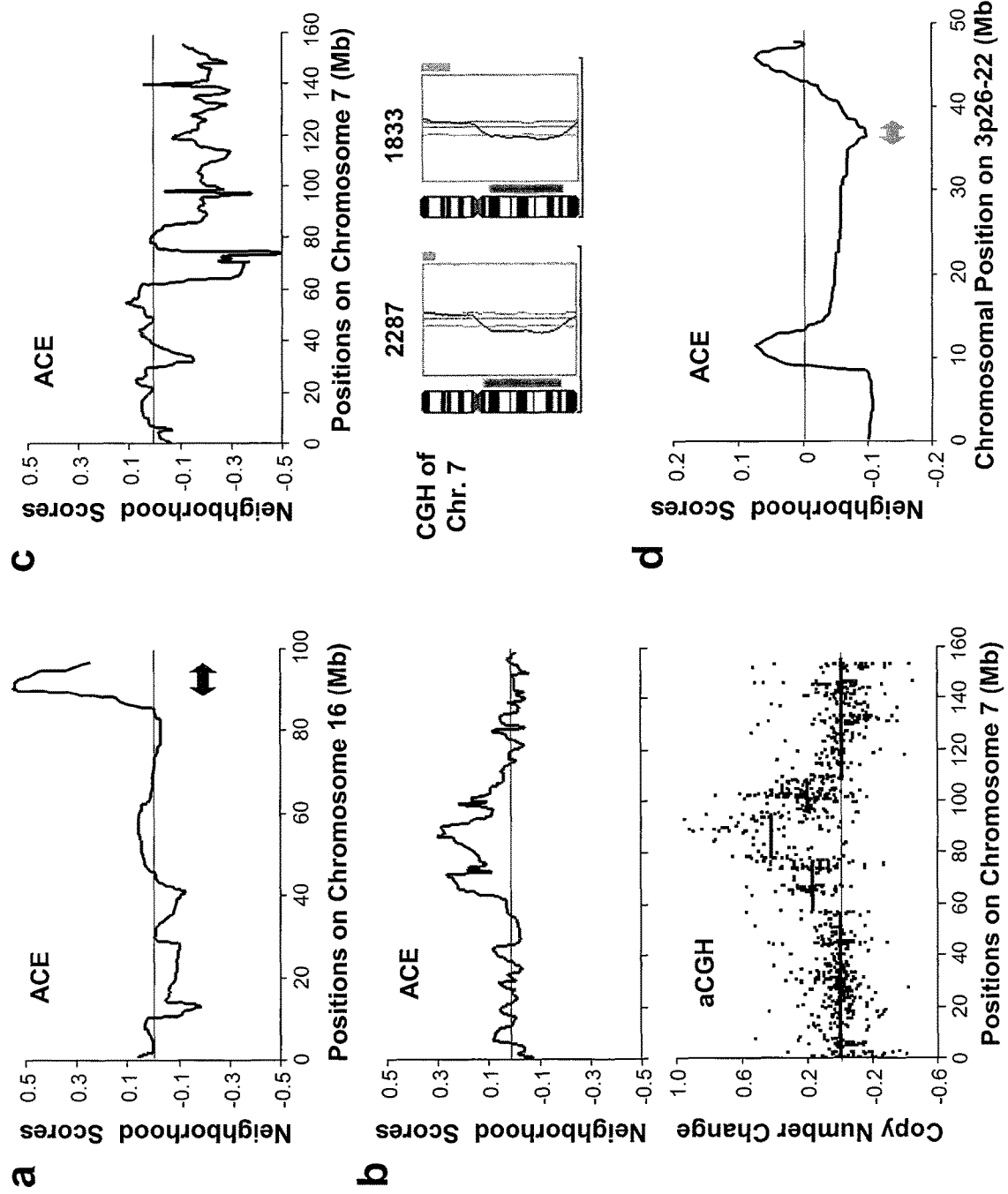
FIG. 2 depicts validation of the ACE algorithm using available expression data with corresponding genomic alteration data.

FIG. 1 demonstrates the use of ACE analysis to identify a recurrent genomic gain at 8q22 in poor-prognosis breast cancer. FIG. 1a represents a schematic overview of the ACE approach. Briefly, the expression score (ES) of each gene is calculated by comparing samples of different phenotypes, and then a neighborhood score (NS), indicative of the DNA amplification status, is computed for each locus as the geometry-weighted ES sum of all the genes on the chromosome. Regions of gain (red, bottom panel) and loss (green) were defined by applying NS cutoffs (dotted lines) obtained from permutations. i,j, gene index when they are ordered on the chromosome by genomic positions; c, normalizing constant; $w_{ji}$, weight of gene j when locus i is in consideration. $ES_i$, expression score of gene i. $NS_i$, neighborhood score of locus i. FIG. 1b depicts the detection of a poor-prognosis genomic gain at 8q22 in all three expression datasets by van't Veer[14], van de Vijver[15] and Wang[16] et al. The traces are the NS scores on chromosome 8 produced by ACE. The shaded area highlights the consensus region of gain at 8q22. Red and green peaks represent statistically significant regions of gains or loss, respectively. FIG. 1c depicts Kaplan-Meier metastasis-free survival curves of patients with high or low 8q22 NS.

b) FIG. 2

FIG. 2 depicts the validation of the ACE algorithm using available expression data with corresponding genomic alteration data. FIG. 2a depicts expression microarray data of the brain tissue from Ts1Cje mice compared to that of the normal mice[71] (Ts1Cje mice represent the Down Syndrome animal model known to have a partial trisomic region on chromosome 16). ACE predicted a sole CNA region on chromosome 16. The NS produced by ACE is shown along this chromosome, where the red line indicates the predicted region of gain. Red double-arrow: the known trisomic region in Ts1Cje mice. FIG. 2b depicts taxane-resistant cells established by continuous exposure of docetaxel or paclitaxel to 6 ovarian cancer cell lines 1A9, ES-2, MESOV, OVCA429, OVCA433 and OVCAR-3[72]. ACE detected 3 amplified regions on chromosome 7 in the taxane-resistant derivatives when compared to their parental lines (upper panel), which were highly consistent with the analysis of CGH data (lower panel). Colored horizontal lines in the lower panel are the segment means produced by the CGH analysis tool CBS, of which red indicates the significant regions of gain. FIG. 2c demonstrates the use of ACE to compare the expression of 10 cell lines derived from the breast cancer cell MDA-MB-231 with high or low breast-to-bone metastatic capability[9] and defined a loss at chromosome 7q associated with bone metastasis. The upper panel shows the NS of chromosome 7 in the highly metastatic cells with green lines indicating predicted regions of loss. The lower panel displays the previously published CGH data of the same chromosome in the two highly metastatic lines 2287 and 1833, with DNA of the lowly metastatic parental line MDA-MB-231 used as a control[9]. Red and green vertical bars indicate regions of genomic loss and gain, respectively. FIG. 2d depicts the use of ACE to analyze regional epigenetic regulation using the gene expression data of bladder tumors[70]. Partial chromosome 3 is shown. Dark green double-arrow: the epigenetic regulated region that was experimentally validated in a previous study[70]. See Table 4 for all significant regions in this dataset.

2. Validation of 8q22 Genomic Gain in Breast Tumors

Figure 7:
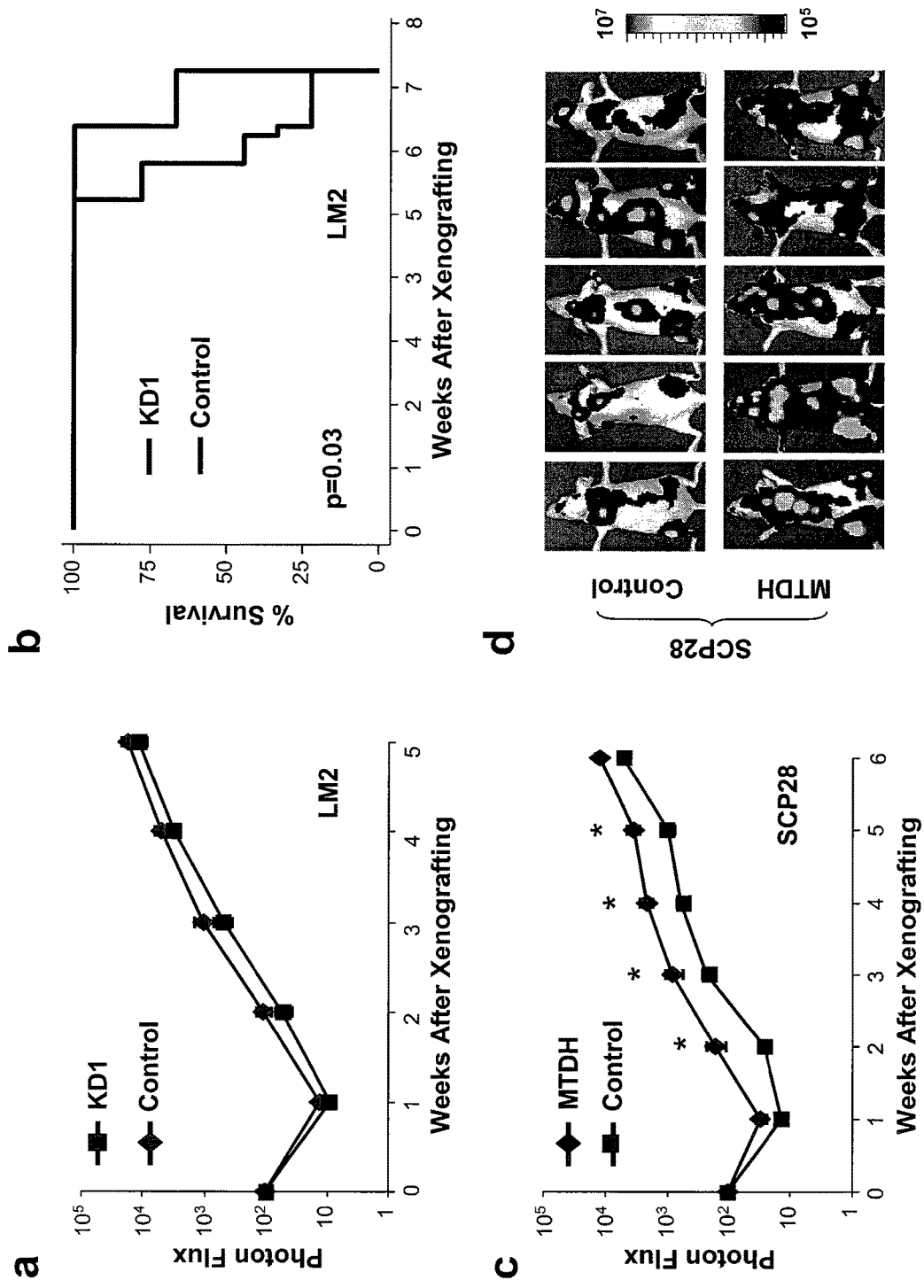
FIG. 7 demonstrates organ-specific metastasis mediated by MTDH.

Fluorescence in situ hybridization (FISH) and genomic DNA real-time PCR (qPCR) was used to confirm 8q22 amplification in breast tumor samples. A panel of microdissected tumor samples from fresh frozen breast cancer specimens was first analyzed by qPCR using four primer pairs that amplify DNA sequences at chromosome 8q21, q22 and q23 (FIG. 3a, b). As shown in Table 5, ten of 36 tumors (27.8%) were found to have aberrantly higher copy numbers (>3.6) at 8q22 as compared to control human DNA sample. As shown in FIG. 5b, these 10 genomic gain events spanned chromosomal regions 8q21 to 8q23, with a consensus region at 8q22. This result is consistent with the computational prediction. DNA copy numbers detected by genomic qPCR analysis are consistent with FISH analysis of the same tumor specimens (FIG. 7). To confirm the link between 8q22 genomic gain and elevated expression of genes located in this region, qRT-PCR was used to investigate expression patterns of three genes at 8q22 (PTDSS1, MTDH and LAPTM4β) in these tumors. The results demonstrated a strong positive correlation between the expression of these genes and the 8q22 copy numbers (FIG. 3b). Analysis of a separate panel of 18 paraffin-embedded breast tumors showed yielded similar results (Supplementary Table 5).

Figure 3:
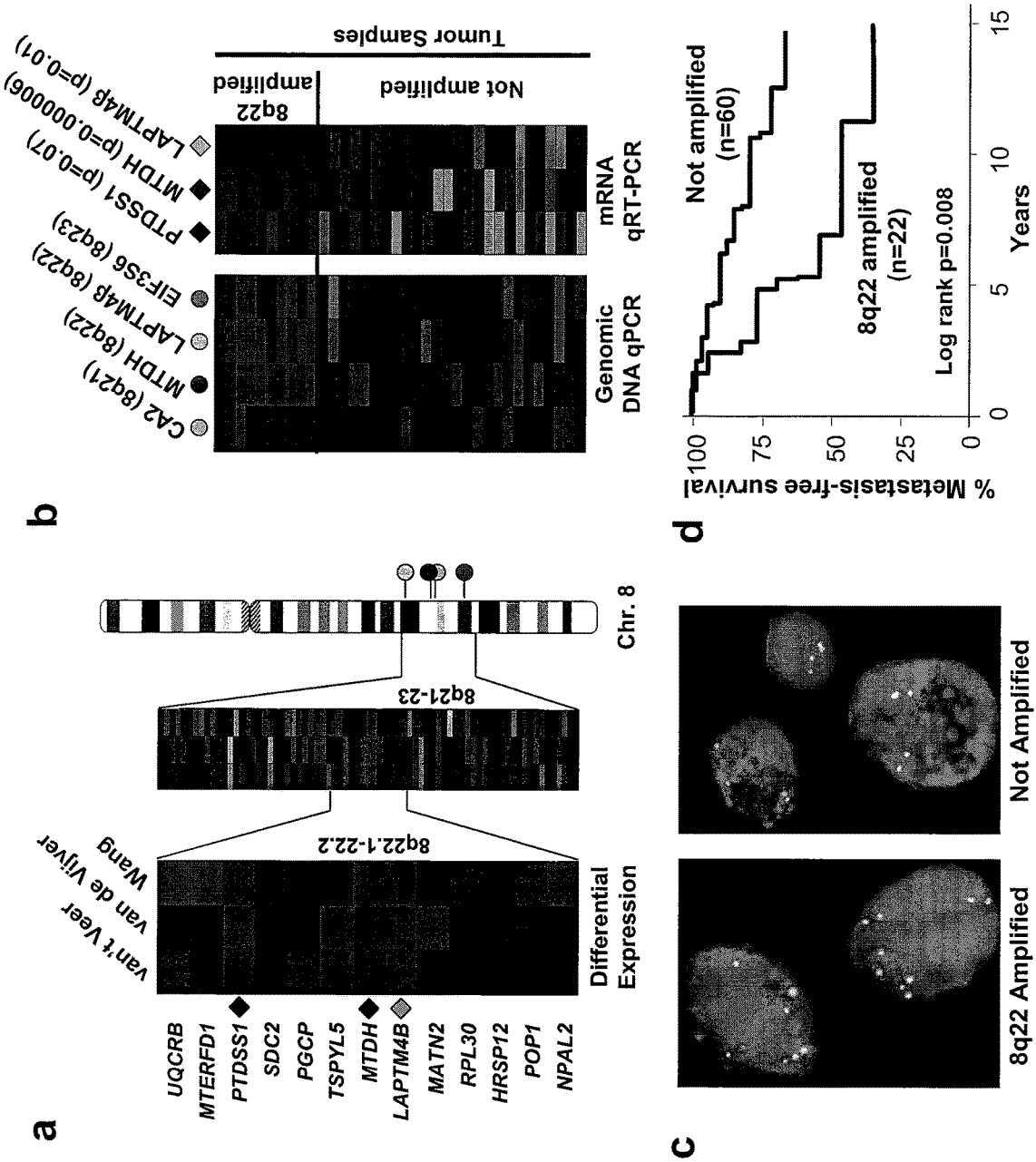
FIG. 3 depicts the validation of 8q22 amplification in human breast tumors.

A breast cancer tissue microarray with corresponding detailed clinicopathological records was also analyzed by FISH using a bacterial artificial chromosome (BAC) probe located at the 8q22 region. Results showed that 22 (26.8%) of the 82 hybridized primary tumor samples had an average 8q22 copy number larger than 3 (FIG. 3c, Table 6). Notably, 8q22 amplification was associated with a higher propensity of cancer recurrence (FIG. 3d). For example, about 65% of the patients with 8q22 genomic gain suffered from metastasis 17 years after the initial cancer diagnosis, as compared to 30% of patients without 8q22 amplification (Log rank P=0.002). Along with the qPCR analysis described above, these data confirmed the ACE prediction that recurrent genomic amplification at 8q22 leads to regional gene activation. More importantly, these results established 8q22 amplification as a breast cancer poor-prognosis marker event.

a) FIG. 3

Figure 4:
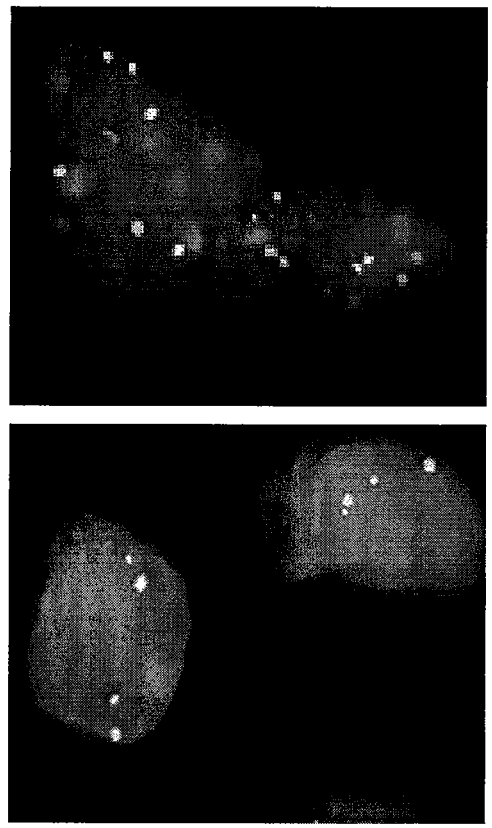
FIG. 4 depicts DNA copy number quantification by FISH and genomic DNA qPCR.

FIG. 3 depicts the validation of 8q22 amplification in human breast tumors. FIG. 3a demonstrates that the majority of the genes at the 8q22 region are overexpressed in poor-prognosis tumor samples of the three published datasets[14-16]. Heatmap shows the differential expression of these genes in poor-prognosis vs. good-prognosis samples. Red indicates overexpression, while green denotes underexpression. FIG. 3b depicts the validation of the computational prediction of 8q22 genomic gain. A panel of human breast tumor samples obtained from LCM was analyzed for 8q22 genomic alterations and gene expression using qPCR. Shown are the DNA copy numbers of 4 genomic loci at 8q21-23 (filled circles) analyzed with the extracted tumor DNA, and the expression levels of 3 genes at 8q22 (diamonds) quantified with the tumor RNA. Student's t-test P values of expression comparison in samples with and without 8q22 gain are shown in parenthesis after each gene. FIG. 3c depicts breast cancer tissue microarray FISH analysis with the green SpectrumGreen and red SpectrumOrange probes detecting chromosome 8 centromere and the 8q22 region, respectively. About 50 nuclei were scored per sample. A case of 8q22 amplification (left) and a diploid case (right) were shown. FIG. 3d depicts Kaplan-Meier survival analysis in breast cancer patients with or without 8q22 amplification.

b) FIG. 4

FIG. 4 depicts DNA copy number quantification by FISH and genomic DNA qPCR. Shown are FISH images of 2 paraffin tissue samples with red and green probes for 8q22 and chromosome 8 centromere, respectively. The average 8q22 copy numbers scored from at least 100 nuclei in FISH and from the genomic qPCR assay were also shown for each sample.

3. MTDH Promotes Breast Cancer Metastasis

Thirteen of the 20 genes in 8q22 were represented on the microarrays used in the three analyzed datasets (FIG. 3a). To determine the functional targets of 8q22 gain, six resident genes considered most likely to promote cancer progression were tested. UQCRB, PTDSS1, TSPYL5, MTDH and LAPTM4b were significantly overexpressed in metastatic diseases in at least two of these datasets (student's t-test, P<0.05), and SDC2 was reported to mediate cell adhesion and proliferation in colon cancer[41] (FIG. 6). To examine their role in metastasis, each gene was stably overexpressed in the SCP28 cell line, a subline of the human breast cell line MDA-MB-231 that is mildly metastatic to lung and bone when injected into mice[9, 42]. The cell line was labeled with a retroviral construct expressing a GFP/luciferase fusion protein[42], and its in vivo metastasis capability was monitored by noninvasive bioluminescent imaging after intravenous injection. Data showed that MTDH overexpression significantly accelerated the development of lung metastasis and shortened the survival of mice that received tumor cell xenografts (FIG. 5a-d and FIG. 6). Animal metastasis burden caused by MTDH overexpression was nearly 7-fold higher than controls six weeks after cancer cell injection. In contrast, overexpression of the other five genes, either individually or in combination, failed to enhance the metastasis ability of SCP28 (FIG. 6), suggesting that MTDH is likely the most significant functional mediator of this poor-prognosis genomic gain. MTDH is located at the center of the 8q22 minimal consensus genomic gain and has been shown to encode a cell surface protein responsible for promoting mouse mammary tumor cell adhesion to lung endothelial cells[32]. However, the functional role of MTDH in human breast cancer and the mechanism of its deregulation have not been previously investigated. To further validate the role of MTDH in metastasis, two different short-hairpin RNA (shRNA) constructs were used to knock down the expression of MTDH in the LM2 cell line (an MDA-MB-231 subline selected in vivo for its high lung metastasis propensity)[11]. MTDH knockdown significantly reduced the lung metastasis burden of LM2 by 3-5 fold and extended the survival of the mice by 1-2 weeks (FIGS. 5a, e-g and FIG. 6). The effect of altered MTDH expression on bone and brain metastasis was also examined by injecting the genetically modified breast cancer cell lines into the left cardiac ventricle of recipient nude mice. MTDH knockdown in LM2 resulted in a modest but significant improvement of post-injection survival, although bioluminescent quantification of the decrease of bone and brain metastasis burden did not reach statistical significance. Conversely, overexpression of MTDH in SCP28 cells led to a modest but significant increase of bone and brain metastasis (FIG. 7). These results suggested that MTDH preferentially promotes metastasis to lung, while having a modest effect on metastasis to other organs.

Figure 5:
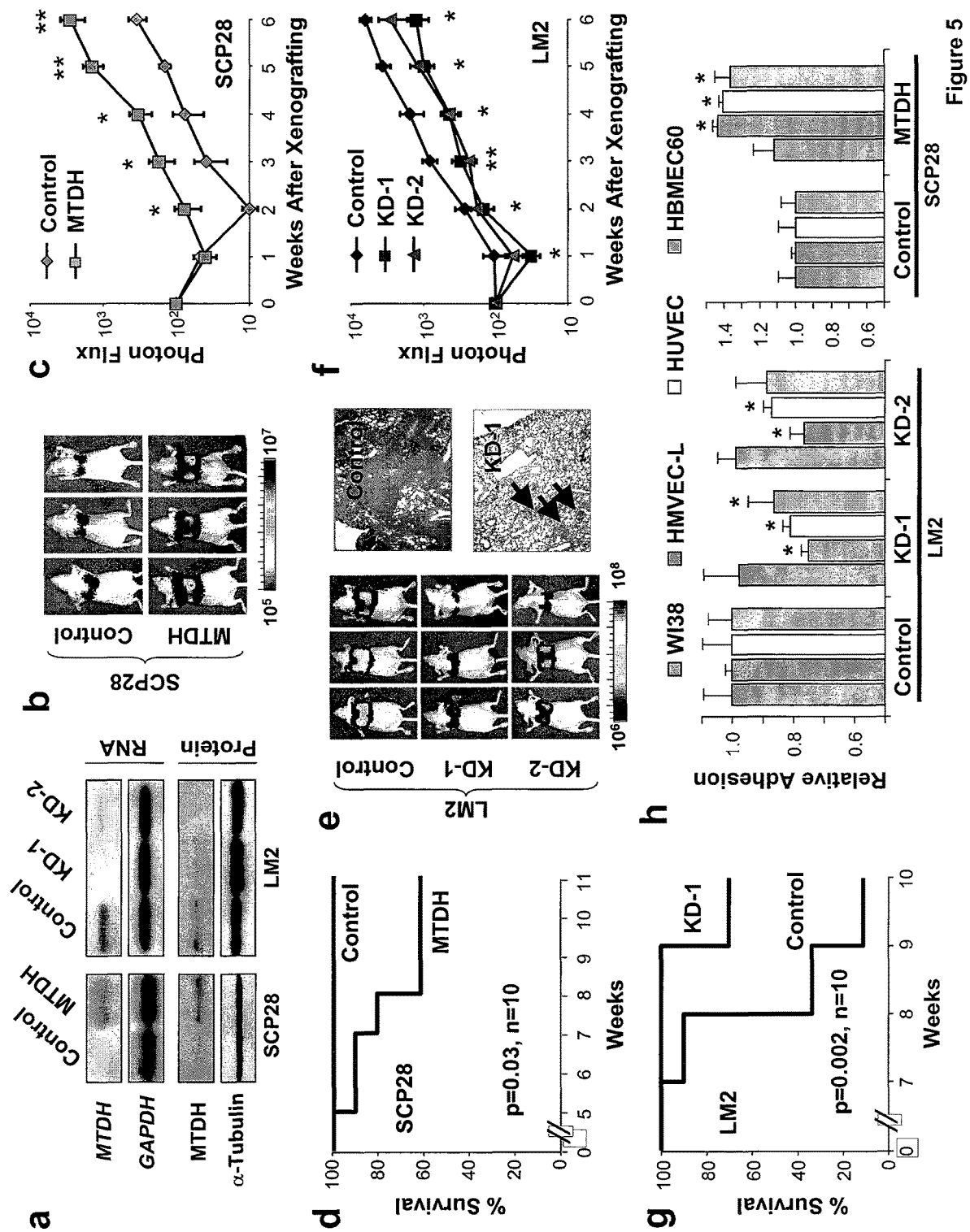
FIG. 5 demonstrates that MTDH mediates lung metastasis of human breast cancer.
Figure 6:
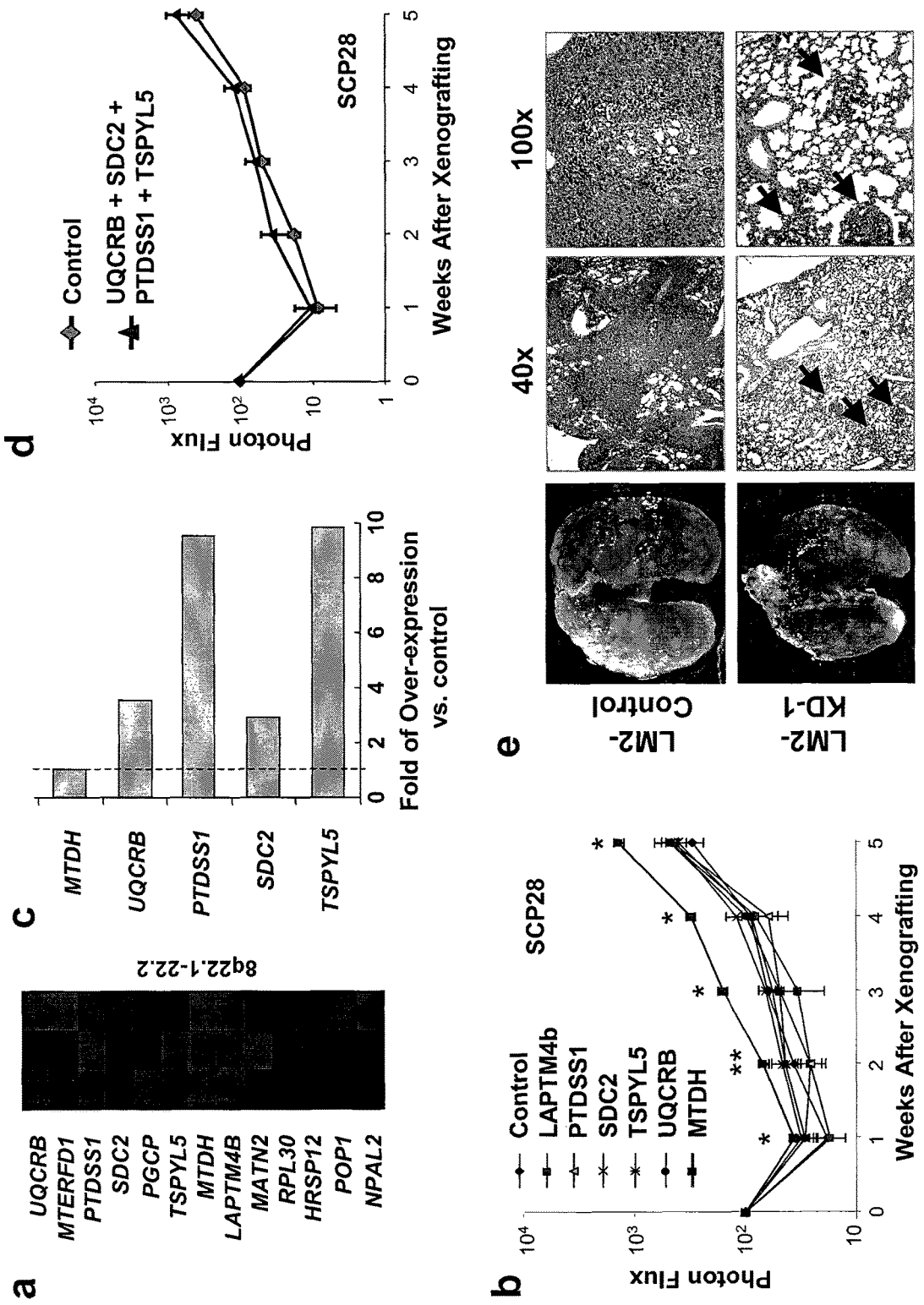
FIG. 6 demonstrates that overexpression analysis of 8q22 genes identified MTDH as the target gene of the amplicon to promote metastasis.
Figure 8:
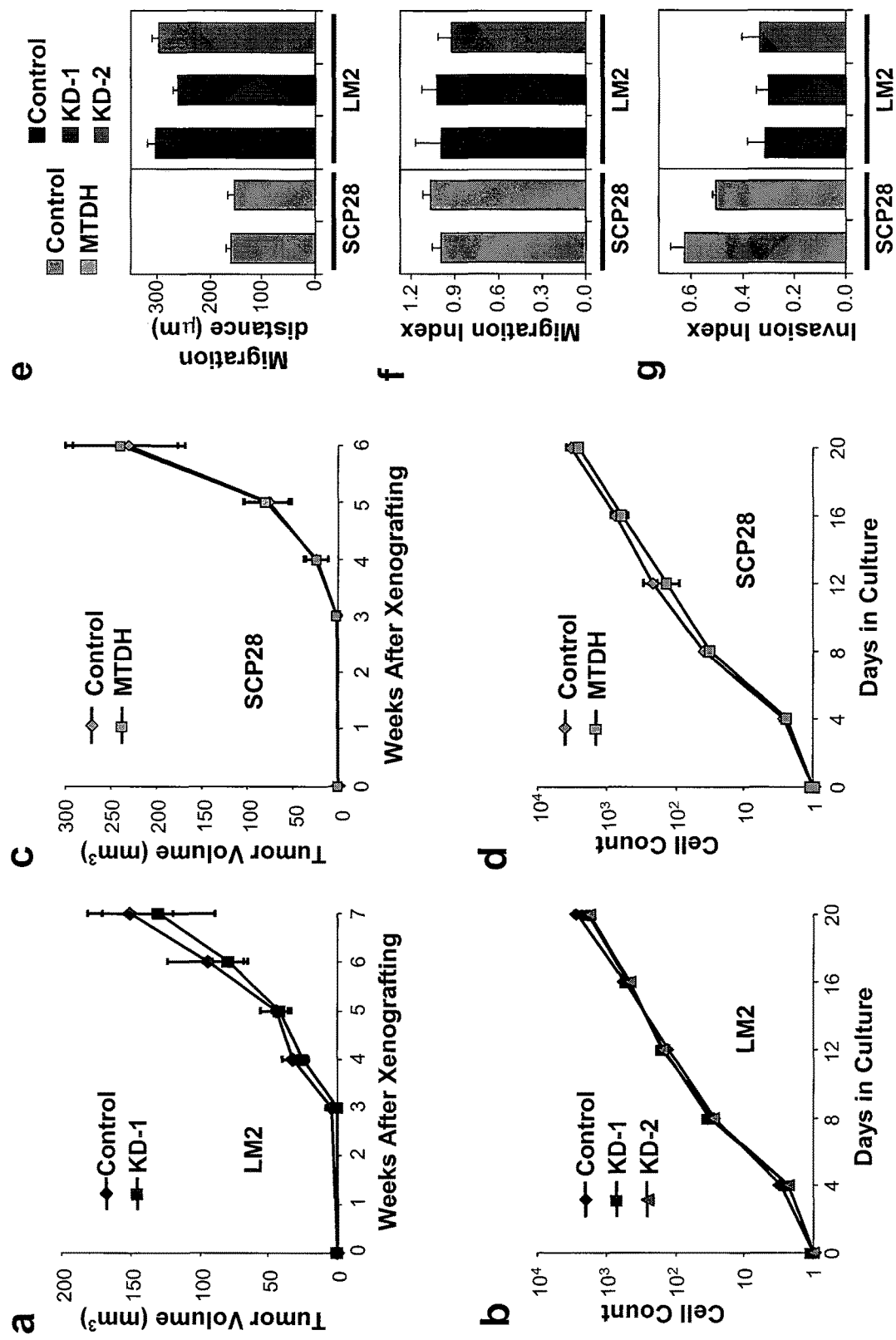
FIG. 8 demonstrates that MTDH does not influence the growth, migration or invasion of tumor cells.

The functional role of MTDH in the multistep process of metastasis was also investigated[4, 5]. MTDH knockdown or overexpression did not affect the growth, migration or invasiveness of tumor cells (FIG. 8). However, MTDH knockdown significantly reduced the adhesion of the cancer cells to lung microvascular endothelial cells (HMVEC-L), as well as to endothelial cells of the bone marrow (HBMEC60) and the umbilical vein (HUVEC), albeit to a lesser extent. A reciprocal change was observed when MTDH was overexpressed (FIG. 5h). In contrast, the adhesion of cancer cells to the WI-38 lung fibroblast cell line was not affected. MTDH did not promote intravasation or extravasation through endothelial layers based on both in vitro transendothelial assays (FIG. 8) and in vivo metastasis assays using an orthotopic xenograft method (data not shown). Instead, MTDH appeared to specifically enhance the seeding of tumor cells to the target organ endothelium.

a) FIG. 5

FIG. 5 demonstrates that MTDH mediates lung metastasis of human breast cancer. FIG. 5a shows that MTDH is constitutively overexpressed in the mildly metastatic cells SCP28, and stably knocked down in the highly lung-metastatic cells LM2 with two independent hairpin constructs.

Shown are the Northern and Western blot results. FIG. 5b depicts an in vivo metastasis assay of SCP28 cells with or without MTDH overexpression. Luciferase-labeled SCP28 cells were inoculated into nude mice intravenously, and the lung metastasis burden of xenografted animals was monitored weekly using non-invasive bioluminescent imaging (BLI). Shown are BLI images of representative mice at the sixth week after injection. The color scale depicts the photon flux (photon per second) emitted from the metastasis cells. FIG. 5c depicts BLI quantification of lung metastasis of SCP28 cells. FIG. 5d depicts Kaplan-Meier survival curves of mice inoculated with SCP28 cells. FIG. 5e depicts in vivo metastasis assays of LM2 cells with or without MTDH knockdown. Shown are the representative BLI images and lung sections of the inoculated mice at the sixth week after injection. Arrows point to the sporadic lesions by MTDH knockdown cells as compared to much more prevalent tumor lesions by control cells. FIG. 5f depicts BLI quantification of lung metastasis by LM2 cells. FIG. 5g depicts Kaplan-Meier survival analysis of the mice injected with LM2 cells. FIGS. 5c and 5f data represent averages±SEM of 10 mice. *P<0.05; **P<0.01 based on a two-sided Wilcoxon rank test. FIG. 5h demonstrates that MTDH promotes the adhesion of cancer cells to endothelial cells as tested by endothelial-adhesion assays. Genetically modified SCP28 or LM2 cells were seeded on top of a monolayer of endothelial cells from lung (HMVEC-L), umbilical vein (HUVEL), bone marrow (HBMEC60) and control fibroblast cells (WI38). Cancer cells were seeded on top of the endothelial or fibroblast monolayer and the attached cells were quantified 3 hours later.

b) FIG. 6

FIG. 6 demonstrates the use overexpression analysis of 8q22 genes to identify MTDH as the target gene of the amplicon to promote metastasis. Supplementary FIG. 6a depicts differential expression patterns of genes at 8q22 in patients with poor prognosis compared to those with good prognosis. To identify the amplification target gene(s) among those, six putative candidates including MTDH (color highlighted) with the expression pattern most strongly correlated with prognosis or previously implicated in tumor biology were chosen and their possible roles to promote metastasis were analyzed using the xenografting animal model. FIG. 6b depicts the analysis of SCP28 cells; cells that overexpress each of the six genes as well as the empty vector were tested for their metastatic capability. The cells were injected into nude mice intravenously, followed by bioluminescent imaging to monitor the animal lung metastasis burden. Shown are the normalized luminescent signals from the cancer cells colonized in lung. Only MTDH overexpression led to significant increase of lung metastasis. *P<0.05; **P<0.01, two-sided Wilcoxon rank test to compare MTDH overexpression vs. control. FIG. 6c is included to rule out the possibility of a combinatory effect of the other genes by simultaneous overexpression in the SCP28 cells. FIG. 6d demonstrates that xengrafting assays of the cells with combinational overexpressed did not show an increase of lung metastasis. FIG. 6e depicts photographs and hematoxylin/eosin stain sections of representative lungs harvested at necropsy from mice injected with control and MTDH-knockdown LM2 cells.

c) FIG. 7

FIG. 7 demonstrates that MTDH mediates organ-specific metastasis. While MTDH shows a strong causal role in breast-to-lung metastasis, it only mildly promotes breast-to-bone metastasis in mice. When the LM2 cells with MTDH knockdown were inoculated via intracardiac injection into the nude mice to generate bone and brain metastasis, a slight decrease in the bone metastasis (FIG. 7a) and a modest but significant improvement of animal survival (FIG. 7b) was observed. n=10. Reciprocally, MTDH overexpression in SCP28 led to a significant increase in the bone metastasis propensity (FIG. 7c). n=10. *P<0.05 based on a two-sided Wilcoxon rank test. FIG. 7d depicts representative BLI images of systemic metastasis burden in mice injected with SCP28 control and MTDH-overexpression cells.

d) FIG. 8

FIG. 8 demonstrates that MTDH does not influence the growth, migration or invasion of tumor cells. Supplementary FIG. 8a depicts LM2 cells with MTDH knockdown or control hairpin expression were inoculated into the #4 mammary fat pad of nude mice. Length and width of the primary tumors were measured, and the tumor volumes were calculated at the indicated time points. FIG. 8b demonstrates that the in vitro proliferation rates of LM2 cells were not affected by MTDH knockdown. FIG. 8c depicts the growth curve of the SCP28 control or MTDH overexpression cells after inoculation into mammary fat pads. FIG. 8d depicts the in vitro proliferation rates of SCP28 cells. Alteration of MTDH expression in LM2 or SCP28 cells did not lead to change of migration and invasion properties of the cancer cells as measured by wound healing assays (FIG. 8e), Boyden two-chamber migration assay (FIG. 80f), and two-chamber matrigel invasion assay (FIG. 8g). Results represent average values of three or more independent experiments with SEM as error bars.

4. MTDH Promotes Chemoresistance

Poor prognosis of breast cancer at the time of diagnosis or surgery indicates a higher probability of death as the result of recurrent tumors and development of metastases in vital organs. Emergence of metastasis reflects not only the ability of cancer cells to overcome hurdles during the multi-step process of metastasis[4, 5], but also the capability to survive standard adjuvant therapy and other physiological stresses. Therefore, the driver gene of a poor-prognosis genetic amplification might function to promote chemoresistance in addition to enabling the metastasis process. A bioinformatic analysis of the available NCI60 pharmacogenomic data[43] indicated a potential contribution of the genes at 8q22 to chemoresistance. The NCI60 data include the cytogenetic and expression profiles of 58 cancer cell lines as well as their sensitivity profiles to 24,000 small molecule compounds. Analysis of such data revealed that genomic gain at 8q22 strongly correlates with a higher overall gene expression of this region (Pearson's r=0.578, FIG. 10); intriguingly, this higher NS is in turn associated with a significantly higher mean $GI_{50}$ (the drug concentration for 50% growth inhibition) for 1,123 compounds, as compared to 211±178 compounds expected by random permutation (P=0.019, FIG. 9a).

To investigate the chemoresistance function of MTDH and other genes in 8q22, genetically modified breast cancer cell lines used for in vivo metastasis assays were treated with chemotherapeutic or other stress agents including paclitaxel, doxorubicin, cisplatin, and hydrogen peroxide with or without co-culture with the HMVEC-L endothelial cell line. Long-term survival of the cells was then quantified by clonogenic assays. Inhibition of MTDH expression sensitized the LM2 cell line to chemotherapeutic and stress agents, while overexpression of MTDH rendered SCP28 cells more resistant to these treatments (FIG. 9b-d). In contrast, overexpression of up to 4 other genes in the 8q22 locus did not significantly alter the chemosensitivity of cancer cells (FIG. 9d). MTDH-dependent chemoresistance was further enhanced when cancer cells were co-cultured with HMVEC-L lung endothelial cells (FIG. 9b, c).

Figure 9:
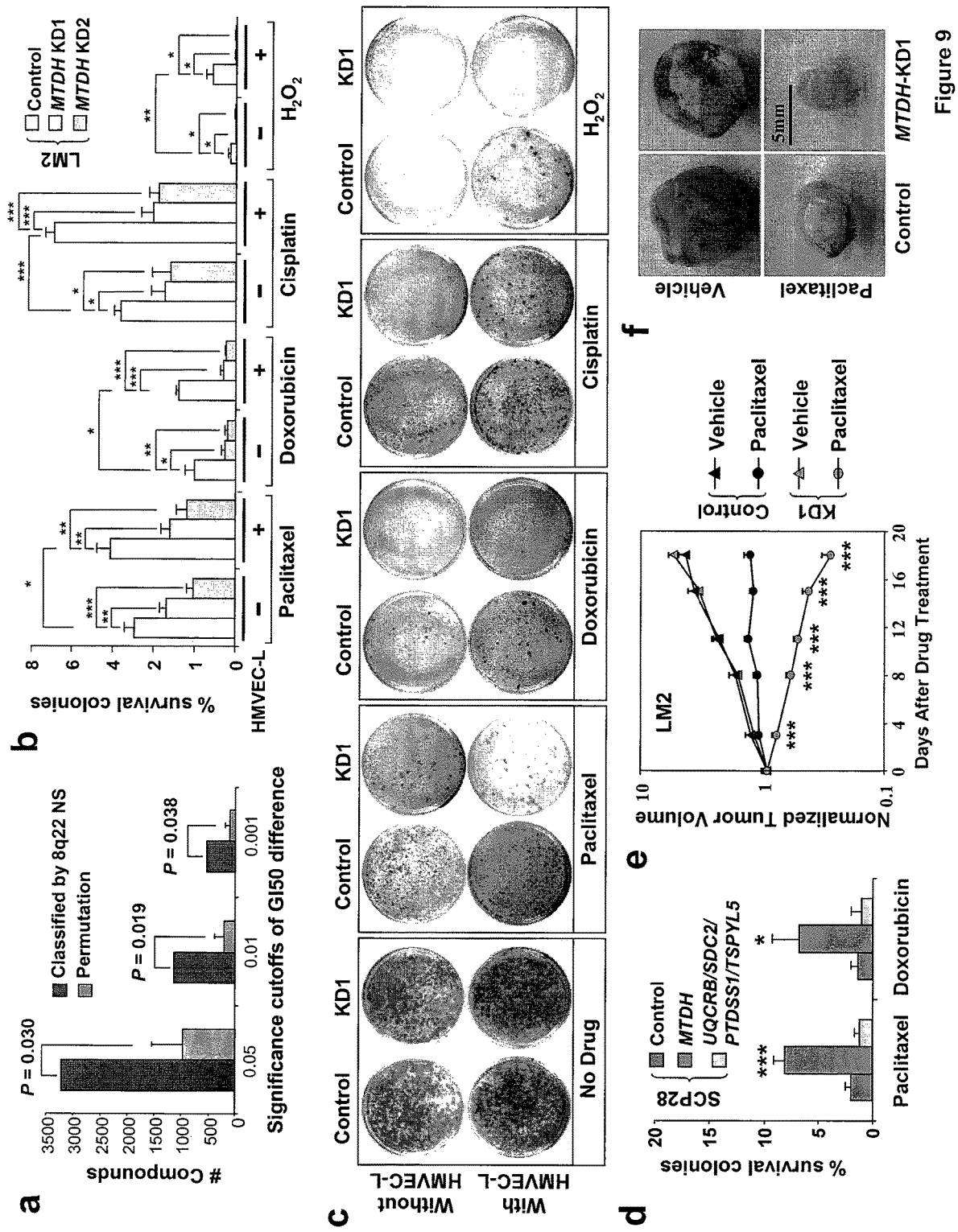
FIG. 9 demonstrates that MTDH enhances chemoresistance of breast cancer cells.
Figure 11:
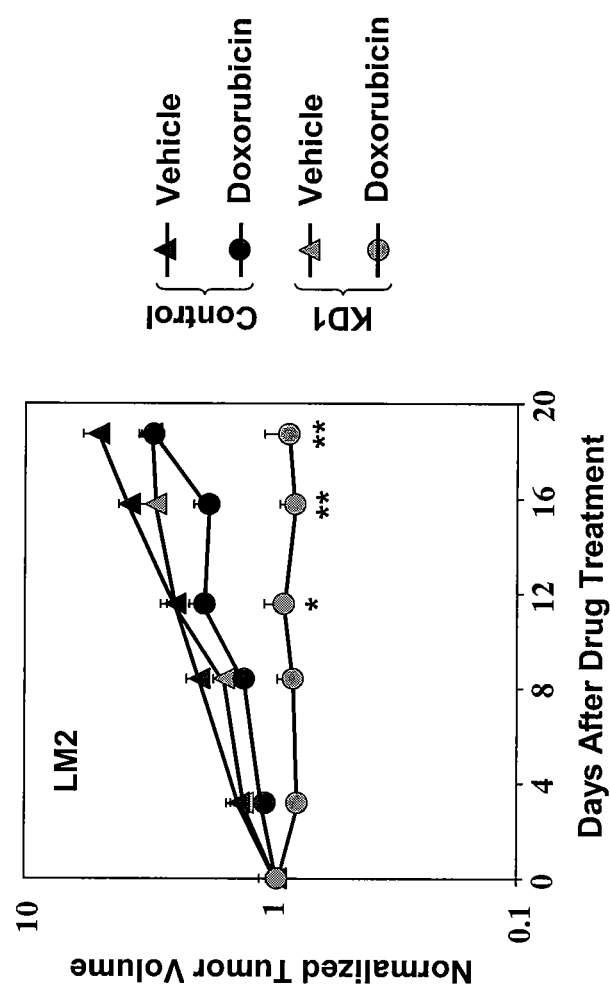
FIG. 11 depicts an in vivo chemoresistance assay with doxorubicin.

The chemoresistance function of MTDH was then examined in vivo using xenograft models. LM2 cells with or without MTDH knockdown were injected to nude mice subcutaneously. Twice-weekly treatment of tumors with paclitaxel or the drug vehicle was initiated at one week after injection. Subcutaneous tumor volumes were monitored by direct caliper measurement. When the mice were treated with the drug vehicle, the LM2 tumors grew rapidly, reaching five times the initial volume in 18 days after treatment (FIG. 9e). Tumors from the MTDH knockdown cells grew at an equal rate, an observation consistent with the finding that MTDH does not affect primary tumor growth (FIG. 8). Paclitaxel treatment significantly hampered tumor growth in mice injected with the control LM2 cells. However, the tumors still grew to 140% in volume 18 days after treatment, indicating a considerable degree of chemoresistance of these cancer cells. MTDH knockdown significantly sensitized the cells to paclitaxel treatment as tumor regression was observed immediately after the first treatment. The tumors eventually shrank to about 30% of the pre-treatment sizes 18 days after the initiation of treatment (FIG. 9e, f). Similar results were obtained with another commonly used chemotherapeutic agent doxorubicin (FIG. 11).

a) FIG. 9

Figure 10:
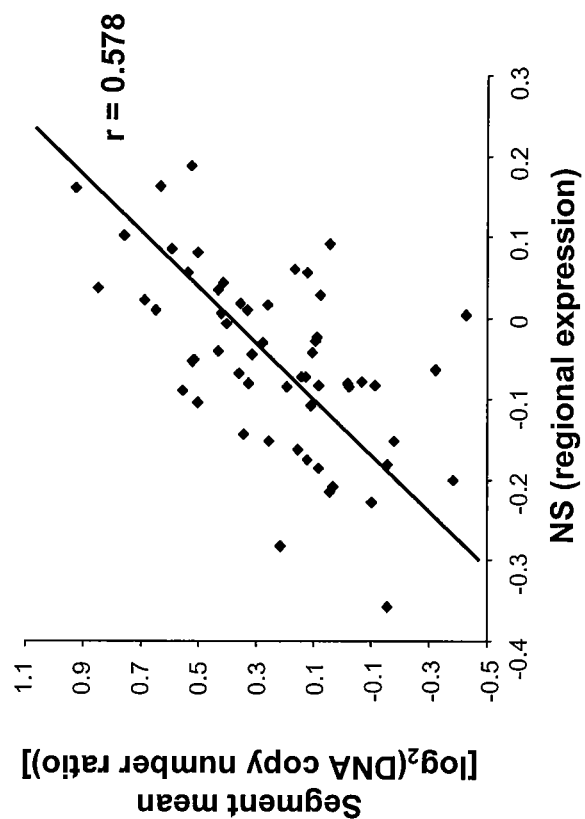
FIG. 10 depicts the correlation of 8q22 copy number in NS and NC160 cell lines.

FIG. 9 demonstrates that MTDH enhances chemoresistance of the breast cancer cells. FIG. 9a demonstrates that Genomic gain of 8q22 is associated with higher resistance to chemical compounds in the 58 human cancer cell lines. log $GI_{50}$ (drug concentration for 50% growth inhibition) of each of the 24,642 compounds in cell lines with 8q22 gain was compared to those in cells without 8q22 gain. The numbers of compounds with significantly increased log $GI_{50}$ in cells of 8q22 gain, counted by applying various significance thresholds of the log $GI_{50}$ differences (P<0.05, 0.01 and 0.001), was compared to a null distribution obtained by permuting the 8q22 copy numbers of the cell lines. Median values from permutations are shown with mean absolute deviation (MAD) as the error bar. FIG. 9b demonstrates the analysis of chemoresistance of LM2 cells using clonogenic assays after treatment with various apoptosis-inducing agents with or without HMVEC-L co-culture. Shown are the relative clonogenic abilities as percentages of the non-treatment control. FIG. 9c depicts representative images of the clonogenic assays for LM2 cells with or without MTDH-knockdown and HMVEC-L co-culture. FIG. 9d depicts clonogenic assays of SCP28 cells with overexpression of MTDH or other genes in the amplicon. Shown are the data with HMVEC-L co-culture. Results for FIGS. 9b and 9d represent average values±SEM of at least three independent experiments. In vivo chemoresistance assay of LM2 cells with or without MTDH knockdown. Shown are the xenograft tumor sizes when mice were treated with Paclitaxel or drug vehicle. 12 tumors per group were used. FIG. 9e depicts representative tumors isolated from the mice 25 days after injection in the in vivo chemoresistance assay. FIG. 9b, d, e *P<0.05; P<0.01; *P<0.001 with a two-sided student's t-test.

b) FIG. 10

FIG. 10 demonstrates the Correlation of 8q22 copy number in NS and NCI60 cell lines. 8q22 DNA copy numbers are positively correlated with the gene expression levels of this region in the 58 human cancer cell lines of the NCI60 data. The 8q22 copy numbers were analyzed from SNP microarray data using CBS algorithm and shown as the segment mean values. The overall 8q22 gene expression pattern is calculated as the neighborhood scores (NS) using ACE algorithm.

c) FIG. 11

FIG. 11 depicts an in vivo chemoresistance assay with doxorubicin treatment. Shown are the xenograft tumor sizes from control LM2 or MTDH-KD cells when mice were treated with doxorubicin or drug vehicle. 12 tumors per group were used. *P<0.05; **P<0.01 with a two-sided student's t-test to compare KD-1 cells with and without doxorubicin treatment. P=0.022 with Anova analysis of repeated measurement to compare the whole growth curves of these two conditions.

5. ALDH3A1 and MET Contribute to MTDH-Induced Chemoresistance

Figure 13:
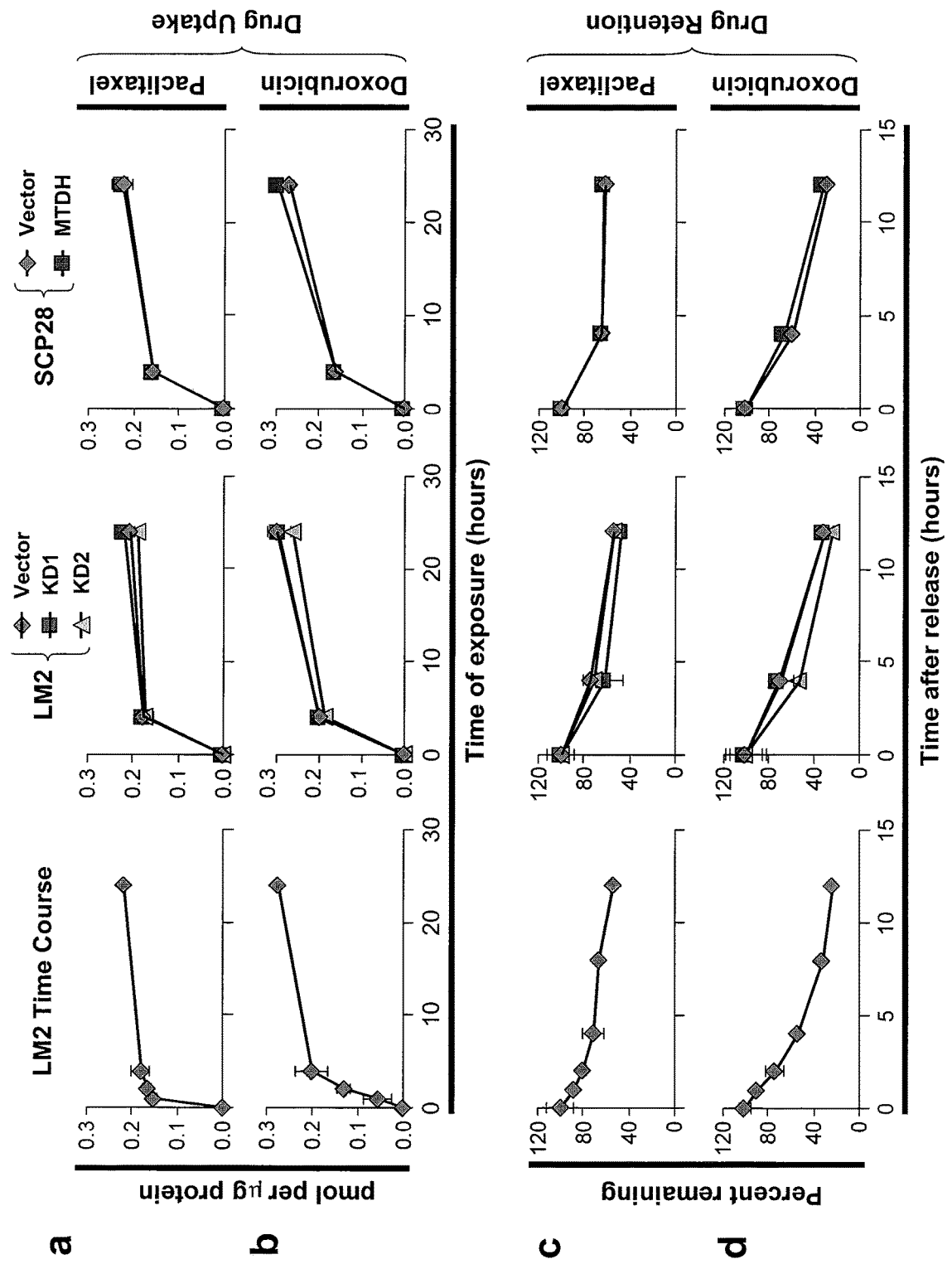
FIG. 13 depicts drug uptake and retention in cells with modified MTDH expression.

Drug uptake and retention assays using paclitaxel and doxorubicin in cancer cells with modified MTDH expression revealed that MTDH does not decrease drug uptake or retention in these cells (FIG. 13). Absent a direct function in altering drug accumulation, MTDH may increase chemoresistance by promoting cellular survival against antineoplastic stresses. To further elucidate the molecular mechanism of MTDH-dependent chemoresistance, gene expression profiles of two different MTDH-knockdown LM2 cell lines were compared with control cells. A similar comparison was also performed with LM2 cells co-cultured with HMVEC-L cells (FIG. 12a and Table 7). In the latter analysis, LM2 and HMVEC-L cells were labeled with GFP and the SNARF dye, respectively, to allow FACS-sorting of the two cell populations before RNA extraction (FIG. 12b). Since MTDH induces significant chemoresistance with or without HMVEC-L co-culture, attention was focused on genes that are consistently present in both conditions (>2.5 fold change in expression and student's t-test p<0.05). Twenty-three genes (including MTDH) were found to be under-expressed in MTDH-knockdown cells while 10 genes were overexpressed. Among the MTDH down-regulated genes (i.e. genes up-regulated following MTDH knockdown), are the cell death inducing genes TRAIL and BINP3. TRAIL encodes a TNF family cytokine that induces apoptosis in tumor cells. Combining TRAIL with conventional anticancer drugs has been showed to improve therapeutic efficacy of chemotherapies[44]. BNIP3 is a pro-apoptotic Bcl-2 family gene that has been shown to be involved in apoptotic, necrotic, and autophagic cell death[45]. Among the MTDH up-regulated genes are several genes previously implicated in chemoresistance of cancer cells, including ALDH3A1, HMOX1, HSP90AB1, HSP90AB3P, and MET. The Hsp90-family heat shock proteins have been shown to increase drug resistance by binding and stabilizing P-glycoprotein, which plays a prominent role in multi-drug resistance[46]. The Hsp90 inhibitor geldanamycin increases the sensitivity of resistant cancer cells to cisplatin[47]. Heme oxygenase-1 (HMOX1) is highly induced by a variety of stress stimuli and cancer chemopreventive agents, and represents a prime cellular defense mechanism against oxidative stress via antioxidant function of its catalytic products. Overexpression of HMOX1 in human cancers has been shown to confer cellular resistance against chemotherapy and photodynamic therapy[48]. The expression pattern of these candidate genes in MTDH knockdown cells was confirmed by qPCR analysis using samples from both cell cultures and xenograft tumors (FIG. 12c).

Among these candidate MTDH-downstream genes, ALDH3A1 (aldehyde dehydrogenase 3 family, member A1) and MET (hepatocyte growth factor receptor) are attractive targets due to their physiological functions and expression patterns. Antineoplastic agents have been shown to produce oxidative stress in tumors during cancer chemotherapy. The effects are mediated, in part, by the generation of aldehydes that result from oxidative stress-induced lipid peroxidation. ALDH3A1 encodes an anti-oxidant enzyme with several postulated protective roles that include, but are not limited to, detoxification of peroxidic aldehydes and scavenging of free radicals. Its expression has been implicated in clinical resistance to cyclophosphomide[49], a mainstay of chemotherapeutic regimens used to treat breast cancers. Interestingly, as revealed by microarray analysis (FIG. 12a) and further confirmed by qRT-PCR (data not shown), ALDH3A1 expression is 2 to 3-fold higher in the HMVEC-L co-culture as compared to the non-co-culture condition, while MTDH knock-down effectively represses ALDH3A1 expression in both conditions. Such an expression pattern matches the higher chemoresistance of cancer cells induced by HMVEC-L co-culture and chemosensitization by MTDH knock-down in both conditions. To investigate the functional importance of ALDH3A1 in MTDH-mediated chemoresistance, the LM2 cell line was engineered to express an inducible shRNA against ALDH3A1 to direct the conditional knockdown of ALDH3A1. LM2 cells were more sensitive to chemotherapeutic agent paclitaxel, doxorubicin and 4-hydroxycylcophosphamide (4-HC) when ALDH3A1 knockdown was induced by addition of doxycycline, while release of ALDH3A1 repression restored the chemoresistance of LM2 cells (FIG. 12d). Furthermore, the ability of ALDH3A1 to rescue the chemoresistance phenotype in MTDH knockdown cells was examined. Constitutive overexpression of ALDH3A1 in the MTDH knockdown cells was able to partially restore LM2 cell chemoresistance to paclitaxel and doxorubicin (FIG. 12e). Together, these results suggest that ALDH3A1 is one of the genes that mediate MTDH-induced chemoresistance.

The chemoresistance function of MET was also examined. In human patients, enhanced expression or activation of MET was observed in nearly all tumor types. In most cases, its expression is associated both with resistance to radiotherapy and chemotherapy, and with poor prognosis[50]. In experimental models, exogenous hepatocyte growth factor (HGF) or overexpression of MET induces resistance to ionizing radiation and many chemotherapeutics, including doxorubicin, cisplatin, etoposide, camptothecin, paclitaxel, TNF and gefitinib in diverse human cancer cells from different tumor types, as well as in endothelial cells[51, 52] MET knockdown in LM2 cells lead to a significant reduction of chemoresistance to doxorubicin, an effect that is similar to but weaker than that of MTDH knockdown (FIG. 12f), indicating that MET is among MTDH downstream genes that collectively contribute to its role in broad-spectrum chemoresistance. Indeed, when MET and ALDH3A1 were simultaneously knocked down in LM2 cells, the chemosensitizing effects reached a level comparable to that of MTDH knockdown (FIG. 12f).

a) FIG. 12

FIG. 12 demonstrates that ALDH3A1 and MET contribute to MTDH-mediated chemoresistance. FIG. 12a depicts expression pattern of the genes regulated in MTDH knockdown cells with or without HMVEC-L co-culture. Some genes previously implicated to promote (red) or suppress (green) cellular chemoresistance were highlighted. FIG. 12b depicts co-culture microarray experiment, HMVEC-L were pre-labeled with the SNARF dye and separated from GFP+ LM2 cells by FACS before microarray profiling. FIG. 12c depicts the confirmation of microarray data by qPCR. Shown are expression $\log_2$ (ratio) in LM2 MTDH-KD1 and KD2 cells as compared to LM2 control cells in culture and in xenograft tumors. Genes in red and green are those down- or up-regulated in MTDH knockdown cells identified by microarray study. FIG. 12d demonstrates that ALDH3A1 knockdown sensitized LM2 cells to chemotherapeutic treatment: (top) ALDH3A1 expression levels in cells engineered with ALDH3A1 inducible knockdown, (bottom) clonogenic ability of these cells. FIG. 12e demonstrates that ALDH3A1 overexpression partially rescues the cellular chemoresistance in MTDH knockdown cells: (top) ALDH3A1 expression levels in LM2 cells, (bottom) clonogenic assays. FIG. 12f demonstrates the effect of MET knockdown and MET/ALDH3A1 double knockdown on chemoresistance: (top) expression of MET and ALDH3A1 in LM2 cells, (bottom) clonogenic assays. FIG. 12d-f data represent average±SEM of three replicates. *P<0.05; **P<0.01 with a two-sided student's t-test.

b) FIG. 13

FIG. 13 depicts drug uptake and retention in cells with modified MTDH expression. Drug update assay of paclitaxel (FIG. 13a) and doxorubicin (FIG. 13b) in LM2 parent cells (left panel), LM2 vector control and MTDH knockdown (middle panel), and SCP28 cells with MTDH overexpression and vector control (right panel). Cells were treated with radiolabeled paclitaxel or doxorubicin for up to 24 hours and were harvested immediately after the indicated period of drug exposure. Drug uptake in the cells was measured by liquid scintillation counting. Results were normalized with cellular protein amount measured by Bradford assay and expressed as average±SD of three replicates. A drug retention assay for paclitaxel (FIG. 13c) and doxorubicin (FIG. 13d) in various cell lines as in Supplementary FIGS. 13a and 13b was performed. For the retention study, cells were incubated with drug-containing medium for 4 h, followed by incubation in 2 ml drug-free medium for the indicated time and then harvested. Drug retention in the cells was measured by liquid scintillation counting and normalized with cellular protein amount measured by Bradford assay. Results were expressed as percentage of remaining drugs as compared to the amount at the end of exposure to drug-containing media and shown as average±SD of three replicates.

6. MTDH Correlates with Poor-Prognosis in Clinical Samples

To evaluate the clinical importance of MTDH in breast cancer, the tissue microarrays used in the previous FISH analysis were examined with anti-MTDH antibody. Among the 170 samples on the tissue microarray, 47% expressed MTDH in a moderate to high level (FIG. 14a). The correlation of MTDH protein levels with 8q22 DNA copy numbers was analyzed using the samples that exhibited positive immunostaining and FISH results. While the data showed that all but one of the tumors with 8q22 amplification express abundant (medium or high) level of MTDH protein (FIG. 14b, chi-square test P<0.001), a substantial fraction (12%) of samples with normal DNA copy numbers also have a high level of MTDH protein. Therefore, alternative mechanisms distinct from 8q22 amplification may also result in MTDH activation in breast tumors.

Figure 15:
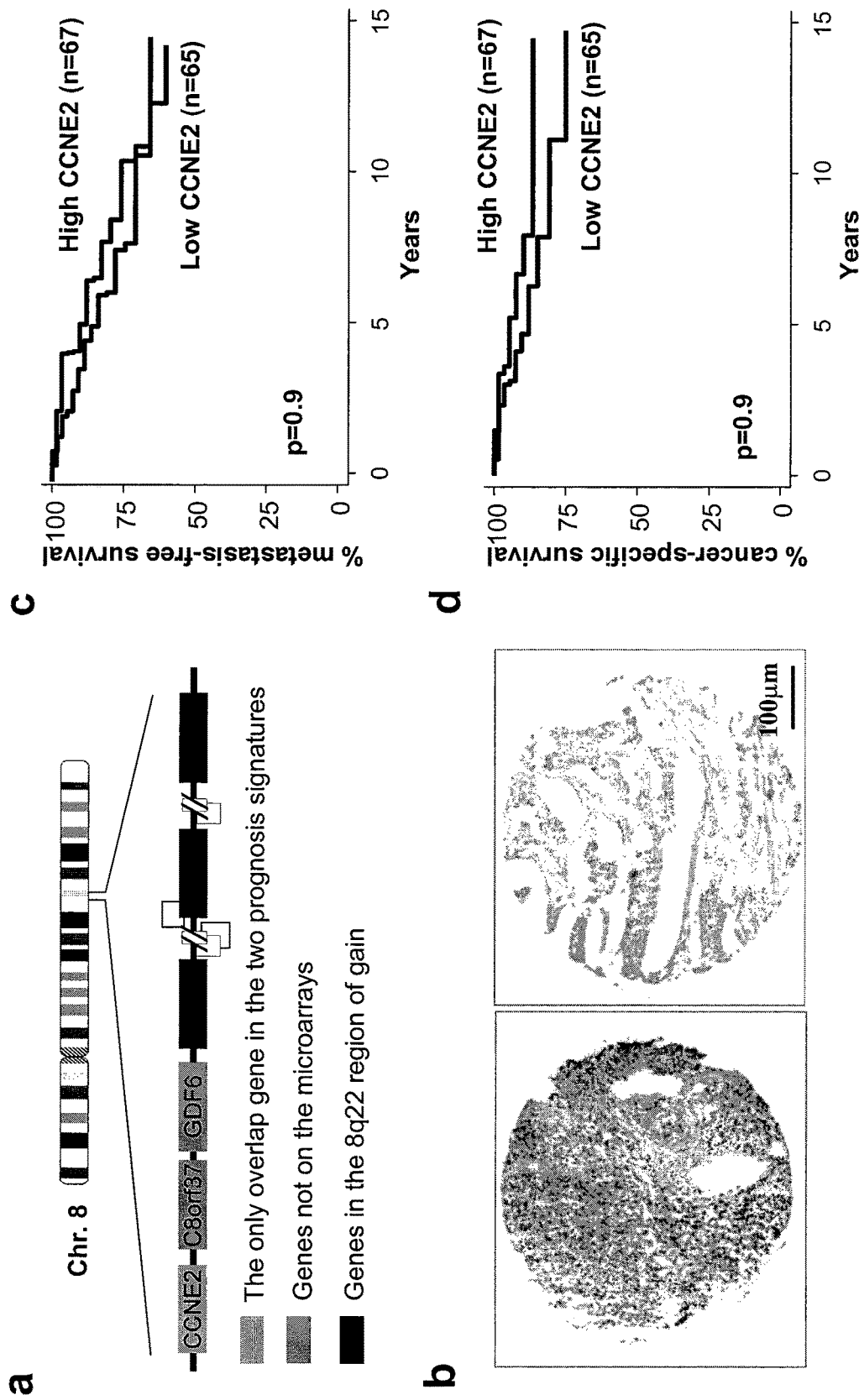
FIG. 15 demonstrates that CCNE2 is not associated with clinical outcomes in the breast cancer and tissue array analyses.

Importantly, MTDH expression is significantly associated with a higher risk of metastasis (log rank P=0.0058) and shorter survival time (P=0.0008). Univariate survival analysis using the Cox proportional hazard model also suggested that a high MTDH expression is strongly associated with a higher hazard ratio (HR) and worse clinical outcomes (HR=3.7, P=0.01 for metastasis; HR=8.3, P=0.005 for cancer-related death). Immunohistochemical analysis of CCNE2 protein expression (encoded by the only gene present in both poor-prognosis signatures identified by van't Veer et al. and Wang et al.) in the same breast tumor tissue array did not reveal any significant correlation with metastasis (FIG. 15). Interestingly, CCNE2 is located in very close proximity to the recurrent 8q22 genomic gain (FIG. 15). It is possible that the recurrent presence of CCNE2 in multiple poor-prognosis signatures is due to its close physical linkage to 8q22.

Figure 14:
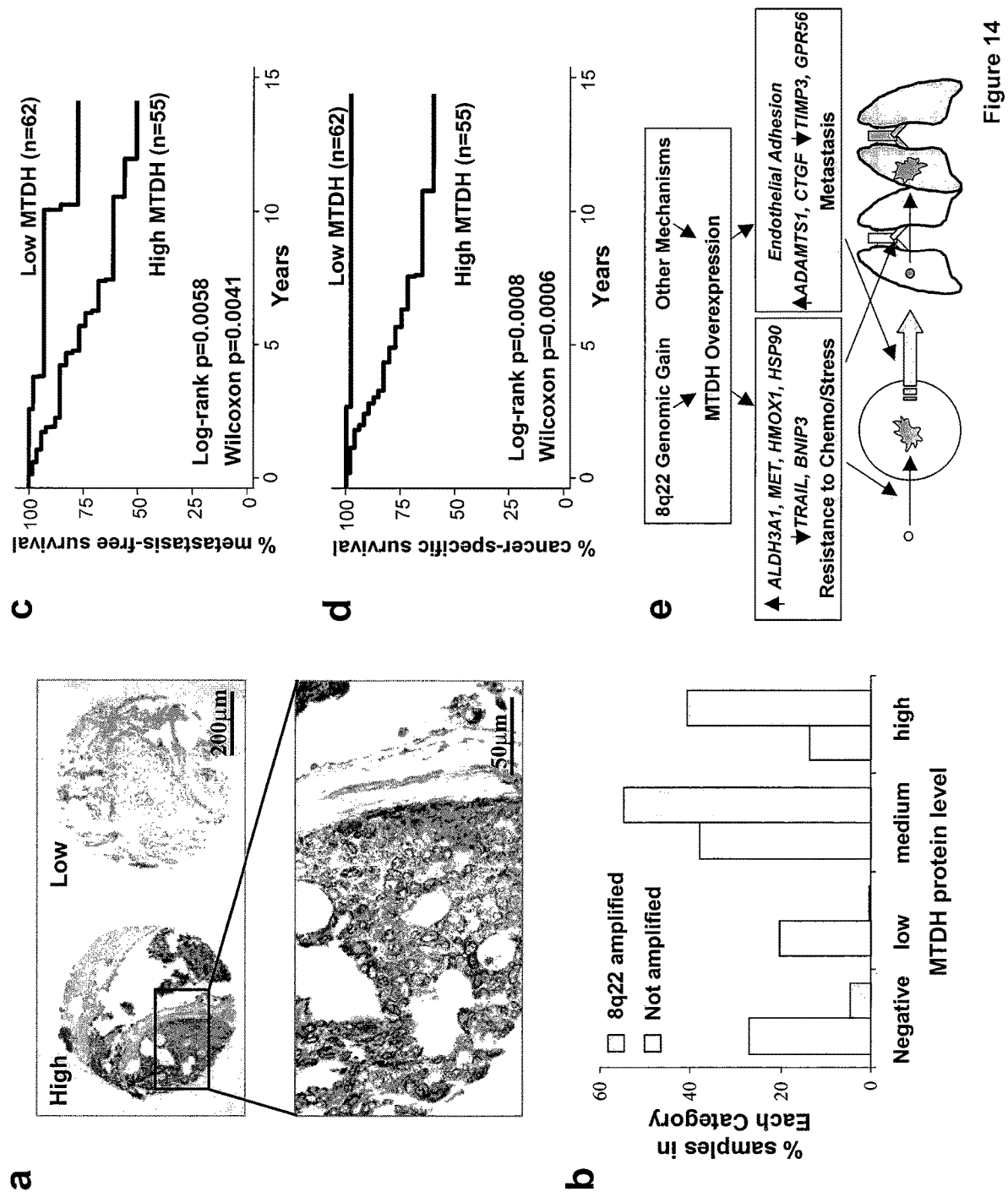
FIG. 14 demonstrates that MTDH is associated with poor-prognosis of human breast tumors.

To further analyze the prognostic significance of MTDH expression compared to other commonly used clinicopathological parameters, a Cox hazard ratio analysis of MTDH expression was performed with the tissue samples stratified by ER, PR, HER2, and p53 status as well as the sizes of primary tumors at the time of cancer diagnosis (Table 8). MTDH expression level retained its prognostic significance in these analyses, suggesting that it is a prognostic factor independent of other clinicopathological factors. Indeed, a multivariate Cox analysis combining all of the above parameters with MTDH expression showed that the hazard of metastasis was still significantly higher with MTDH expressed (P=0.023) even when all the other factors were considered.

a) FIG. 14

FIG. 14 demonstrates that MTDH is associated with poor prognosis of human breast tumors. FIG. 14a depicts MTDH immunostaining with a human breast cancer tissue microarray. Shown are typical images of positive and negative staining. FIG. 14b demonstrates that MTDH protein levels are positively correlated with the FISH 8q22 DNA copy numbers. FIG. 14c demonstrates that high MTDH protein level in tumors is associated with early metastasis in cancer patients. FIG. 14d demonstrates that high MTDH expression is also linked to worse cancer-specific survival. FIG. 14e provides a schematic model for the dual role of MTDH in breast cancer progression. In poor-prognosis tumors, 8q22 genomic gain leads to overexpression of MTDH, which in turn activate two parallel programs to promote chemoresistance and metastasis. Elevated expression of chemoresistance genes ALDH3A1, MET, HMOX1 and HSP90, as well as repression of apoptosis inducing genes TRAIL and BNIP3 promote the survival and outgrowth of cancer cells in the primary site as well as secondary organs in the face of physiological stress and chemotherapeutic challenges. MTDH additionally promotes metastasis by mediating tumor cell adhesion through the interaction with unknown receptors and by activating pro-metastasis genes and suppressing metastasis suppressive genes. Some of the molecular mediators of the MTDH function may play a role in both functional categories. For example, MET can promote both metastasis and chemoresistance, and endothelial adhesion can further enhance MTDH-mediated chemoresistance.

b) FIG. 15

FIG. 15 demonstrates that CCNE2 is not associated with clinical outcomes in the breast cancer tissue array analysis. FIG. 15a shows that CCNE2 is the only overlapping gene in the poor-prognosis gene signatures by van't Veer et al. and Wang et al., and is located immediately upstream of the 8q22 region of gain. Supplementary FIG. 15b shows a human beast cancer tissue array was stained with an anti-CCNE2 antibody. A case of high CCNE2 expression (left) and a case of low CCNE2 expression (right) are shown (FIG. 15c). FIG. 15d depicts Kaplan-Meier analysis of patient metastasis and survival shows no significance of CCNE2 expression.

II. Methods

1. Development of the Analysis of CNAs by Expression (ACE) Algorithm

ACE detects genetic alterations in three steps: 1) calculating neighborhood scores (NS) for each chromosomal locus as an indicator of CNA likelihood at that locus, 2) estimating the significance of the NS, and 3) defining the regions of gain and loss. The expression score (ES) for each gene is first calculated according to the correlation of its expression with the phenotypes in comparison. Paired t-statistics (for ovarian cancer cell lines) or independent t-statistics (for other datasets) were used to score gene expression. In general, other metrics can also be used. Consider the genes 1, 2, . . . , N on a chromosome ordered by their physical positions. The NS at locus i was defined as the weighted sum of the ES of this chromosome:

$$NS_i = \sum_{j=1}^{N} w_{ji} ES_j$$

where $w_{ji}$ is the weight of gene j. Because the linkage strength between two loci becomes weaker as the distance increases, the weight $w_{ji}$ decreases when locus j is farther way from the locus i. The contribution from each gene is weighted by a Gaussian function.

$$w_{ji} = ce^{-(j-i)^2/2\sigma^2}$$

where c is a constant to normalize all NS into a range of [−1, 1]. The variation parameter $2\sigma^2$ controls the weight decay rate and is arbitrarily set to 100 in the analyses presented here. An analysis using varying $2^2$ values from 20 to 200 showed similar results with slight shifts at the boundaries of detected regions. For each locus, only the genes in its physical proximity will have measurable influence on its NS because of weight decay. Positive and negative NS suggest genomic gain and loss, respectively. To evaluate the significance of the NS, the gene positions (or sample class labels if the sample size is large enough) are permuted 1,000 times, and each time the NS are recomputed. The p values of observed NS are then computed using the distribution of permuted NS and adjusted to FDR-q values by the Benjamini-Hochberg procedure (herein incorporated by reference). In all the CNA analyses presented in this manuscript, a region of genomic gain is defined as having at least 20 continuous positive NS of FDR-q<0.01, or a region of genomic loss when such NS are all negative. In the epigenetic analysis, a cutoff of 5 continuous NS is used, since epigenetic regulation usually has a smaller functioning range.

Several approaches have been previously reported for CNA prediction based on expression microarray data[65-70]. The majority of these approaches utilized an intuitive "odd-ratio" like method, in which the individual genes were first defined as significant or not significant by a cutoff of the expression correlation with the phenotype, and the densities of the significant genes were analyzed for each region with a pre-chosen width. The regions with aberrantly high densities were predicted as regions of gain or loss. Analyses with several expression datasets have shown that the "odd-ratio" approach with different significance cutoffs and window sizes generated quite inconsistent results, and therefore was not suitable for large-scale analysis of multiple datasets. ACE can be distinguished from these previous approaches by several features including: 1) A quantitative expression score, instead of the binary significant/non-significant flag of each gene is used for the regional analysis, which evades the problem associated with the arbitrary significance cutoff; 2) A position-dependent weight is employed for each neighboring gene of the locus in consideration, which represents a comprehension of the fact that linkage strengths decrease with physical distances; and 3) All the genes on the chromosome, instead of those within an arbitrarily pre-chosen window size, were analyzed for each genomic locus. These features increase the sensitivity and the robustness of the algorithm.

2. Validation of ACE in Various Datasets

To validate the ACE approach, several published expression datasets with the corresponding information of genomic alterations or long-range epigenetic regulation were analyzed. For each expression dataset with probe detection flags available, the genes that were flagged as "absent" in more than 90% of the samples were removed from further analysis. Duplicate probes mapped to the same transcripts were collapsed and the average expression intensities were used. Expression data were normalized for each study so that each hybridization had equal median intensity across the entire array. Student's t-test was used to score the gene expression prior to NS calculation. To avoid possible bias, dataset-specific optimization of ACE analysis was not performed; a uniform set of pre-defined analysis parameters was used instead.

Gene expression data was first analyzed using the Ts1Cje mouse[71], the animal model for human Down Syndrome and hosts a partial trisomic region from gene Sod1 to Znf295 on chromosome 16. Affymetrix microarray expression data of Ts1Cje and normal mouse brain tissues were downloaded from the NCBI GEO database (accession number GSE1294). Genes were scored by the expression difference between trisomic and normal mice followed by NS calculation. ACE detected only one region of gain and no regions of loss in trisomic mice. The significant region overlapped precisely to the expected area (FIG. 2a). The first p-distal boundary in the detected region corresponds to the gene Mylc2b, which is immediately adjacent to Sod1 on the chromosome. The second expected boundary gene Znf295 is located q-distal of all the probes available on the microarray and ACE consistently defined the region to the end of the q arm.

ACE was then used to analyze gene expression of taxane-resistant ovarian cancer cells compared to the parental lines[72]. Results were validated with the CGH data for the same samples. The expression and CGH data of 6 human ovarian cancer cell lines and their taxane-resistant derivatives were obtained from the Stanford Microarray Database (http://genome-www5.stanford.edu; herein incorporated by reference). ES were scored according to the expression difference of each gene between the parental and drug-resistant lines prior to NS calculation. To avoid bias, the same method was used as in the original paper, circular binary segmentation (CBS)[73], to analyze the CGH data. CBS analysis detected 3 regions on chromosome 7 with increased copy numbers in the drug-resistant lines, which was consistent with the previous finding[72]. ACE detected the same areas as the only significant regions (FIG. 2b). In addition to these significant regions, high concordance was observed between the NS and the CBS copy number data throughout the genome. The overall correlation between the NS and CGH data was 0.55 (Pearson's correlation coefficient), whereas the correlation was only 0.16 if the original expression scores were used, suggesting that NS can significantly help uncover the correlation between gene dosage and expression. From the correlation data, it was determined that approximately 30% of all variation observed in NS could be directly explained by the underlying variations in genetic copy number[31].

ACE was further examined using more complicated data from MDA-MB-231 cell sublines with different degrees of breast-to-bone metastatic activities[9]. Expression profiles of 5 highly metastatic lines (2268, 2269, 2271, 2274, 2287, 1833) and 5 weakly metastatic lines (2297, 1834, 2293, 2295, ATCC) were compared using ACE. This analysis detected 5 CNA events, including gain at 2p, 6p, 12q, 19q and loss at 7q, in metastasis. CGH analysis was performed as previously described[9] on these cell lines to validate the computational analysis. Four out of these 5 genetic events had been directly observed in the cytogenetic analysis. For example, consistent with the ACE prediction, CGH data indicated a loss at the q arm of chromosome 7 in highly metastatic cells (FIG. 2c).

Long-range epigenetic alteration may also contribute to regional gene deregulation. To test ACE's capability to detect such changes, a dataset of 57 bladder tumors[70] was analyzed; this analysis detected 22 regions with genes under expressed in tumor tissues as compared to normal samples. Analysis of the CGH data revealed that 15 of these regions were lost in more than 10% of the tumor tissues, but gained in significantly fewer tumors (binomial P<0.05), indicating that genomic loss of these regions was associated with bladder carcinomas. Furthermore, 4 of the remaining regions were proven or suggested by Stransky et al. as regions under epigenetic control[70] (Table 4). For example, a region at 3p22.3, was shown to be regulated by histone H3 trimethyl modification in tumor samples[70] (FIG. 2d).

3. Identification of Poor-Prognosis-Associated CNAs in Breast Cancer

Three published breast cancer datasets[14-16] were examined in search of metastasis-associated CNAs in breast cancer. The microarray data and patient records of the tumor samples were obtained from GEO (Wang, GSE2034), and Rosetta websites (van't Veer, http://www.rii.com/publications/2002/vantveer.html); and van de Vijver (http://www.rii.com/publications/2002/nejm.html). Some of the samples in the van de Vijver study had been previously used in the van't Veer dataset and thus were removed from the van de Vijver dataset to avoid bias. Gene expression was compared between the patients developing metastasis within 5 years and those free of metastasis for more than 5 years. Metastasis-specific CNA regions were identified in each dataset and the SRO regions that were identified in more than one dataset were defined as the consensus poor-prognosis CNAs. To analyze the prognostic power of the copy number at each SRO region, the NS of the center locus were calculated for each sample using the z-score like expression scores. All the samples were classified into two groups using a NS cutoff so that the number of samples in the high NS group was equal to the number of samples with 5-year relapses. The clinical outcomes were analyzed by comparing the samples in the two groups (Table 3).

4. Laser Capture Microdissection (LCM) and DNA/RNA Extraction

To quantify DNA copy number and expression of genes at 8q22 in clinical breast tumor specimens, laser captured microdissection (LCM) was performed to isolate tumor cells from each tissue specimen. A panel of 50 snap-frozen breast tumors from anonymous patients was used in this study. These samples were examined by H&E staining; only those with approximately >50% tumor cells were selected for LCM followed by DNA and RNA extraction. The quality of DNA/RNA preparation was monitored by O.D. reading, leaving 36 high-quality samples for analysis. Another panel of 50 formalin-fixed paraffin-embedded tissues from anonymous patients was examined for MTDH expression by immunohistochemistry, and 20 samples were selected with strong or negative MTDH staining for microdissection followed by DNA extraction. Two of these samples failed in the DNA preparation step and thus 18 samples were used in the analysis.

For each sample, sequential sections of 15 μm thickness were prepared for LCM. The sections were mounted on the glass PEN-membrane slides (Leica) and stained using the Histogene staining solution (Arcturus) following the manufacturer's protocol. Slides were then immediately transferred for microdissection using a Leica AS LMD microscope. Approximately 10,000 tumor cells were prepared for DNA purification for each sample. For the fresh tumors, a separate sample of ~10,000 tumors cells was collected in 20 μl of RNAlater stabilization reagent (Qiagen) for RNA extraction.

DNA extraction was performed as previously described[74] with or without the paraffin-dissolving step for archived and fresh tumors, respectively. The RNeasy mini kit (Qiagen) was used to extract RNA from the tumor samples according to the manufacturer's instructions.

5. Real-Time PCR and Data Evaluation

To analyze the DNA copy numbers, primer pairs were designed using the intron sequences of genes at chromosome 8q, including CA2 (8q21), LAPTM4β and MTDH (8q22), and EIF3S6 (8q23). Real-time PCR and data analysis were performed essentially as previously described[75,76] Briefly, primers were designed using the software PrimerExpress (Applied Biosystems). PCR was performed using CyberGreen Universal PCR Master Mix (Applied Biosystems) with the ABI Prism 7900HT thermocycler (Applied Biosystems) according to the manufacturer's protocol. The absolute DNA copy number of each sample was analyzed with SDS 2.0 software (Applied Biosystems) using standard curves of known concentrations. The gene APP, located at 21q21 for which no amplifications in breast cancer have been reported, was used as the internal reference locus[75,76]. The copy numbers of the samples were normalized by healthy human tissue DNA. The previously used copy number ratio threshold 1.8 was applied to define a genomic gain[75,76].

qRT-PCR was performed to analyze the RNA level of genes at 8q22, including MTDH, LAPTM4β and PTDSS1 in fresh tumors following reverse transcription using the SuperScript first-strand synthesis kit (Invitrogen). The β-actin control kit (Applied Biosystems) was used for normalization. Primer sequences are listed in Table 9.

6. Fluorescence In Situ Hybridization (FISH)

Tissue FISH was performed by the Dana-Farber Cancer Institute Cytogenetic Core Facility. One microgram of DNA from the BAC clone RP11-662P7 (Children's Hospital Oakland Research Institute), which covers the MTDH locus and other areas at 8q22 was labeled using the Nick Translation kit and SpectrumOrange dUTP (Vysis) following the manufacturer's protocol. Chromosome enumeration probe CEP8 labeled with SpectrumGreen (Vysis) was used for centromere 8 hybridization. Paraffin-embedded tissue slides were pretreated with xylene, dehydrated and digested with Digest-All 3 (Zymed). The slides were then washed in 1×PBS, fixed in formalin, and dehydrated in ethanol. Probes were added onto the slides and denatured at 94° C. for three minutes. Hybridization was performed at 37° C. in a humidified chamber. Forty-eight hours later the slides were washed in 2×SSC at 72° C. and phosphate buffered tween-20 solution at room temperature, and counterstained with DAPI. Hybridization signals were viewed on a fluorescence Olympus BX-51 microscope system. For each sample 50-100 nuclei were analyzed and the average 8q22 copy numbers were calculated. Eighty-two of the 170 samples on the tissue microarray with successful hybridization were analyzed and scored by the staff of the Cytogenetic Core at Dana Farber Cancer Institute.

7. Generation of Knockdown and Overexpression Cells

MTDH, ALDH3A1 and ME knockdown was achieved with the pSuper-Retro system with puromycin or hygromycin selection markers (OligoEngine) using the following sequences: 5'-GGCAGGTATCTTTGTAACTA-3' (MTDH KD1), 5'-GCTGACTGATTCTGGTTCAT-3' (MTDH KD2), 5'-CGCTACTTATGTGAACGTAA-3' (MET) and 5'-GGT-TCGACCATATCCTGTA-3' (ALDH3A1). shRNA retroviral vectors were transfected into the amphotropic Phoenix packaging cell line and viruses were collected, filtered and used to infect target cells in the presence of 5 μg/ml polybrene 48 h after transfection. The infected cells were selected with 0.5 μg/ml puromycin or/and 0.4 mg/ml hygromycin. Double knockdown of MET and ALDH3A1 was achieved by simultaneous infection of MET and ALDH3A1 targeting viruses with different drug selection markers. MTDH, LAPTM4b, PTDSS1, SDC2, TSPYL5, and UQCRB overexpression was achieved using the retroviral expression vector pBabe-hygro. Viruses were generated and used to infect target cells as above and the infected cells were selected with 0.4 mg/ml hygromycin. For combinational overexpression of genes at 8q22, the viruses generated from the expression vector pBabe-puro containing each of the four genes were concentrated by ultracentrifugation and pooled for infection. Northern blots, qRT-PCR, and/or Western blots were performed to validate the knockdown or overexpression of target genes.

To generate an inducible knockdown of ALDH3A1, a retroviral vector expressing the Tet repressor (TetR) was constructed by cloning the TetR coding sequence from the pcDNA6/TR plasmid (Invitrogen) to pQCXIH (Clontech). LM2 cell line with stable expression of TetR was generated by transduction with retroviruses produced from pQCXIH-TetR. The cell line was then infected with retroviruses generated from the pRSMX vector[77] containing the ALDH3A1-targeting shRNA sequence. The expression of a shRNA against ALDH3A1 is under the control of the histone H1 promoter and two adjacent tetracycline operators (TetOs). The bacterial Tet repressor (TetR) is constitutively expressed from the integrated pQCXIH-TetR in this cell line and suppresses the expression of shRNA by binding to TetOs. In the presence of 1 g/ml doxycycline in the media, TetR is released from the TetOs and allow the transcription of ALDH3A1 shRNA and thus the repression of ALDH3A1 expression. The pBabe-hygro vector was used to overexpress ALDH3A1.

8. Tumorigenesis and Metastasis Assays in Nude Mice $2 \times 10^5$ cells were washed in PBS and injected intravenously to female athymic Ncr-nu/nu mice to study the lung metastasis activity as previously described[11]. For bone metastasis analysis, $1 \times 10^5$ cells were injected to the left ventricle of the animal heart as described[9]. Noninvasive bioluminescence imaging was performed to quantify the metastasis burden at the target organs using the IVIS 200 Imaging System (Caliper Life Sciences) as previously described[11].

To study primary tumorigenesis, cancer cells harvested from culture were resuspended in PBS at a concentration of $1 \times 10^7$ cells/ml. An incision was made in the abdomen and the skin was recessed to locate the #4 mammary fat pad, into which $10^5$ cells (10 μl) were injected under a dissection microscope. The primary tumor volume was monitored weekly as previously described[11].

9. In Vivo Chemoresistance Assay

MTDH-knockdown or control LM2 cells ($1 \times 10^6$ cells/0.1 ml in a 50:50 solution of PBS and Matrigel) were injected subcutaneously into each flank of nude mice. The mice were treated with chemotherapeutic drugs (20 mg/kg paclitaxel or 5 mg/kg doxorubicin) or the corresponding drug vehicles (Cremophor for paclitaxel and saline for doxorubicin) twice a week by intravenous delivery a week after the tumor xenografting. Six mice (12 tumors) were used for each group. Tumor growth was monitored twice a week by size measurement. Both maximum (L) and minimum (W) diameters of the tumor were measured using a slide caliper, and the tumor volume was calculated as $\Box LW^2/6$. Tumor growth was normalized to that before drug treatment.

10. Lung Histology

Mice were sacrificed and lungs were harvested followed by fixation in 10% neural buffered formalin overnight, washing with PBS and dehydration in 70% ethanol. Tissue paraffin-embedding, sectioning and H&E staining were performed by Histoserv, Inc. (Germantown, Md.).

11. Wound Healing Assay

Cancer cells were grown in 10 cm culture dishes to confluence. A "wounding" line was scratched into the cell monolayer using a sterile pipet tip and its width was measured under microscope. The width was measured again at the same place after 3 h of culturing. The migration distance was defined as half of the difference between the scratch widths before and after the culturing period. Six measurements of each cell line were made and a student's t-test was performed to compare the migration capacity of different cell lines.

12. Two-Chamber Migration Assay $10^5$ luciferase-labeled cancer cells in serum-free medium were seeded into the upper chamber of the insert membranes with a 3 μm pore size (BD Bioscience) in a 24-well plate. Serum-containing medium was used in the bottom chamber as the attractant. After 12 h of culturing the cells in the upper chamber were removed using a cotton swab. The insert membrane with trans-well cells was cut off with a blade and added into a tube with cell lysis buffer. The cell numbers were quantified using a luciferase assay and the luminescence intensities of each line were normalized to that of $10^5$ cells. A luciferase signal standard curve of each line with $10^2$ to $10^5$ cells was generated for quantification.

13. Matrigel Invasion Assay

Invasion assays were performed essentially as the above migration assay procedure except that the insert membrane was coated with a Matrigel (BD Bioscience) monolayer before cell seeding. Invasion index of each cell line was calculated as the fraction of trans-well cell number divided by that obtained in the migration assay.

14. Endothelial Adhesion Assay

To test the adhesion of cancer cells to the endothelial cells, different endothelial cell lines (HBMEC-60, from bone marrow; HUVEC, from umbilical vein; HMVEC-L, from lung microvascules) and a control fibroblast cell line WI-38 were grown to confluence in a 24-well plate. $10^5$ luciferase-labeled cancer cells were seeded onto the endothelial monolayer. After 3 h of culturing, the unbound cells in the supernatant were removed by washing 3 times with PBS and the attached cancer cells were harvested by trypsinization. The cell number was quantified by luciferase assay as described above.

15. Chemoresistance Clonogenic Assay

Cancer cells with genetic modification of MTDH and/or ALDH3A1 and the vector control were seeded into a 48-well plate ($10^4$ cells/well). After 24 h, the cells were treated with apoptosis-inducing chemicals for the indicated time (20, 50 or 100 nM paclitaxel, EMD Biosciences, 24 h; 50, 100 or 200 μM doxorubicin, EMD Biosciences, 24 h; 40 μM cisplatin, EMD Biosciences, 2 h; 200 or 500 μM $H_2O_2$, Fisher Scientific, 2 h) or 10 mJ/cm$^2$ UV irradiation. After culturing in drug-free DMEM medium for another 48 h, the surviving cells were quantified by clonogenic assay with the standard procedure for long-term recovery. Briefly, an aliquot of the harvested cell population was seeded onto a 10 cm dish. Crystal violet staining was used to count the colonies after 10-day culture in DMEM medium. The colony numbers from untreated cells of the same line were used to normalize the experimental data. In the HMVEC-L co-culture assays, HMVEC-L cells were grown to confluence in the 48-well plates with supplemented EGM-2 medium (Lonza) before seeding of cancer cells. Because HMVEC-L cells could not form colonies in the DMEM medium (data not shown), the rest of the assay was performed following the standard procedure.

16. Drug Uptake and Retention Analysis of Paclitaxel and Doxorubicin

Cells were seeded into 12 well plates at densities of $3 \times 10^5$ per well in 1 ml of culture medium. One day after seeding, the medium was replaced with 1 ml of medium containing 50 nM [$H^3$]-Paclitaxel (Moravek, 2 Ci/mmol) or 100 nM [$C^{14}$]-Doxorubicin (GE HealthCare, 56 mCi/mmol). A pilot study showed biphasic kinetics in the uptake and retention of paclitaxel and doxorubicin in the parent LM2 cells. Based on this data, 4 and 24 h time points were selected for comparison of drug uptake and 4 and 12 h for comparison of retention, in all derivative cell lines. For the uptake study, cells were harvested immediately after incubation with drug-containing medium. For the retention study, cells were incubated with drug-containing medium for 4 h, followed by incubation in 2 ml drug-free medium and then harvested. After washing with cold PBS, the pelleted cells were lysed with 200 ul of 0.1N NaOH. An aliquot (5 ul) was used to determine the protein concentration by Bradford assay (Sigma-Aldrich) with BSA as standards. The remaining cell lysates were transferred to scintillation count vials and mixed with 4 ml ECoScint scintillation fluid (National Diagnostics) and the radioactivity was measured by liquid scintillation counting. A standard curve was established and used to calculate the amount of cell-associated drug.

17. Endothelial Co-Culture. FACS and Microarray Analysis

HMVEC-L cells were grown to confluence in 150 mm culture dishes and washed once with PBS before SNARF labeling. The cells were cultured in serum-free EGM-2 medium containing 10 μM SNARF (Molecular Probes) at 37° C. for 30 min followed by washing with PBS twice. $2 \times 10^6$ GFP-labeled LM2 control or KD1 cells were seeded into the plate in serum-containing DMEM medium. Cell sorting was performed in the Princeton Flow Cytometry Core Facility to purify the GFP$^+$ LM2 cells by using a FACSVantage SE cell sorter (BD Biosceinces) 48 h later (FIG. 12b). Cells were collected in RNAlater solution (Qiagen) and RNA extracted with RNeasy mini kit (Qiagen). The quality of purified RNA samples was monitored using a 2100 bioanalyzer (Agilent) before expression profiling.

To identify genes regulated by MTDH knockdown, RNA samples of LM2 control and MTDH-KD cells with or without HMVEC-L co-culture were analyzed with the Agilent Whole Human Genome 4×44k arrays. RNA samples were labeled with Cy5 with the Agilent Low RNA Input Linear Amplification Kit and were hybridized with the Cy3-labeled Human Universal Reference RNA (Stratagene). Triplicate arrays were performed for each sample. Arrays were scanned with an Agilent G2565BA scanner and analyzed with the Agilent Feature Extraction v9.5 software. The Cy5/Cy3 ratios were calculated using the feature medium signal and normalized by the array median. Microarray data were deposited into the NCBI GEO database with an accession number GSE9187. Probes with >2.5 fold changes and student's t-test p values<0.05 in both culturing conditions were identified as the MTDH regulated genes. Several significant genes, including ALDH3A1, MET and HMOX1 were randomly selected for qRT-PCR confirmation with the RNA samples used for microarray analysis. RNA samples prepared from cells after the same FACS procedure but without HMVEC-L co-culture were also analyzed by qRT-PCR to rule out the possibility that the expression differences were an artifact of the sorting procedure.

18. Tissue Array Immunostaining

A breast cancer tissue microarray composed of 170 primary tumors was used in the clinical study. At the time of tumor resection, the patients were at an age of 25 to 49 years (median=40 yrs, SD=4.7 yrs). All patients in the study were treated with breast conserving surgery followed by radiation therapy to the intact breast. Systemic therapy was administered as clinically indicated in accordance with standard clinical practice. Local or regional relapses were defined as clinically and histologically documented relapses in the ipsilateral breast or regional nodes. Distant metastases were defined as clinical evidence of distant disease based on clinical and/or radiographic findings (Table 6).

Immunostaining was performed at the immunohistochemistry core facility of the Cancer Institute of New Jersey (CINJ) with a rabbit monoclonal anti-MTDH antibody (Invitrogen) and a rabbit polyclonal anti-CCNE2 antibody (Imgenex). A BLAST search of the antigen sequence used to raise the anti-CCNE2 antibody was performed to ensure it does not cross-react with other cyclin E family members. Out of the 170 samples, 117 samples were stained successfully for MTDH and 133 samples for CCNE2. Each sample was scored as negative (0), low (1), medium (2), or high (3) according to staining intensities. A Kapan-Meier curve was used to compare the survival rates of patients with low (scores 0 and 1) and high (scores 2 and 3) levels of MTDH or CCNE2. Log rank and Wilcoxon tests were used to compare the differences between curves using the SAS statistical software package. To assess whether the MTDH prognosis significance was associated with the other clinicopathological factors, Cox analysis of MTDH stratified with the expression status of ER, PR, HER or p53 (negative or positive), or the primary tumor sizes (smaller or larger than 2 cm) was performed. Multivariate Cox analysis with all the parameters in assessment was also undertaken to analyze the dependence of MTDH significance on other parameters.

19. Pharmacologic Data Analysis

The pharmacological dataset was downloaded from the NCI website http://dtp.nci.nih.gov, where the −log $GI_{50}$ of 42,796 small molecules and natural products, as well the SNP microarray data were available for 58 human tumor cell lines[43]. $GI_{50}$ was defined as the drug concentration necessary to inhibit cell growth by 50%. The SNP genotyping data were analyzed with the CBS algorithm[73]. A segment mean value of 0.4 was used as the threshold to define regional gain at the 8q22 region. Fifteen (26%) out of the 58 cell lines were classified as having a gain. Multiple −log $GI_{50}$ entries of each compound were filtered as described[43]. The compounds were further filtered to exclude those with $GI_{50}$ data in less than 50 cell lines. This yielded a total of 24,642 compounds for further analysis. The log $GI_{50}$ mean difference of each compound in the cells with and without 8q22 gain was calculated, and the significance of this difference was estimated by 1,000 permutations of the 8q22 status in the cell lines. The numbers of compounds with higher $GI_{50}$ associated with 8q22 gain were counted by applying a significance threshold (0.05, 0.01, or 0.001, etc.) of $GI_{50}$ difference and were compared to the permutations. Although the Affymetrix U95v2 expression data were also available for these cell lines, the only MTDH probe showed very low signal intensities for all the samples probably due to a probe failure. Therefore, no further analysis was performed with the MTDH expression data. Instead, the association of 8q22 copy number with gene expression was assessed by calculating a NS from the expression of genes in this region for each cell line as described earlier. A Pearson's correlation coefficient was calculated between the NS and the copy number.

20. Statistical Analysis

The Kaplan-Meier method was used to estimate survival curves for the patients and animals. Log rank test and Wilcoxon test were used to compare the differences between curves. Two-sided Wilcoxon rank test was performed to analyze the bioluminescent imaging results in the in vivo studies. A two-sided independent student's t-test without equal variance assumption was performed to analyze the results of luciferase assays and clonogenic assays.

We claim:

1. A method of treating a cancer in an individual, comprising:
   (a) administering to the individual an effective amount of a chemotherapeutic agent;
   (b) detecting genomic amplification and/or overexpression of a metadherin (MTDH) gene in a tumor sample of the individual; and
   (b) administering to the individual an effective amount of a MTDH inhibitor selected from the group consisting of an antisense molecule and a small molecule.

2. The method of claim 1, wherein the method further comprises detecting genomic amplification of the MTDH gene in the tumor sample.

3. The method of claim 2, wherein the copy number of the MTDH gene is more than two.

4. The method of claim 1, wherein the method further comprises detecting overexpression of the MTDH gene in the tumor sample.

5. The method of claim 1, wherein step (b) comprises detecting genomic amplification of one or more genes at 8q22 using a technique selected from the group consisting of fluorescence in situ hybridization (FISH), comparative genomic hybridization (CGH), high density single nucleotide polymorphism (SNP) genotyping and real time PCR (qPCR).

6. The method of claim 1, wherein step (b) comprises detecting overexpression of one or more genes at 8q22 using a technique selected from the group consisting of reverse-transcription PCR (RT-PCR), immunostaining and in vivo imaging.

7. The method of claim 1, wherein the individual is a human.

8. The method of claim 1, wherein the cancer is selected from the group consisting of breast cancer, colon cancer, lung cancer, pancreatic cancer, prostate cancer, bone cancer, blood cancer, brain cancer and liver cancer.

9. The method of claim 1, wherein the chemotherapeutic agent is selected from the group consisting of cisplatin, docetaxel, doxorubicin, 4-hydroxycyclophosphamide and paclitaxel.

10. The method of claim 1, wherein the chemotherapeutic agent is paclitaxel.

11. The method of claim 1, wherein the cancer is selected from the group consisting of a recurrent cancer, a primary cancer and a metastatic cancer.

12. The method of claim 1, further comprising administering to the individual an effective amount of the chemotherapeutic agent in combination with the MTDH inhibitor.

13. The method of claim 1, wherein the MTDH inhibitor is an antisense molecule.

14. The method of claim 13, wherein the antisense molecule is an siRNA.

15. The method of claim 13, wherein the antisense molecule is an anti-sense RNA.

16. The method of claim 1, wherein the MTDH inhibitor is a small molecule.

17. A method of treating a cancer in an individual, wherein the individual has genomic amplification and/or overexpression of a metadherin (MTDH) gene in a tumor sample of the individual, comprising:
   administering to the individual an effective amount of a chemotherapeutic agent and an effective amount of an MTDH inhibitor selected from the group consisting of an antisense molecule and a small molecule.

18. The method of claim 17, wherein the chemotherapeutic agent is selected from the group consisting of cisplatin, docetaxel, doxorubicin, 4-hydroxycyclophosphamide and paclitaxel.

19. The method of claim 17, wherein the MTDH inhibitor is an antisense molecule.

20. The method of claim 17, wherein the MTDH inhibitor is a small molecule.

\* \* \* \* \*

SEQUENCE LISTING

<160> NUMBER OF SEQ ID NOS: 25

<210> SEQ ID NO 1

<400> SEQUENCE: 1

000

<210> SEQ ID NO 2
<211> LENGTH: 18
<212> TYPE: DNA
<213> ORGANISM: Artificial Sequence
<220> FEATURE:
<223> OTHER INFORMATION: Synthetic -continued

```
<400> SEQUENCE: 2
tggcaaatgt ggccaaca                                                   18

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
tattaggtaa ccgaccccct ctt                                             23

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gagtctcact ctgtggcccg                                                 20

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
tgagcagaga tcatgccatt g                                               21

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
ctcagcacga actgtcccg                                                  19

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ccatggattc aaaccagcac t                                               21

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gcaattgcaa gacggctgt                                                  19
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
aaaccttggc ttacccagga a                                             21

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
tcaggttgac gccgctgt                                                 18

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
ttcgtagccg ttctgctgc                                                19

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tccgagaagc ccaaaccaaa t                                             21

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cttaccctca gccacttcaa                                               20

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
ttttattgag tgccctggct g                                             21

<210> SEQ ID NO 15
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 15
ggcaatgcac atgttggc                                                18

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
aagtggagga catcaccatt g                                            21

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
tcatccctgg taaaggcg                                                18

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
agctgagtga gaacatggcg a                                            21

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
atggtcgaac ctctccttga gc                                           22

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tcgcttcatg caggttgtgg                                              20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
tgtctgcagc ccaagccat                                               19
```

```
<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ggcaggtatc tttgtaacta                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gctgactgat tctggttcat                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cgctacttat gtgaacgtaa                                          20

<210> SEQ ID NO 25
<211> LENGTH: 19
<212> TYPE: DNA
<213> ORGANISM: Artificial Sequence
<220> FEATURE:
<223> OTHER INFORMATION: Synthetic

<400> SEQUENCE: 25
ggttcgacca tatcctgta                                           19
```